US011033272B2

(12) United States Patent
Fegelman et al.

(10) Patent No.: US 11,033,272 B2
(45) Date of Patent: **\*Jun. 15, 2021**

(54) METHODS FOR PARTIAL DIVERSION OF THE INTESTINAL TRACT

(71) Applicants: Ethicon Endo-Surgery, Inc., Cincinnati, OH (US); University of Cincinnati, Cincinnati, OH (US)

(72) Inventors: Elliott J. Fegelman, Cincinnati, OH (US); Randy J. Seeley, Northville, MI (US); Gregory J. Bakos, Mason, OH (US); Jason L. Harris, Lebanon, OH (US)

(73) Assignees: Ethicon Endo-Surgery, Inc., Cincinnati, OH (US); University of Cincinnati, Cincinnati, OH (US)

( \* ) Notice: Subject to any disclaimer, the term of this patent is extended or adjusted under 35 U.S.C. 154(b) by 736 days.

This patent is subject to a terminal disclaimer.

(21) Appl. No.: 15/298,816

(22) Filed: Oct. 20, 2016

(65) Prior Publication Data

US 2017/0035425 A1 Feb. 9, 2017

Related U.S. Application Data

(60) Continuation-in-part of application No. 15/161,512, filed on May 23, 2016, now Pat. No. 10,342,544, (Continued)

(51) Int. Cl.
*A61B 17/11* (2006.01)
*A61B 17/00* (2006.01)

(52) U.S. Cl.
CPC . *A61B 17/1114* (2013.01); *A61B 2017/00862* (2013.01); *A61B 2017/00876* (2013.01); (Continued)

(58) Field of Classification Search
CPC ..... A61B 2017/1117; A61B 2017/1139; A61B 17/1114; A61B 2017/00862; A61B 17/11; (Continued)

(56) References Cited

U.S. PATENT DOCUMENTS 4,777,949 A 10/1988 Perlin
5,562,690 A 10/1996 Green et al.
(Continued)

FOREIGN PATENT DOCUMENTS

CN 1328435 A 12/2001
WO WO 2006/048906 A1 5/2006
(Continued)

OTHER PUBLICATIONS

U.S. Appl. No. 15/161,512; and.
(Continued)

*Primary Examiner* — Shaun L David
*Assistant Examiner* — Christina C Lauer
(74) *Attorney, Agent, or Firm* — Frost Brown Todd LLC

(57) ABSTRACT

Devices and methods are used to modify a metabolic pathway of a digestive system by creating a pathway within the intestinal tract through an anastomosis between a proximal location within the intestinal tract and a distal location within the intestinal tract. In some examples, the small intestine has a first initial length and the created pathway defines a second length of the intestinal tract that is approximately ten to seventy percent of the first initial length of the small intestine.

27 Claims, 53 Drawing Sheets

Related U.S. Application Data which is a division of application No. 14/013,538, filed on Aug. 29, 2013, now Pat. No. 9,364,238.

(60) Provisional application No. 61/812,469, filed on Apr. 16, 2013.

(52) U.S. Cl.
CPC ............... *A61B 2017/1117* (2013.01); *A61B 2017/1139* (2013.01)

(58) Field of Classification Search
CPC ... A61B 17/02; A61B 17/0281; A61B 17/025; A61B 17/0218; A61B 17/0206
See application file for complete search history.

(56) References Cited

U.S. PATENT DOCUMENTS

| | | | |
|---|---|---|---|
| 6,171,320 B1 | 1/2001 | Monassevitch | |
| 6,352,543 B1 * | 3/2002 | Cole | A61B 17/0057 128/898 |
| 7,041,110 B2 | 5/2006 | Yencho et al. | |
| 7,445,622 B2 | 11/2008 | Ortiz et al. | |
| 7,637,919 B2 | 12/2009 | Ishikawa et al. | |
| 7,780,686 B2 | 8/2010 | Park et al. | |
| 8,118,821 B2 | 2/2012 | Mouw | |
| 8,142,454 B2 | 3/2012 | Harrison et al. | |
| 8,197,498 B2 | 6/2012 | Coleman et al. | |
| 8,684,995 B2 | 4/2014 | Sato et al. | |
| 8,728,103 B2 | 5/2014 | Surti et al. | |
| 8,728,105 B2 | 5/2014 | Aguirre | |
| 8,828,031 B2 | 9/2014 | Fox et al. | |
| 8,828,032 B2 | 9/2014 | McWeeney et al. | |
| 8,864,781 B2 | 10/2014 | Surti et al. | |
| 8,870,899 B2 | 10/2014 | Beisel et al. | |
| 9,364,238 B2 | 6/2016 | Bakos et al. | |
| 9,381,041 B2 | 7/2016 | Brown et al. | |
| 9,456,820 B2 | 10/2016 | Gagner et al. | |
| 10,342,544 B2 * | 7/2019 | Bakos | A61B 17/1114 |
| 2006/0036267 A1 | 2/2006 | Saadat et al. | |
| 2007/0142850 A1 | 6/2007 | Fowler | |
| 2008/0051626 A1 | 2/2008 | Sato et al. | |
| 2010/0331866 A1 * | 12/2010 | Surti | A61B 17/1114 606/153 |
| 2011/0137394 A1 | 6/2011 | Lunsford et al. | |
| 2011/0144560 A1 * | 6/2011 | Gagner | A61B 17/1114 604/8 |
| 2016/0262762 A1 | 9/2016 | Bakos et al. | |
| 2019/0021736 A1 | 1/2019 | Bakos et al. | |

FOREIGN PATENT DOCUMENTS

| | | |
|---|---|---|
| WO | WO 2011/100625 | 8/2011 |
| WO | WO 2013/009886 A1 | 1/2013 |

OTHER PUBLICATIONS

Ryou, MD, M. et al., "Endoscopic intestinal bypass creation by using self-assembling magnets in a porcine model," Gastrointestinal Endoscopy, Apr. 2016, 83(4):821-825,.

Ryou, MD, M., et al., "Minimally invasive entero-enteral dual-path bypass using self-assembling magnets," Surgical Endoscopy, Oct. 2016, 30(10):4533-4538.

International Search Report and Written Opinion dated Sep. 22, 2014 for Application No. PCT/US2014/033779, 13 pgs.

U.S. Appl. No. 61/697,845, filed Sep. 7, 2012.

U.S. Appl. No. 61/812,469, filed Apr. 16, 2013.

U.S. Appl. No. 15/161,512;.

U.S. Appl. No. 16/143,650; and.

Chinese Office Action, The First Office Action, and Search Report dated May 2, 2017 for Application No. CN 201480021520.9, 11 pgs.

Chinese Office Action, The Second Office Action dated Nov. 27, 2017 for Application No. CN 201480021520.9, 6 pgs.

Indian Office Action dated Sep. 6, 2020 for Application No. 9739/DELNP/2015, 7 pages.

* cited by examiner

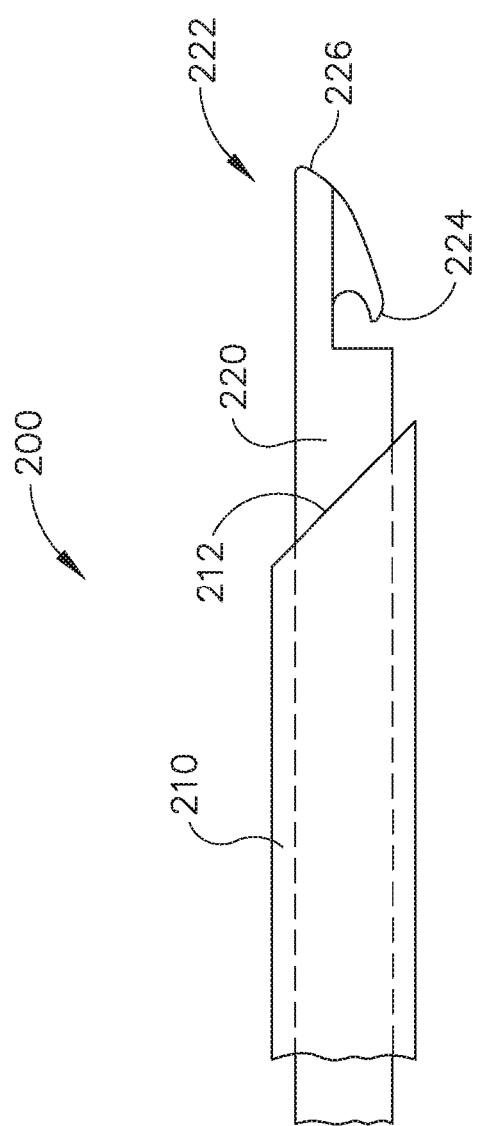

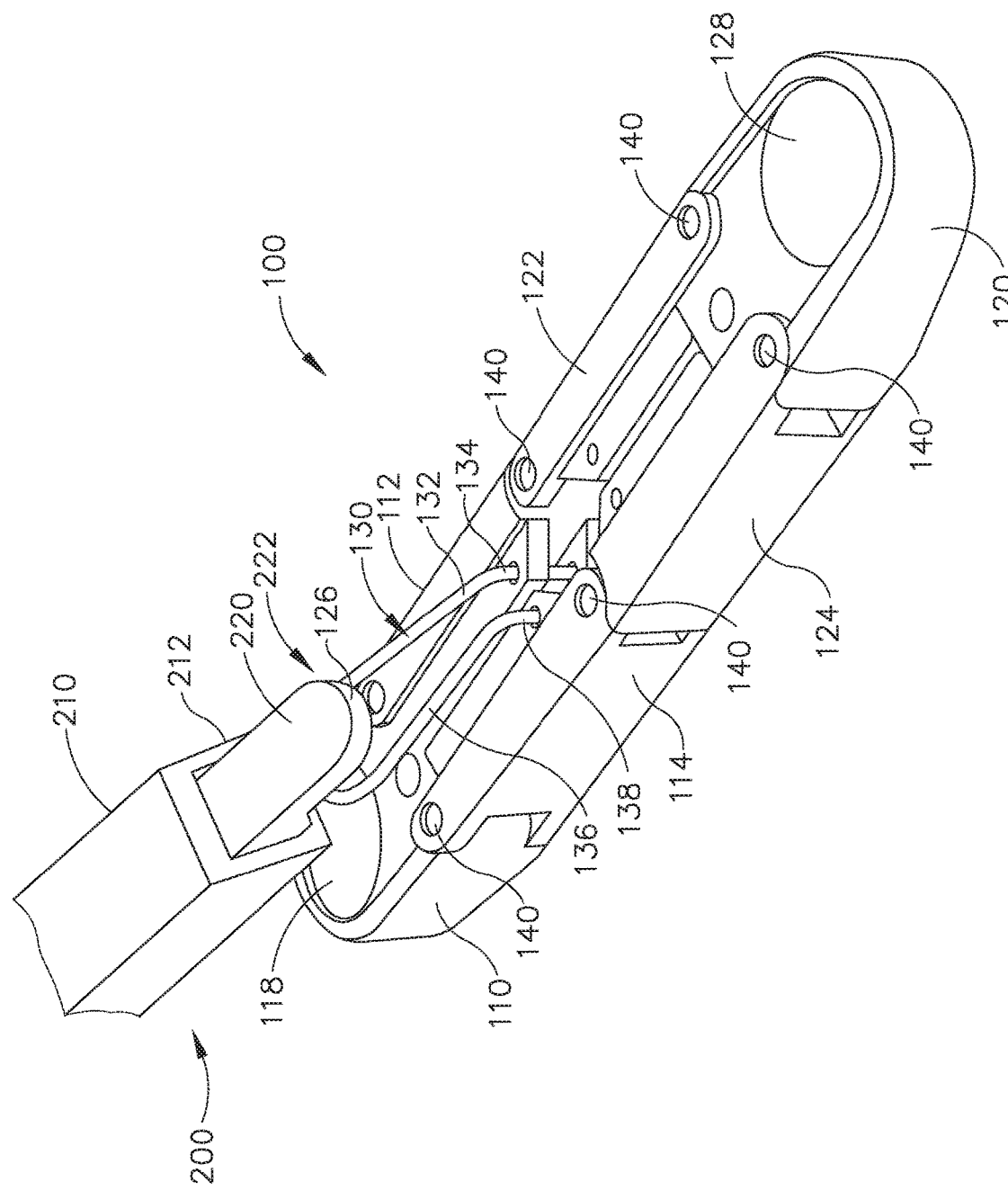

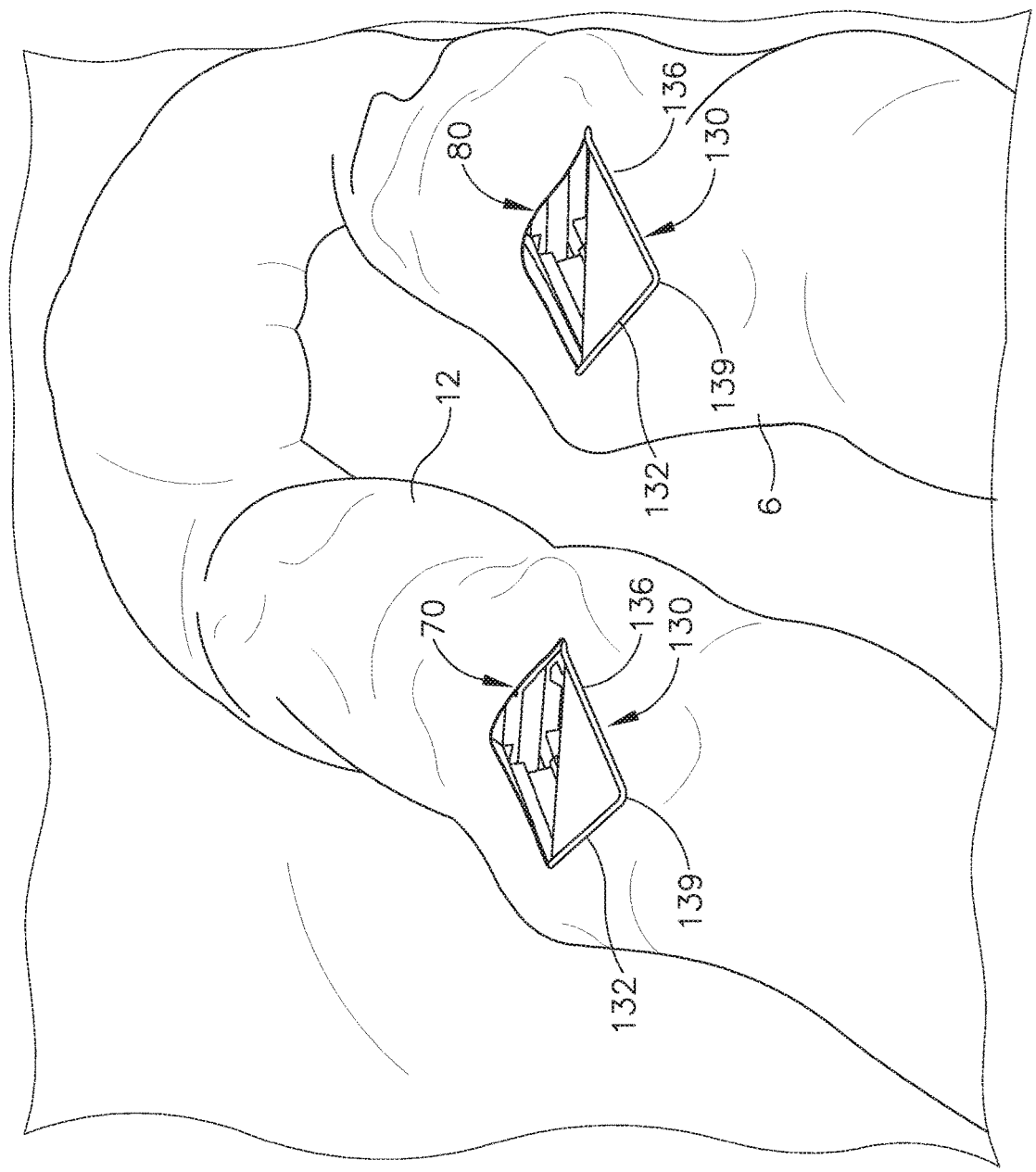

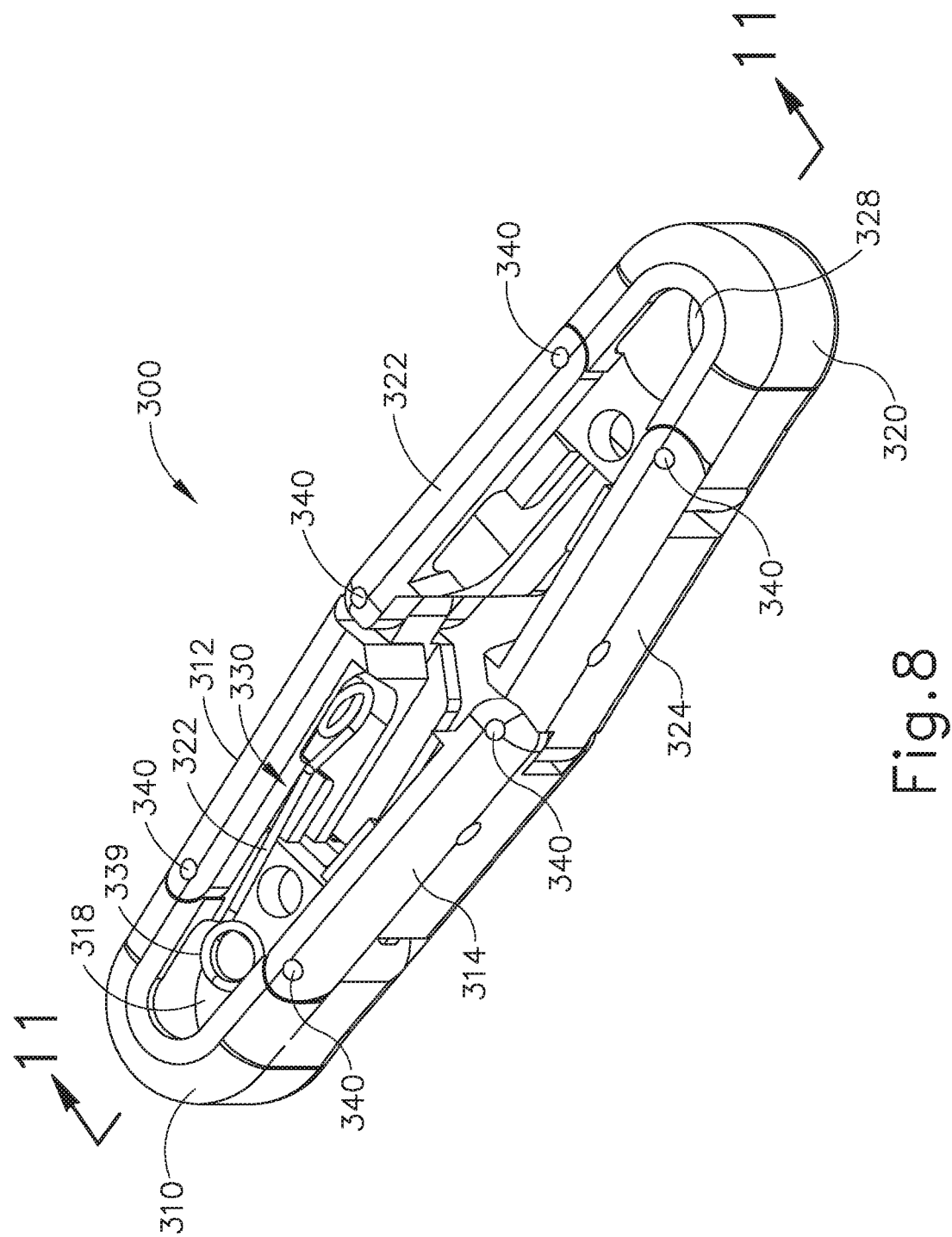

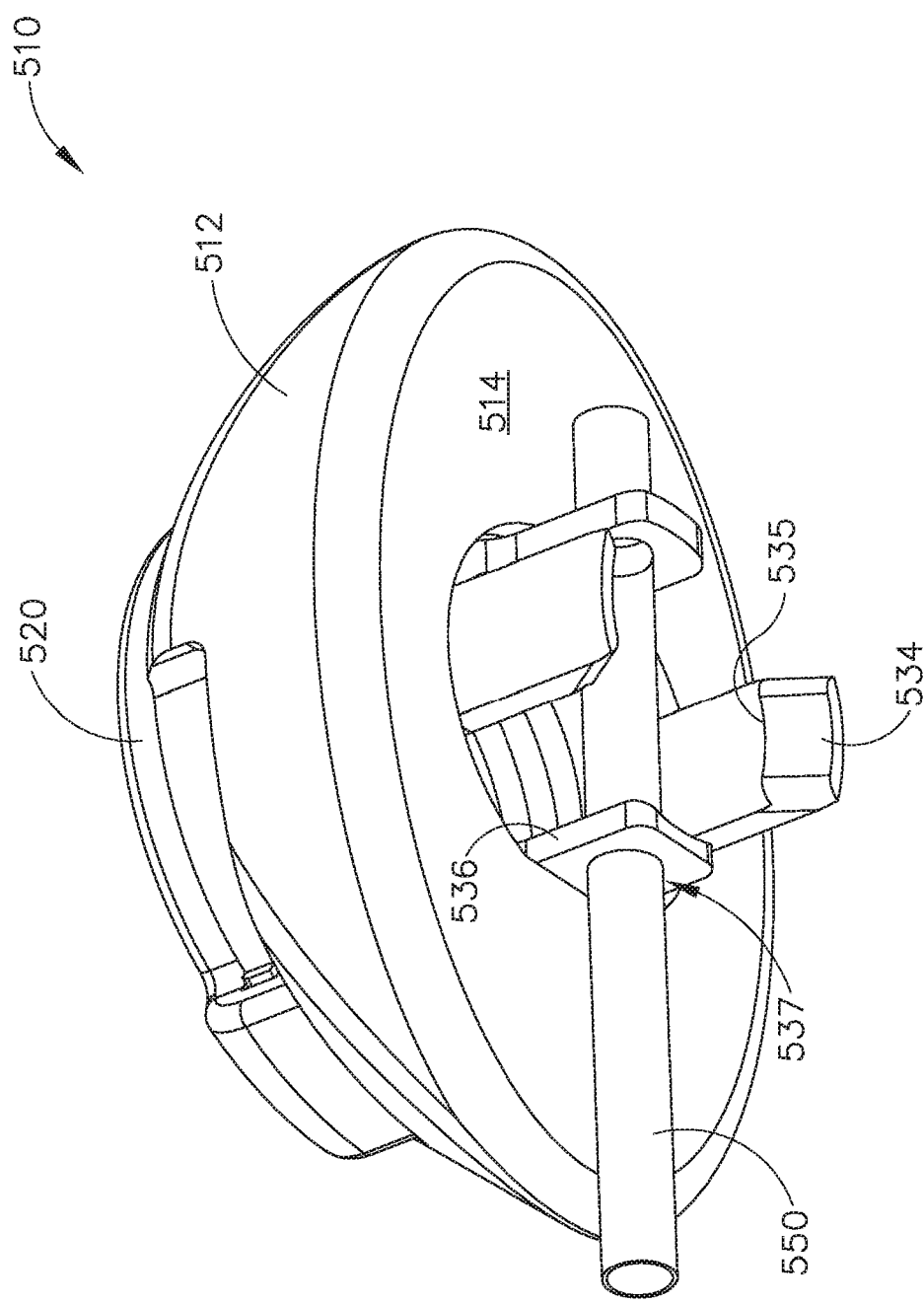

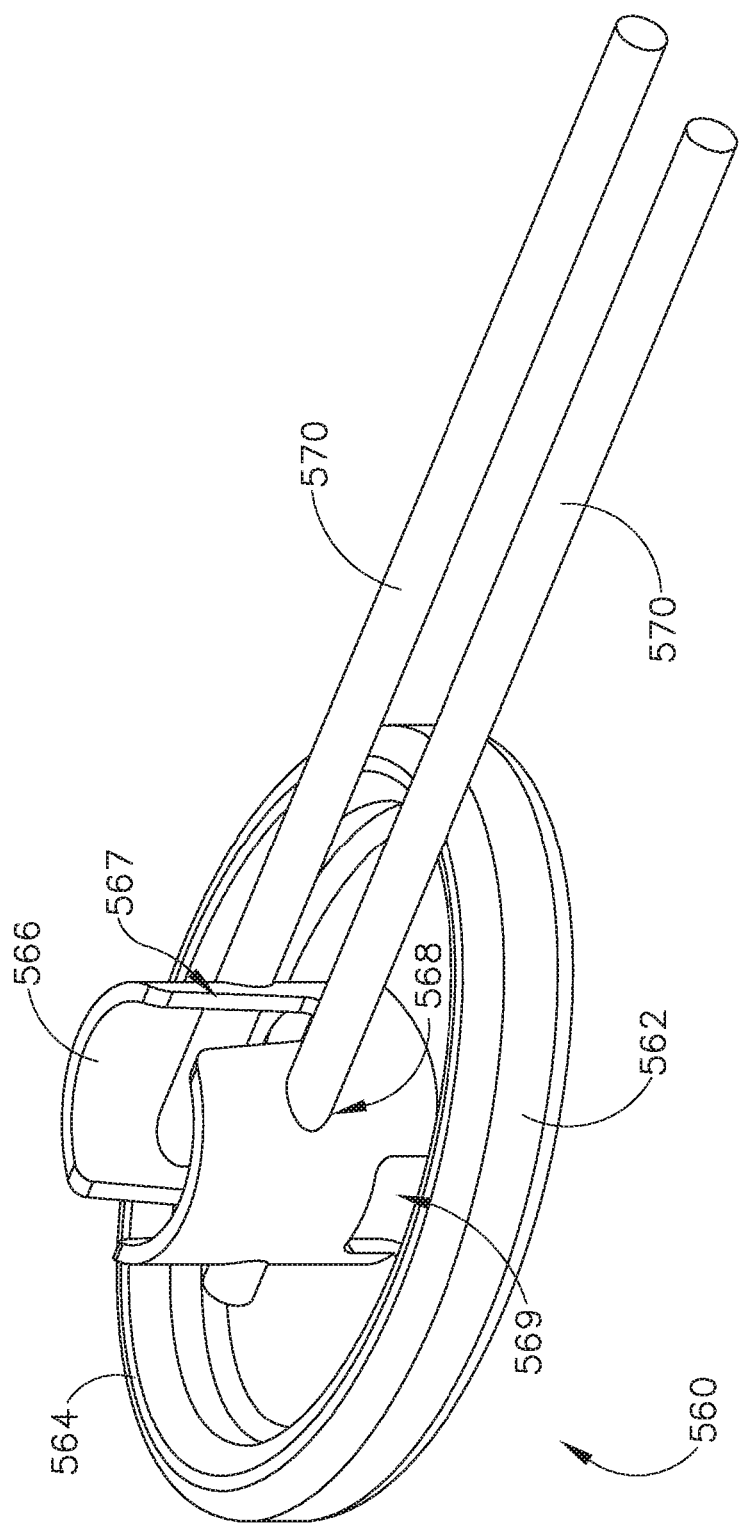

US 11,033,272 B2

METHODS FOR PARTIAL DIVERSION OF THE INTESTINAL TRACT

PRIORITY

This application is a continuation-in-part of U.S. Non-Provisional patent application Ser. No. 15/161,512, filed May 23, 2016, published as U.S. Publication No. 2016/0262762, issued as U.S. Pat. No. 10,342,544 on Jul. 9, 2019, the disclosure of which is incorporated by reference herein; which is a divisional of U.S. Non-Provisional patent application Ser. No. 14/013,538, filed Aug. 29, 2013, issued on Jun. 14, 2016 as U.S. Pat. No. 9,364,238, the disclosure of which is incorporated by reference herein; which claims priority to U.S. Provisional Patent Application No. 61/812,469, filed Apr. 16, 2013, the disclosure of which is incorporated by reference herein.

BACKGROUND

In some instances, it may be desirable to provide a side-to-side anastomosis between two naturally occurring lumens within a patient's body. By way of example only, it may be desirable to provide an anastomosis between two portions of a patient's gastrointestinal tract, such as between the patient's duodenum and the patient's ileum. In some patients, it may improve glucose control, serve as a treatment for type 2 diabetes, and/or provide other results when the jejunum is diverted by an anastomosis. In such a procedure, a first enterotomy may be formed in the sidewall of the duodenum while a second enterotomy is formed in the sidewall of the ileum. The sidewalls may then be placed adjacent to each other to provide fluid communication through the first and second enterotomies, enabling at least some chyme to pass through the first and second enterotomies to travel from the duodenum to the ileum without passing through the jejunum.

One or more devices may be positioned within the first and second enterotomies to hold the sidewalls of the duodenum and ileum together, thereby holding the first and second openings in alignment with each other and maintaining patency through the openings. The device or devices may compress the tissue, which may ultimately result in a serosa-to-serosa adhesion that secures the duodenum sidewall to the ileum sidewall. In addition, tissue captured in the device or devices may eventually necrose, such that the device or devices is/are eventually released into the gastrointestinal tract and subsequently passed through the bowels. Traditional examples of anastomosis devices include Denan's rings and the Murphy button. Examples of anastomosis procedures and associated devices are taught in U.S. Provisional Patent App. No. 61/697,845, entitled "Magnetic Compression Anastomosis Device," filed Sep. 7, 2012, the disclosure of which is incorporated by reference herein.

While a variety of anastomosis devices have been made and used, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 4 depicts a side elevational view of the distal end of an exemplary instrument operable to apply the anastomosis compression device of FIG. 3A;

FIG. 5A depicts a perspective view of the instrument of FIG. 4 engaged with the anastomosis compression device of FIG. 3A, with an arm of the instrument in an extended position;

FIG. 6I depicts a perspective view of a patient's digestive system during the anastomosis procedure of FIG. 6A, with the anastomosis compression device of FIG. 3A in the expanded configuration within the patient's duodenum, and with a portion of tissue omitted to show the entirety of the anastomosis compression device;

FIG. 6M depicts a perspective view of a patient's digestive system during the anastomosis procedure of FIG. 6A, with the anastomosis compression device of FIG. 3A in the expanded configuration within the patient's ileum;

FIG. 6O depicts a perspective view of a patient's digestive system during the anastomosis procedure of FIG. 6A, with the anastomosis compression devices holding the openings in the duodenum and ileum together to form an anastomosis;

FIG. 8 depicts a perspective view of an exemplary alternative anastomosis compression device, in a compressed state;

FIG. 18 depicts a perspective view of the bottom side of a first subassembly of the anastomosis compression device of FIG. 15;

FIG. 19 depicts a perspective view of the top side of a second subassembly of the anastomosis compression device of FIG. 15;

Figure 1:
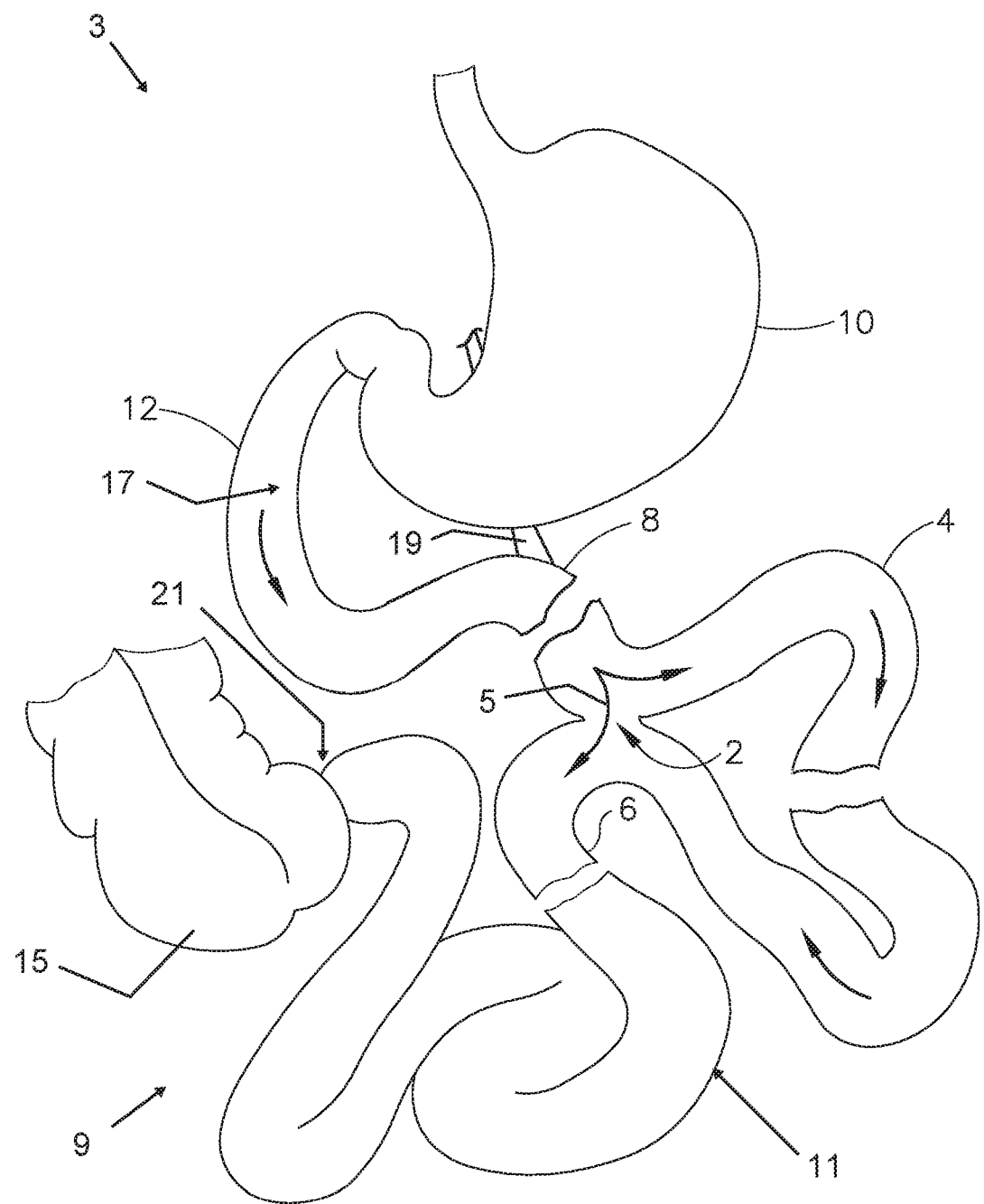
FIG. 1 depicts a diagrammatic view of a portion of a patient's digestive system, showing an anastomosis in the small intestines to divert chyme from the patient's jejunum.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Intestinal Anastomosis

As noted above, it may be desirable to provide an anastomosis between two naturally occurring lumens within a patient's body, such as within the patient's gastrointestinal tract. FIG. 1 shows an example of an anastomosis (2) formed between a proximal portion of a patient's jejunum (4) and the patient's ileum (6). The anastomosis (2) is located just distal to the duodenojujenal flexure (8). The anastomosis (2) provides a path for fluid communication from the proximal portion of a patient's jejunum (4) directly to the ileum (6), thereby providing a bypass of the majority of the jejunum (4). In particular, chyme that exits the stomach (10) may flow directly through the duodenum (12), then through just the proximal portion of the jejunum (4) and directly to the ileum (6) via the anastomosis (2), without passing through the majority of the jejunum (4). In some instances, a portion of the chyme that exits the stomach (10) flows directly from the proximal portion of the jejunum (4) to the ileum (6) via the anastomosis (2); while another portion passes the anastomosis (2) and flows through the remainder of the jejunum (4). Thus, anastomosis (2) may form a complete diversion of chyme or a partial diversion of chyme.

It should be understood that it may be necessary to create at least two enterotomies in order to provide an anastomosis (2)—one opening for the upstream region of the lumen and another opening for the downstream region of the lumen. The tissue surrounding the two enterotomies may be secured together with the enterotomies in alignment in order to provide the anastomosis (2). Once these openings are aligned at the site of the anastomosis (2), a device may be used to compress and hold the tissue together to maintain alignment of the enterotomies forming the anastomosis (2). Holding the tissue together may promote serosa-to-serosa adhesion, such that the serosa that is apposed at the anastomosis (2) eventually bonds together and thereby maintains structural integrity of the anastomosis (2) without the need for assistance by a surgically introduced device. In some instances, it may be necessary to create one or more additional enterotomies in the gastrointestinal tract in order to surgically introduce a device that compresses the tissue together to maintain alignment of the openings forming the anastomosis (2). These additional enterotomies may need to be closed (e.g., using suture, etc.) after the anastomosis compression device has been introduced to the site of the anastomosis (2). The creation and subsequent closure of these additional access enterotomies may impose additional time, cost, and/or risk in the surgical procedure.

The following disclosure includes examples of anastomosis compression devices that may be used to compress and hold the tissue together to maintain alignment and patency of the openings forming the anastomosis (2). It should be understood that each of these devices may be introduced into the lumens of the jejunum and ileum via the same enterotomies that will eventually form the anastomosis (2). In other words, it is not necessary to create (and subsequently close) any additional enterotomies in order to position the below described devices at the site of the anastomosis (2). It should also be understood that the devices described below are configured to maintain their positions at the anastomosis (2) without requiring the devices to be sutured in place. The devices include one device portion that is placed in one part of the gastrointestinal tract and another device portion that is placed in another part of the gastrointestinal tract. These device portions are biased toward each other (e.g., by a resilient member, by magnetic forces, etc.) and thereby compress tissue between opposing surfaces of the device portions. The compression provides a fluid-tight seal at the anastomosis (2), preventing chyme, etc. from leaking at the anastomosis (2). The edges of the opposing device surfaces that contact tissue are rounded or chamfered to prevent the device portions from cutting through the tissue of the gastrointestinal tract. The compressed tissue eventually necroses due to ischemia, such that the device portions and necrosed tissue eventually leave the anastomosis (2) and pass through the gastrointestinal tract.

Figure 2:
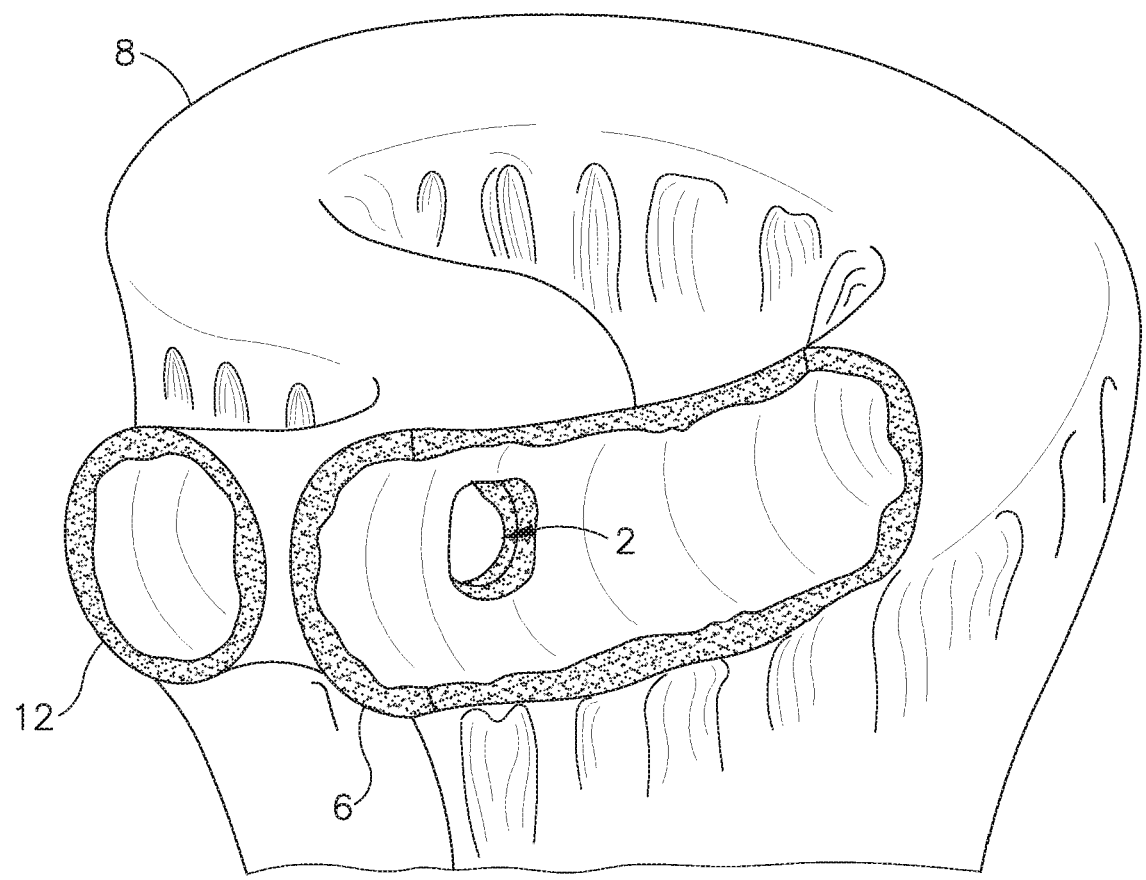
FIG. 2 depicts a partial perspective view of another exemplary anastomosis to divert chyme from the patient's jejunum.

While FIG. 1 shows the anastomosis (2) positioned just distal to the duodenojujenal flexure (8) (e.g., approximately 100 cm distal to the duodenojujenal flexure (8)) and coupling the proximal portion of the jejunum (4) with the ileum (6), it should be understood that an anastomosis (2) may be positioned at various other suitable locations within the gastrointestinal tract. For instance, an anastomosis (2) may be located proximal to the duodenojujenal flexure (8), thus directly coupling the duodenum (12) with the ileum (6) such that chyme may bypass the entire length of the jejunum (4) as shown in FIG. 2. In another example, an anastomosis (2) may be located about 100 centimeters distal to the duodenojujenal flexure (8) and/or ligament of Treitz (19). As another merely illustrative example, an anastomosis (2) may provide a direct coupling between the stomach (10) and jejunum (4), such that chyme may bypass the duodenum (12); or between the esophagus and stomach (10) to reconnect the tract after removing a portion of the esophagus; or between the colon and rectum after removing a portion of the colon due to a lesion, etc. In some examples, the anastomosis (2) may have a side-to-side orientation to connect adjacent portions of a lumen such as the small intestine. Other suitable locations for an anastomosis (2) within the gastrointestinal tract will be apparent to those of ordinary skill in the art in view of the teachings herein. It should also be understood that an anastomosis (2) may be located elsewhere in a patient's body; and that an anastomosis need not necessarily be located within the patient's gastrointestinal tract. It is contemplated that the exemplary anastomosis compression devices described below (and variations thereof) may be used in various locations throughout a patient's body, not just the gastrointestinal tract.

By way of further example, and not limitation, in one example a metabolic pathway of the digestive system (3) is modified by creating a pathway (5) within the intestinal tract (9) by establishing a connection between a proximal location within the small intestine (11) and a distal location within the intestinal tract (9). In the present example, the connection is formed by way of an anastomosis (2). In some examples, the connection is formed by way of a side-to-side anastomosis. Also in the present example, the proximal location within the small intestine (11) is distal to the duodenal papilla (17). In this manner, the pathway (5) serves as a shortcut added to the existing pathway defined by the intestinal tract (9) of the digestive system (3), such that the existing pathway of the intestinal tract (9) remains intact. Accordingly, the procedures involved to create the pathway (5) do not transect, remove, or seal off any portion of the digestive system (3).

Furthermore, the procedure is thus fully reversible and the entire digestive system (3) can be fully returned to its original state.

In modifying the metabolic pathway of the digestive system (3) to create the pathway (5), the small intestine (11) itself defines a first initial length. The pathway (5) created defines a second length. This second length is represented as the bypassed region or bypass portion of the intestinal tract (9) that is created due to the anastomosis (2). In this manner, the bypassed region is that length of the intestinal tract (9) that chyme passing through the intestinal tract (9) would not travel through when the chyme instead follows the shortcut pathway created by the anastomosis (2). In this way, the second length can also be defined as the length commencing at the anastomosis (2) at the proximal location in the intestinal tract (9) and terminating at the anastomosis (2) at the distal location in the intestinal tract (9). In the present example the second length can be between about 10% and 70% of the first initial length of the small intestine (11). In one instance of the present example, the second length is less than about 60% of the initial overall length of the small intestine (11).

When performing the method to create the pathway (5) within the intestinal tract (9), natural orifice translumenal endoscopic surgery (also referred to as NOTES) may be used, where the procedure involves one or more flexible endoscopes that are inserted into a patient via a natural orifice of the patient. Such natural orifices can include the mouth or oral cavity for transgastric procedures, the anus for transcolonic procedures, and/or the vagina for transvaginal procedures. Such natural orifices are not limited to only those mentioned above, but may instead include any natural orifice of a patient. In some instances a previous scar site may be used to insert the one or more flexible endoscopes, such as through the navel or umbilicus. In view of the teachings herein, one skilled in the art will recognize that methods for enteroscopy such as double balloon enteroscopy or spiral enteroscopy using a system like the Endo-Ease Discovery® SB made by Spirus Medical, LLC can facilitate the identification of both proximal and distal locations via flexible endoscopy. Furthermore, some procedures for creating the pathway (5) may be performed completely endoscopically, completely laparoscopically, in a completely open procedure, or in a mix of any of these procedure types and/or in combination with natural orifice procedure types. In view of the teachings herein, the various types of procedures and levels of invasiveness that may be used with the methods of creating pathways within the intestinal tract (9) described herein will be apparent to those of ordinary skill in the art.

In the present example, the proximal location, in addition to being distal to the duodenal papilla (17), can be in the duodenum (12), jejunum (4), or the ileum (6). The distal location can be in the jejunum (4), ileum (6), or colon (15). In one instance of the present example, the proximal location is in the duodenum (12), while the distal location is in the jejunum (4). In another instance, the proximal location is in the duodenum (12), while the distal location is in the ileum (6). In another instance, the proximal location is in the jejunum (4), while the distal location is also in the jejunum (4). In another instance, the proximal location is in the jejunum (4), while the distal location is in the ileum (6). In another instance, the proximal location is in the jejunum (4), while the distal location is in the colon (15). In another instance, the proximal location is in the ileum (6), while the distal location is also in the ileum. In another instance, the proximal location is in the ileum (6), while the distal location is in the colon (15). In view of the teachings herein, other locations for the proximal location and the distal location for the created pathway (5) will be apparent to those of ordinary skill in the art.

In the example where the proximal location for the connection is in the jejunum (4) and the distal location is in the colon (15), in one instance the proximal location is at least about 200 centimeters distal from the ligament of Treitz (19). In the example where the proximal location for the connection is in the jejunum (4), in one instance, the proximal location is between about 10 centimeters and about 200 centimeters distal to the ligament of Treitz (19), and in another instance 100 centimeters distal to the ligament of Treitz (19). As mentioned above, in procedures where the proximal location for the connection is in the jejunum (4), one or more flexible endoscopes may be inserted into a patient via the oral cavity and/or the colon (15).

In the example where the distal location for the connection is in the ileum (6), in one instance the distal location is between about 10 centimeters and 300 centimeters proximal to the ileocecal junction (21), and in another instance 250 centimeters proximal to the ileocecal junction (21). In the example where the distal location for the connection is in the colon (15), it may be in either the ascending portion of the colon, the transverse portion of the colon, or the descending portion of the colon. In another example, the distal location is about 250 centimeters proximal to the ileocecal junction (21), while the proximal location is about 100 centimeters from the ligament of Treitz (19).

In an example where the connection is a side-to-side anastomosis (2), by way of example only and not limitation, the procedure includes forming the anastomosis (2) by compression. In some such procedures, the procedure involves introducing a first magnetically attractable device (100) to a first attachment region at the proximal location. Then the procedure involves introducing a second magnetically attractable device (100) to a second attachment region at the distal location. Either one or both of the first and second magnetically attractable devices (100) include at least one magnet (118). Also, the first magnetically attractable device (100) includes a surface that mates with, or is configured to be oriented adjacent to, a corresponding surface on the second magnetically attractable device. The procedure further includes compressing a first lumen wall at the first attachment region and a second lumen wall at the second attachment region between the first and second magnetically attractable devices (100). Further exemplary features and functionalities that may be incorporated into magnetically attractable devices (100) will be described in greater detail below; while others will be apparent to those of ordinary skill in the art in view of the teachings herein. It should be understood, however, that magnetically attractable devices need not necessarily be used in all versions of the procedures described herein.

In another example where the connection is a side-to-side anastomosis (2), by way of example only and not limitation, the procedure includes forming the anastomosis (2) by mechanical fastening. In this regard the procedure involves creating a first enterotomy (70) at the proximal location, creating a second enterotomy (80) at the distal location, and mechanically fastening the first and second enterotomies (70, 80).

By way of further example, and not limitation, in one example the pathway (5) is created within the intestinal tract (9) by forming a first opening (70) in a first hollow organ (11), and forming a second opening (80) in a second hollow organ (11). It should be understood that the first hollow organ and the second hollow organ can be separate organs or different portions of the same organ. By way of example and not limitation, the first and second hollow organs may be different portions of the small intestine. In other examples the first and second hollow organs may be the small intestine and colon respectively. In view of the teachings herein, other examples for the first and second hollow organs will be apparent to those of ordinary skill in the art.

With the first and second openings (70, 80) created, a first compression device (100) is inserted into the first opening (70), and a resilient feature (130) of the first compression device (100) is secured to a portion of tissue adjacent to the first opening (70). In this manner the secured resilient feature (130) of the first compression device (100) is positioned on the exterior of the first hollow organ (11). A second compression device (100) is inserted into the second opening (80), and a resilient feature (130) of the second compression device (100) is secured to a portion of tissue adjacent to the second opening (80). In this manner the secured resilient feature (130) of the second compression device (100) is positioned on the exterior of the second hollow organ (11). To further create the pathway (5), the first and second hollow organs (11) are moved toward each other to align the first and second compression devices (100) with each other. With the first and second compression devices (100) aligned, their positions are secured relative to each other, and a layer of tissue from each of the first hollow organ (11) and the second hollow organ (11) is compressed in apposition between the secured first and second compression devices (100).

In one instance of the proceeding example for creating the pathway (5) within the intestinal tract (9), the first opening (70) is formed within the small intestine (11) at a location distal to the duodenal papilla (17), and the second opening (80) is proximal to the ileocecal junction (21). In another instance, the first opening (70) is formed within the small intestine (11) at a location distal to the duodenal papilla (17), and the second opening (80) is distal to the ileocecal junction (21). In yet another instance, the first opening (70) is formed within the jejunum (4) at a location about 100 centimeters (or about one-third the length of the jejunum) distal to the ligament of Treitz (19), and the second opening (80) is formed within the jejunum (4) at a location about 250 centimeters proximal to the ileocecal junction (21). In another instance, the first opening (70) is formed in a proximal portion of the jejunum (4), and the second opening (80) is formed distal to the first opening (70) at a distance between about 10% and about 70% of the length of the small intestine (11).

The above examples and procedures are merely exemplary and various modifications in the locations used or steps performed in creating one or more pathways within the digestive system of a patient will be apparent to those or ordinary skill in the art in view of the teachings herein.

The procedures described above and elsewhere herein may be performed using any of the various devices described below. In addition, or in the alternative, the procedures described above and elsewhere herein may be performed using any of the devices described in U.S. Pat. No. 8,828,031, entitled "Apparatus for Forming an Anastomosis," issued Sep. 9, 2014, the disclosure of which is incorporated by reference herein; U.S. Pat. No. 8,828,032, entitled "Methods and Apparatus for Magnet-Induced Compression Anastomosis Between Adjacent Organs," issued Sep. 9, 2014, the disclosure of which is incorporated by reference herein; U.S. Pat. No. 7,445,622, entitled "Anastomotic Ring Applier with Double Motion Actuation," issued Nov. 4, 2008, the disclosure of which is incorporated by reference herein; U.S. Pat. No. 8,142,454, entitled "Apparatus and Method for Magnetic Alteration of Anatomical Features," issued Mar. 27, 2012, the disclosure of which is incorporated by reference herein; U.S. Pat. No. 6,171,320, entitled "Surgical Clip," issued Jan. 9, 2001, the disclosure of which is incorporated by reference herein; U.S. Pat. No. 8,870,899, entitled "Self-Assembling Magnetic Anastomosis Device Having an Exoskeleton," issued Oct. 28, 2014, the disclosure of which is incorporated by reference herein; U.S. Pat. No. 7,780,686, entitled "Anastomotic Device," issued Aug. 24, 2010, the disclosure of which is incorporated by reference herein; U.S. Pat. No. 7,637,919, entitled "Anastomosis System for Performing Anastomosis in Body," issued Dec. 29, 2009, the disclosure of which is incorporated by reference herein; U.S. Pat. No. 8,197,498, entitled "Gastric Bypass Devices and Procedures," issued Jun. 12, 2012, the disclosure of which is incorporated by reference herein; U.S. Pat. No. 9,381,041, entitled "Methods and Devices for Access Across Adjacent Tissue Layers," issued Jul. 5, 2016, the disclosure of which is incorporated by reference herein; U.S. Pat. No. 8,864,781, entitled "Intestinal Bypass Using Magnets," issued Oct. 21, 2014, the disclosure of which is incorporated by reference herein; U.S. Pat. No. 8,684,995, entitled "Treatment Method," issued Apr. 1, 2014, the disclosure of which is incorporated by reference herein; U.S. Pat. No. 9,456,820, entitled "Incisionless Gastric Bypass Method and Devices," issued Oct. 4, 2016, the disclosure of which is incorporated by reference herein; U.S. Pub. No. 2011/0137394, entitled "Methods and Systems for Penetrating Adjacent Tissue Layers," published Jun. 9, 2011, now abandoned, the disclosure of which is incorporated by reference herein; U.S. Pub. No. 2007/0142850, entitled "Compression Anastomosis Device," published Jun. 21, 2007, now abandoned, the disclosure of which is incorporated by reference herein; U.S. Pub. No. 2006/0036267, entitled "Methods and Apparatus for Performing Malabsorptive Bypass Procedures within a Patient's Gastro-Intestinal Lumen," published Feb. 16, 2006, now abandoned, the disclosure of which is incorporated by reference herein; the journal article entitled "Endoscopic Intestinal Bypass Creation by Using Self-Assembling Magnets in a Porcine Model," by Dr. Marvin Ryou et al., from *Gastrointestinal Endoscopy*, Vol. 83, No. 4, pp. 821-25, 2016; and/or the journal article entitled "Minimally Invasive Entero-Enteral Dual-Path Bypass Using Self-Assembling Magnets," by Dr. Marvin Ryou et al., from *Surgical Endoscopy*, published online by Springer Feb. 19, 2016. Still other devices that may be used to perform the procedures described herein will be apparent to those of ordinary skill in the art in view of the teachings herein.

II. Exemplary Folding Anastomosis Compression Device

A. Structural Features of Exemplary Folding Anastomosis Compression Device

Figure 3A:
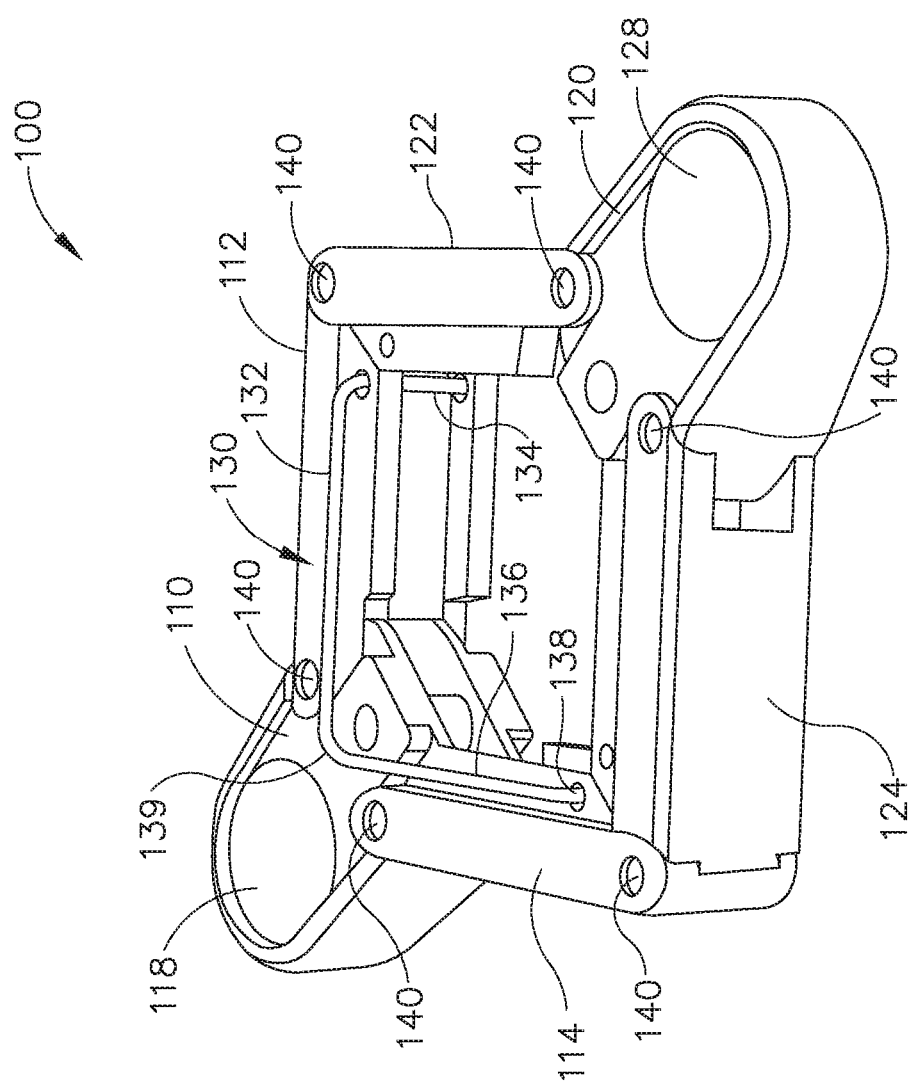
FIG. 3A depicts a perspective view of an exemplary anastomosis compression device, in an expanded state.
Figure 3B:
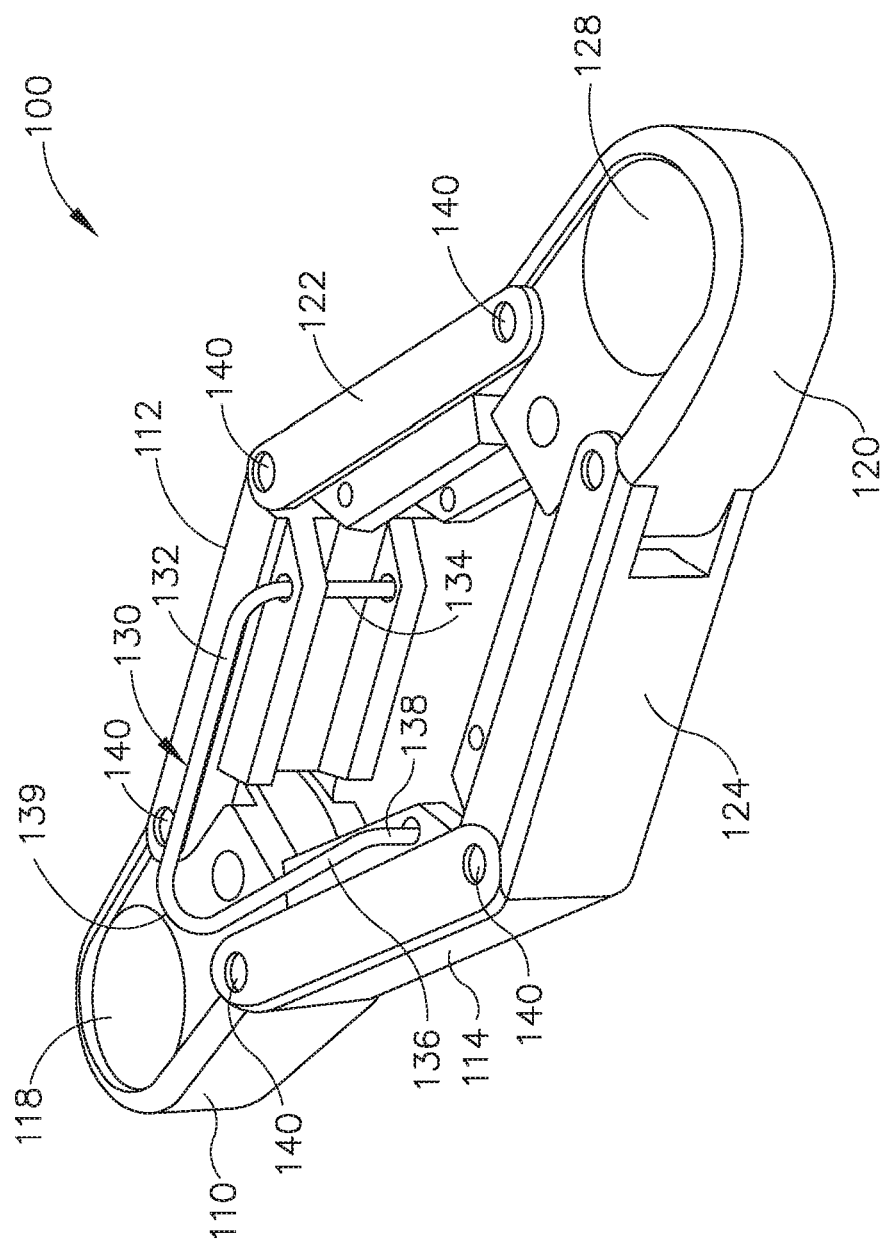
FIG. 3B depicts a perspective view of the anastomosis compression device of FIG. 3A, in a partially compressed state.
Figure 3C:
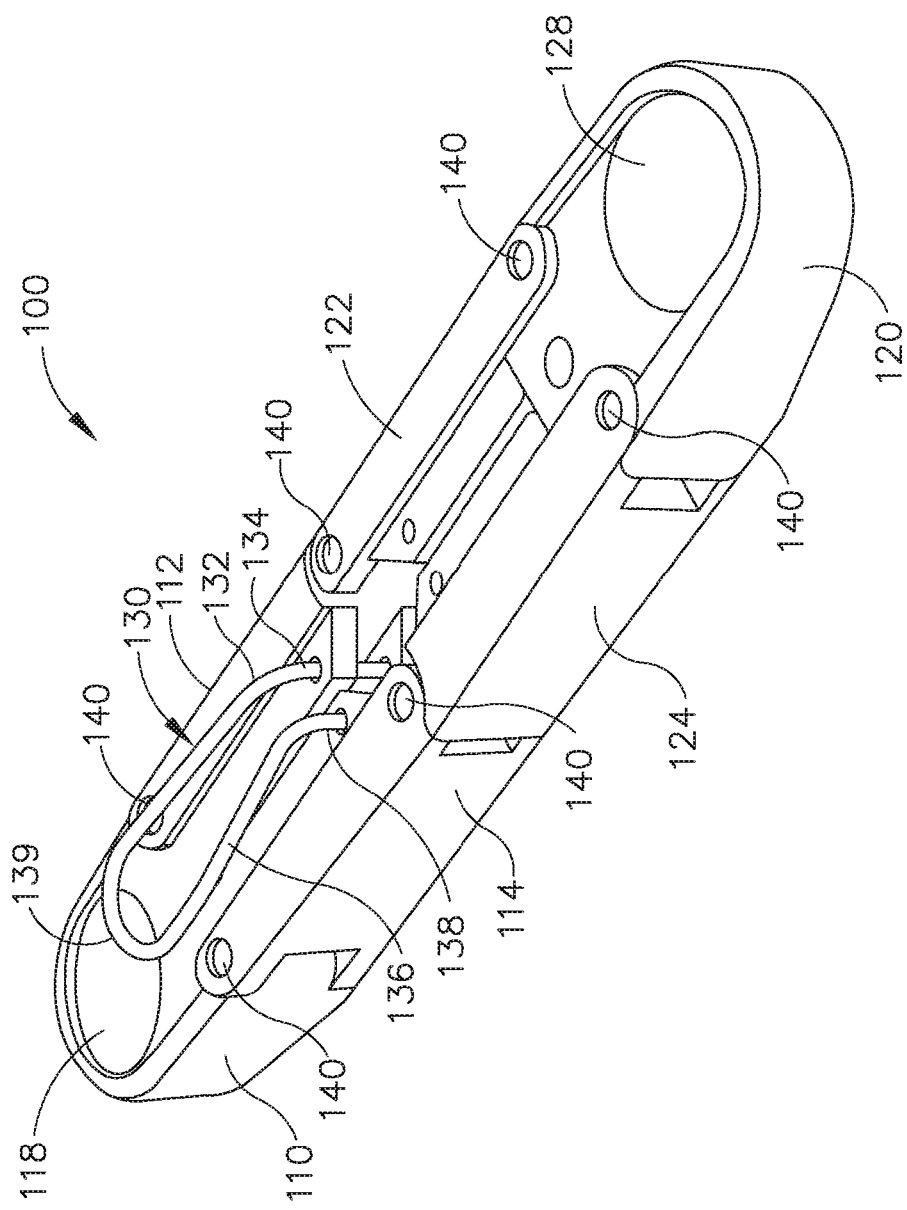
FIG. 3C depicts a perspective view of the anastomosis compression device of FIG. 3A, in a compressed state.

FIGS. 3A-3C show an exemplary folding anastomosis compression device (100). Device (100) of the present example comprises a first end member (110), a second end member (120), a set of links (112, 114, 122, 124), and a resilient member (130). A first magnet (118) is disposed in first end member (110) while a second magnet (128) is disposed in second end member (120). Links (112, 114) are pivotally coupled with first end member (110) by pins (140). Similarly, links (122, 124) are pivotally coupled with second end member (120) by pins (140). Link (112) is coupled with link (122) by a pin (140); while link (114) is coupled with link (124) by a pin (140). It should be understood that the pivotal couplings provided by pins (140) enable links (112,

114, 122, 124) to pivot, thereby enabling device (100) to transition between an expanded configuration (FIG. 3A), to a partially compressed or collapsed configuration (FIG. 3B), and further to a fully compressed or collapsed configuration (FIG. 3C). When device (100) is in the expanded configuration, links (112, 114, 122, 124) define a diamond-shaped opening. In the present example, device (100) is configured such that device (100) may fit through a conventional trocar (e.g., a 12 mm trocar) when device (100) is in the compressed state. Various suitable dimensions and other structural configurations that may be used for device (100) will be apparent to those of ordinary skill in the art in view of the teachings herein.

Resilient member (130) of the present example comprises a wire formed of resilient material. By way of example only, resilient member (130) may be formed of nitinol and/or any other suitable material(s). Resilient member (130) defines a first arm (132) having a first tip region (134), a second arm (136) having a second tip region (138), and a bend (139) separating first arm (132) from second arm (136). First tip region (134) and the remainder of first arm (132) together define an angle of approximately 90°, such that first tip region (134) extends transversely from first arm (132). First tip region (134) is secured to link (112). Second tip region (138) and the remainder of second arm (136) together define an angle of approximately 90°, such that second tip region (138) extends transversely from second arm (136). Second tip region (138) is secured to link (114). Bend (139) is configured such that arms (132, 136) together define an angle of approximately 45° when device (100) is in the expanded configuration. Of course, the various regions of resilient member (130) may define any other suitable angles.

Resilient member (130) is configured to resiliently bias device (100) to the expanded configuration. In particular, tip regions (134, 138) bear outwardly on their associated links (112, 114). In some versions, resilient member (130) is resiliently biased to assume a straight configuration where arms (132, 136) would together define an angle of approximately 180°. Thus, resilient member (130) may remain stressed when device (100) is in the expanded configuration. In some other versions, resilient member (130) is resiliently biased to assume a configuration where arms (132, 136) would together define an obtuse angle, an angle of approximately 90°, or an acute angle. It should be understood that, as links (112, 114) are resiliently biased outwardly by tip regions (134, 138) bearing directly on links (112, 114), links (112, 114) will also drive links (122, 124) outwardly due to the coupling via pins (140). Resilient member (130) will thus indirectly drive links (122, 124) outwardly via links (112, 114). As will be described in greater detail below, resilient member (130) may be engaged by an applier instrument (200), which may hold device (100) in a compressed configuration while device (100) is being applied at an anastomosis site.

In some versions, one or more torsion springs are used to resiliently bias device (100) to the expanded configuration, in addition to or as an alternative to resilient member (130) biasing device (100) to the expanded configuration. By way of example only, a torsion spring may be positioned in first end member (110) to resiliently bear outwardly on links (112, 114) (e.g., via arms that extend to the inner regions of links (112, 114), etc.). In addition or in the alternative, a torsion spring may be positioned in second end member (120) to resiliently bear outwardly on links (122, 124) (e.g., via arms that extend to the inner regions of links (122, 124), etc.). Other suitable ways in which device (100) may be resiliently biased will be apparent to those of ordinary skill in the art in view of the teachings herein.

Resilient member (130) of the present example is also configured to flex at the bend separating first tip region (134) from the remainder of first arm (132); and at the bend separating second tip region (138) from the remainder of second arm (136). However, resilient member (130) is configured to bias arms (132, 136) such that bend (139) is biased toward first end member (110). In other words, resilient member (130) is biased toward a position where arms (132, 136) are oriented generally parallel with links (112, 114, 122, 124) as shown in FIGS. 3A-3C. The flexibility of resilient member (130) at the bend separating first tip region (134) from the remainder of first arm (132), and at the bend separating second tip region (138) from the remainder of second arm (136), enables bend (139) and arms (132, 136) to be deflected away from links (112, 114). Such deflection may facilitate coupling of resilient member (130) with an applier instrument (200) as will be described in greater detail below. Such deflection may also facilitate coupling of resilient member (130) with tissue adjacent to an enterotomy as will also be described in greater detail below.

It should be understood from the foregoing that resilient member (130) is configured to provide a resilient bias along at least two different paths. One such path is along a plane that is parallel to a plane defined by the upper surfaces of links (112, 114, 122, 124). This bias urges device (100) to the expanded configuration. Put another way, the path of this bias is along the path traveled by links (112, 114, 122, 124) during the transition between the compressed configuration and the expanded configuration. The other path of resilient bias is along a plane that is perpendicular to the plane defined by the upper surfaces of links (112, 114, 122, 124). This bias urges resilient member (130) to a position where bend (139) and arms (132, 136) are oriented along a plane that is substantially parallel to a plane defined by the upper surfaces of links (112, 114, 122, 124). Put another way, the path of this bias is perpendicular to the path traveled by links (112, 114, 122, 124) during the transition between the compressed configuration and the expanded configuration. In some other versions, more than one resilient member (130) is used to provide the biases along these different paths.

While resilient member (130) is configured to facilitate coupling of resilient member (130) with tissue adjacent to an enterotomy in the present example, various other kinds of features may facilitate such coupling in addition to or as an alternative to resilient member (130) facilitating such coupling. By way of example only, spikes, other projections, meshes, wire bristles, snap rings, suture purse strings, adhesives, and/or various other features may be provided to facilitate coupling of resilient member (130) with tissue adjacent to an enterotomy.

While device (100) only has one resilient member (130) in the present example, it should be understood that device (100) may have more than one resilient member (130). By way of example only, a second resilient member (130) may be secured to links (122, 124). Such a second resilient member (130) may be configured and positioned as a mirror image of resilient member (130) described above, and may thus provide the same kind of operability as resilient member (130) described above. Still other suitable configurations will be apparent to those of ordinary skill in the art in view of the teachings herein.

B. Exemplary Applier Instrument for Folding Anastomosis Compression Device

Figure 5B:
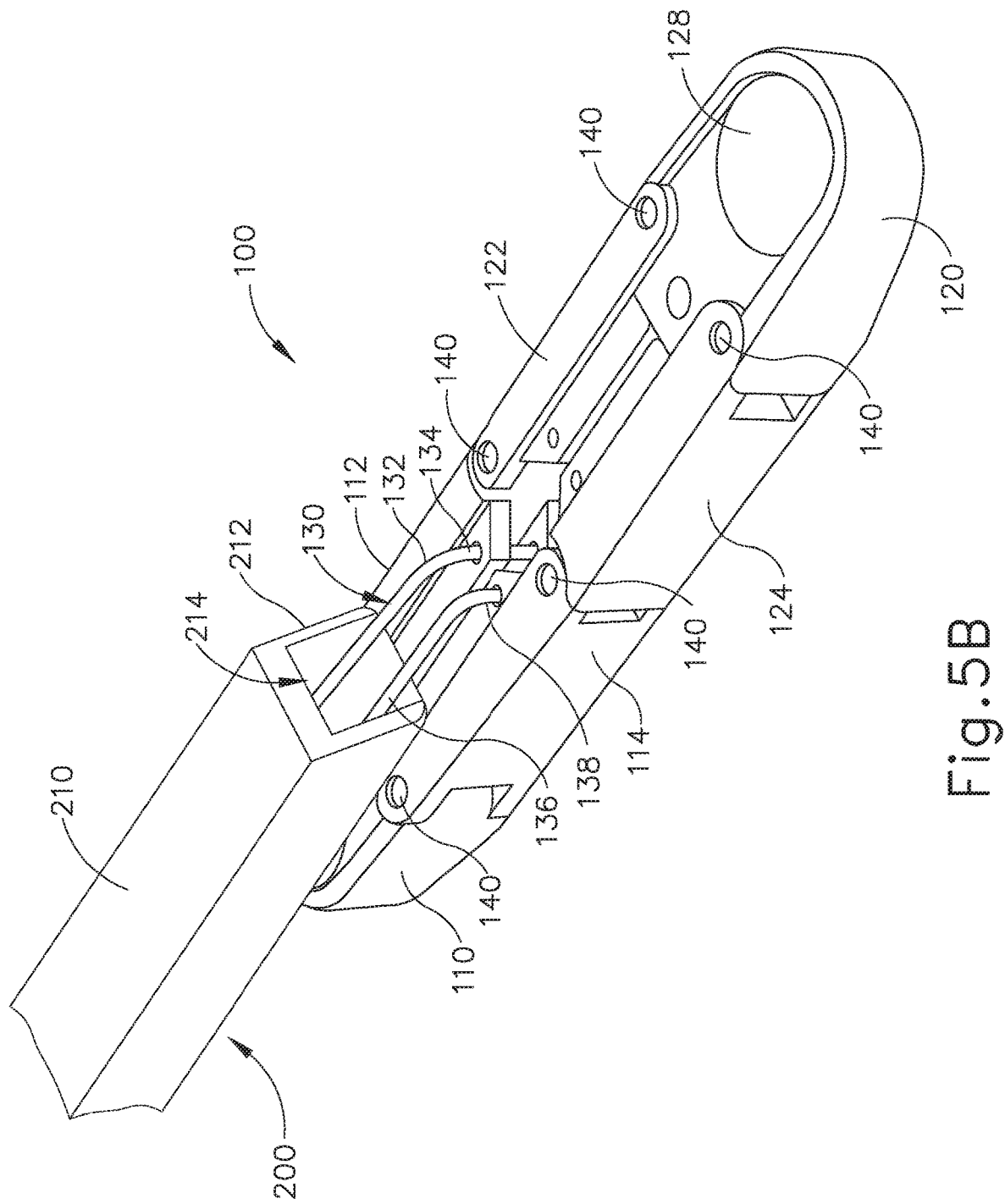
FIG. 5B depicts a perspective view of the instrument of FIG. 4 engaged with the anastomosis compression device of FIG. 3A, with an arm of the instrument in a retracted position.

FIGS. 4-5B show an exemplary instrument (200) that may be used to apply device (100) to an anastomosis site. Instrument (200) of the present example comprises an outer sheath (210) and an inner member (220). Outer sheath (210) has an angled distal end (212) that defines an opening (214). Inner member (220) is slidably disposed in outer sheath (210). Inner member (220) has a distal end (222) that is configured to selectively extend from or retract from opening (214) as inner member (220) is translated relative to sheath (210). Distal end (222) includes a proximally projecting hook member (224) that is configured to engage bend (139) of resilient member (130). The tip (226) of distal end (222) is rounded such that tip (226) is atraumatic in the present example.

As best seen in FIG. 5A, hook member (224) is configured to engage bend (139) of resilient member (130) when inner member (220) is advanced to a distal position where distal end (222) extends from opening (214). When inner member (220) is thereafter retracted relative to outer sheath (210), hook member (224) draws bend (139) and adjacent portions of arms (132, 136) into opening (214), such that bend (139) and adjacent portions of arms (132, 136) are disposed in the interior of sheath (210) as shown in FIG. 5B. The inner sidewalls of sheath (210) that define opening (214) contact arms (132, 136) and prevent arms (132, 136) from pivoting outwardly. Sheath (210) and inner member (220) thus cooperate to hold device (100) in the compressed configuration while inner member (220) is in a retracted position. As will be described in greater detail below, this positioning may be maintained until device (100) is suitably positioned within a bodily lumen (e.g., duodenum, jejunum, ileum, etc.), at which point inner member (220) may be advanced distally relative to sheath (210) to release device (100) at the anastomosis site.

In some exemplary uses, device (100) is first held in the compressed configuration by an operator's hand, by a grasping instrument, or in some other fashion. While device (100) is being so held in the compressed configuration, hook member (224) is moved into position where hook member (224) engages bend (139) as shown in FIG. 5A. Inner member (220) may then be retracted relative to sheath (210), before or after the operator releases their grip on device (100) with their hand, grasping instrument, etc., to the position shown in FIG. 5B. In some other exemplary uses, device (100) is in the expanded configuration when hook member (224) is moved into position to engage bend (139). Once hook member (224) is engaged with bend (139) while device (100) is in the expanded configuration, inner member (220) is retracted relative to outer sheath (210) to the position shown in FIG. 5B. During this retraction, the inner sidewalls of sheath (210) that define opening (214) contact arms (132, 136) and drive arms (132, 136) inwardly, thereby transitioning device (100) from the expanded configuration to the compressed configuration. It should therefore be understood that the operator may use instrument (200) to transition device (100) from the expanded configuration to the compressed configuration and/or some other technique to transition device (100) from the expanded configuration to the compressed configuration.

Various suitable features that may be used to provide selective advancement and retraction of inner member (220) relative to outer sheath (210) will be apparent to those of ordinary skill in the art in view of the teachings herein. It should also be understood that inner member (220) may be resiliently biased relative to outer sheath (210). For instance, inner member (220) may be resiliently biased to proximally retract distal end (222) within outer sheath (210).

Figure 6A:
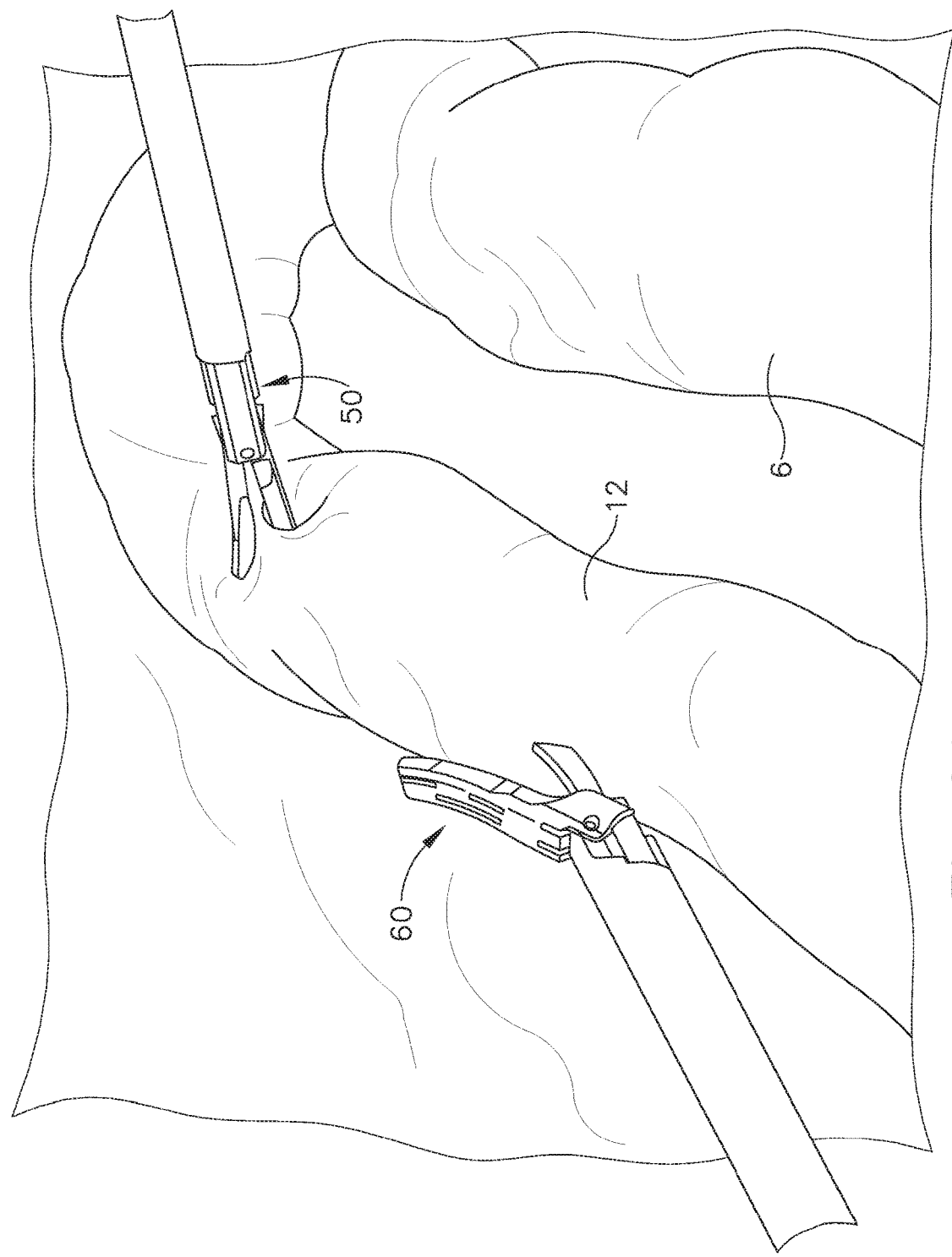
FIG. 6A depicts a perspective view of a patient's digestive system during an anastomosis procedure, with an instrument approaching the patient's duodenum to form an opening.
Figure 6B:
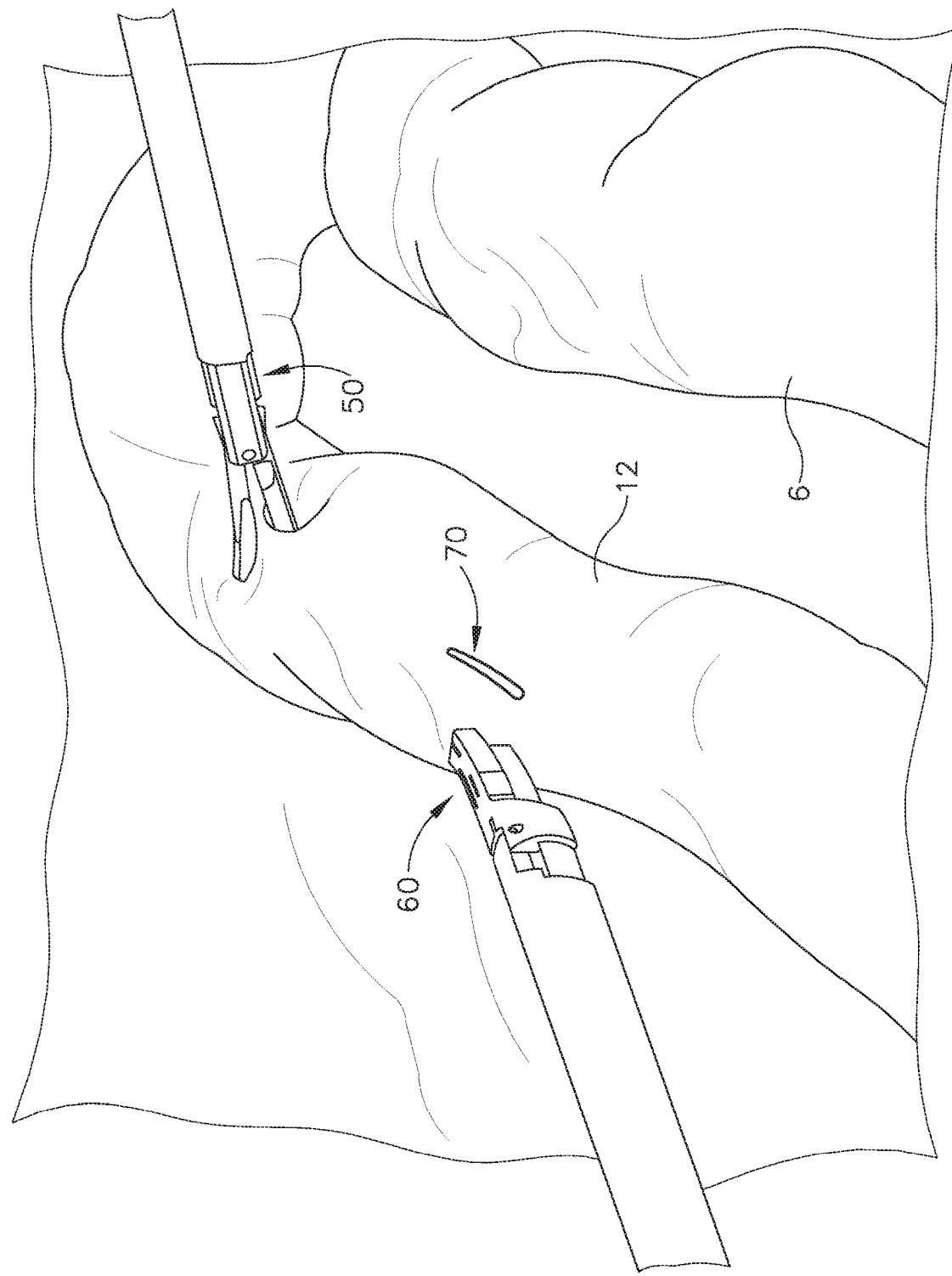
FIG. 6B depicts a perspective view of a patient's digestive system during the anastomosis procedure of FIG. 6A, with the opening formed in the patient's duodenum.
Figure 6C:
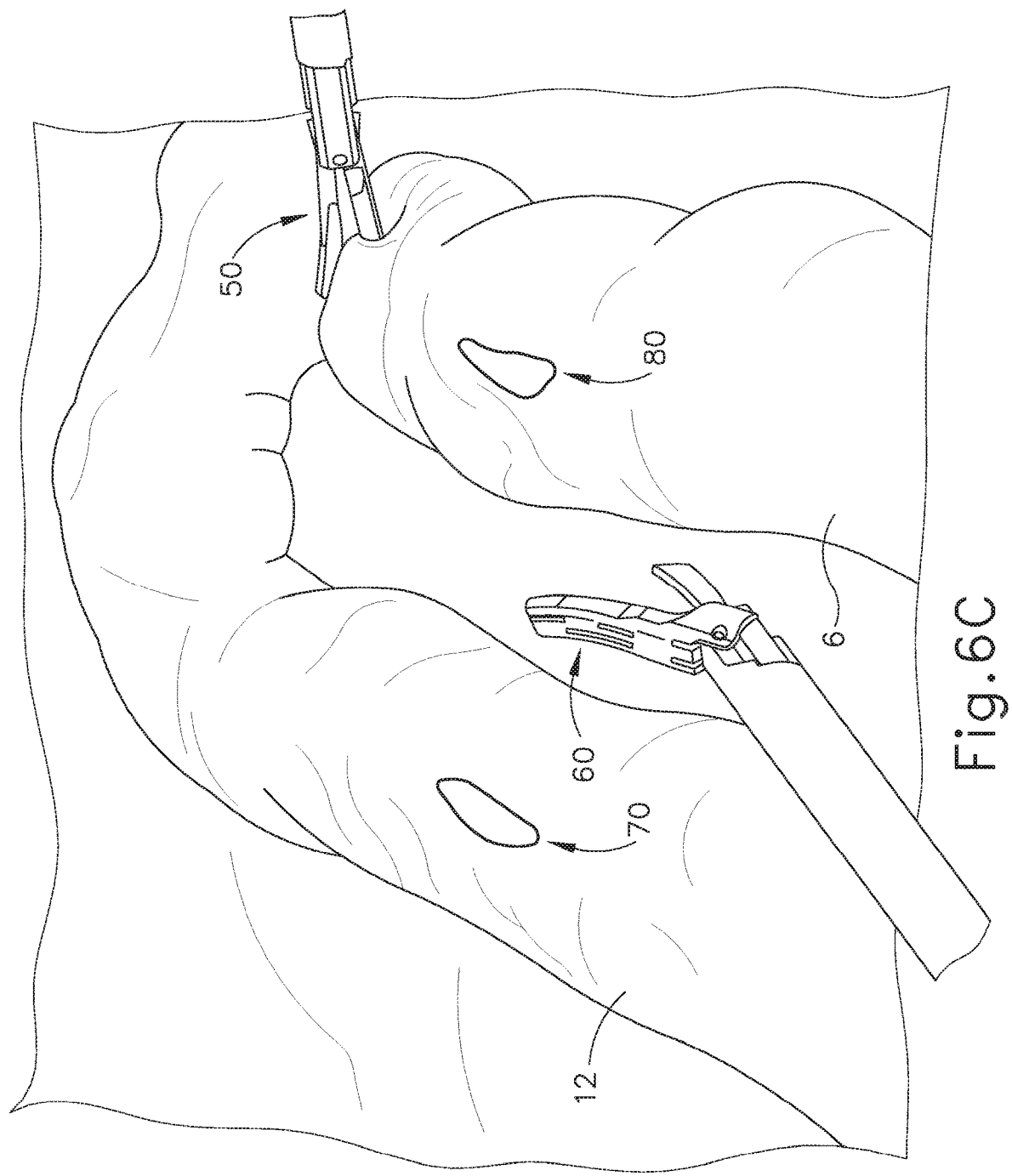
FIG. 6C depicts a perspective view of a patient's digestive system during the anastomosis procedure of FIG. 6A, with an opening formed in the patient's ileum.

C. Exemplary Procedure for Creating an Anastomosis with Folding Anastomosis Compression Device FIGS. 6A-6P show an exemplary procedure in which device (100) and instrument (200) are used in the creation of an anastomosis. In particular, FIG. 6A shows a conventional grasping instrument (50) holding a section of a patient's duodenum (12) while a cutting instrument (60) approaches the duodenum (12). By way of example only, grasping instrument (50) may comprise an ENDOPATH® endoscopic grasping instrument by Ethicon Endo-Surgery, Inc. of Cincinnati, Ohio and/or any other suitable kind of grasping instrument. By way of further example only, cutting instrument (60) may comprise an ultrasonic surgical instrument such as the HARMONIC ACE® shears by Ethicon Endo-Surgery, Inc. of Cincinnati, Ohio and/or any other suitable kind of instrument. While grasping instrument (50) holds the duodenum (12), cutting instrument (60) is used to create an enterotomy (70) in the duodenum (12) as shown in FIG. 6B. Grasping instrument (50) is then used to hold the patient's ileum (6) while cutting instrument (60) is used to create an enterotomy (80) in the ileum (6) as shown in FIG. 6C.

Figure 6D:
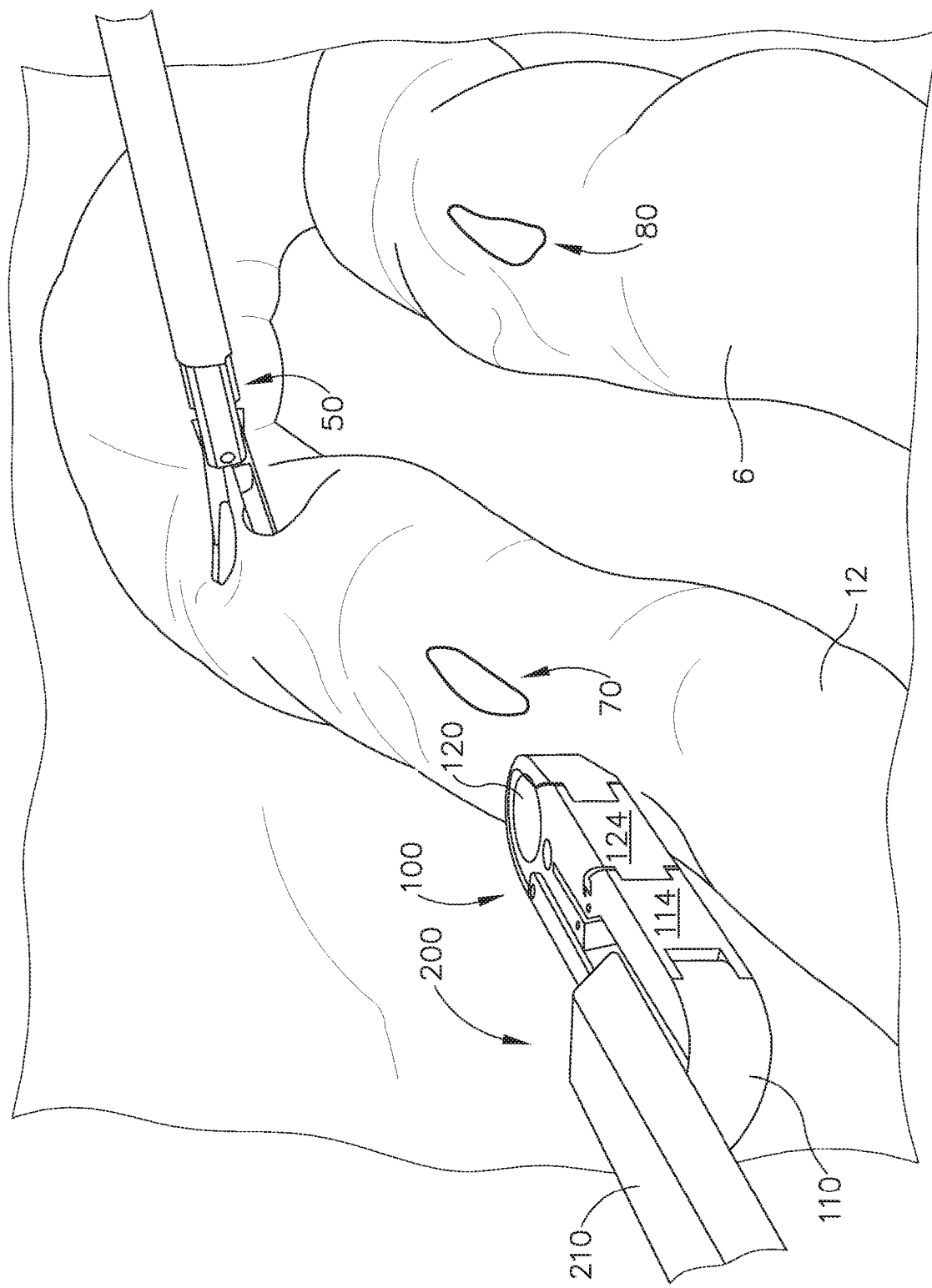
FIG. 6D depicts a perspective view of a patient's digestive system during the anastomosis procedure of FIG. 6A, with the instrument of FIG. 4 and the anastomosis compression device of FIG. 3A approaching the opening in the patient's duodenum.
Figure 6E:
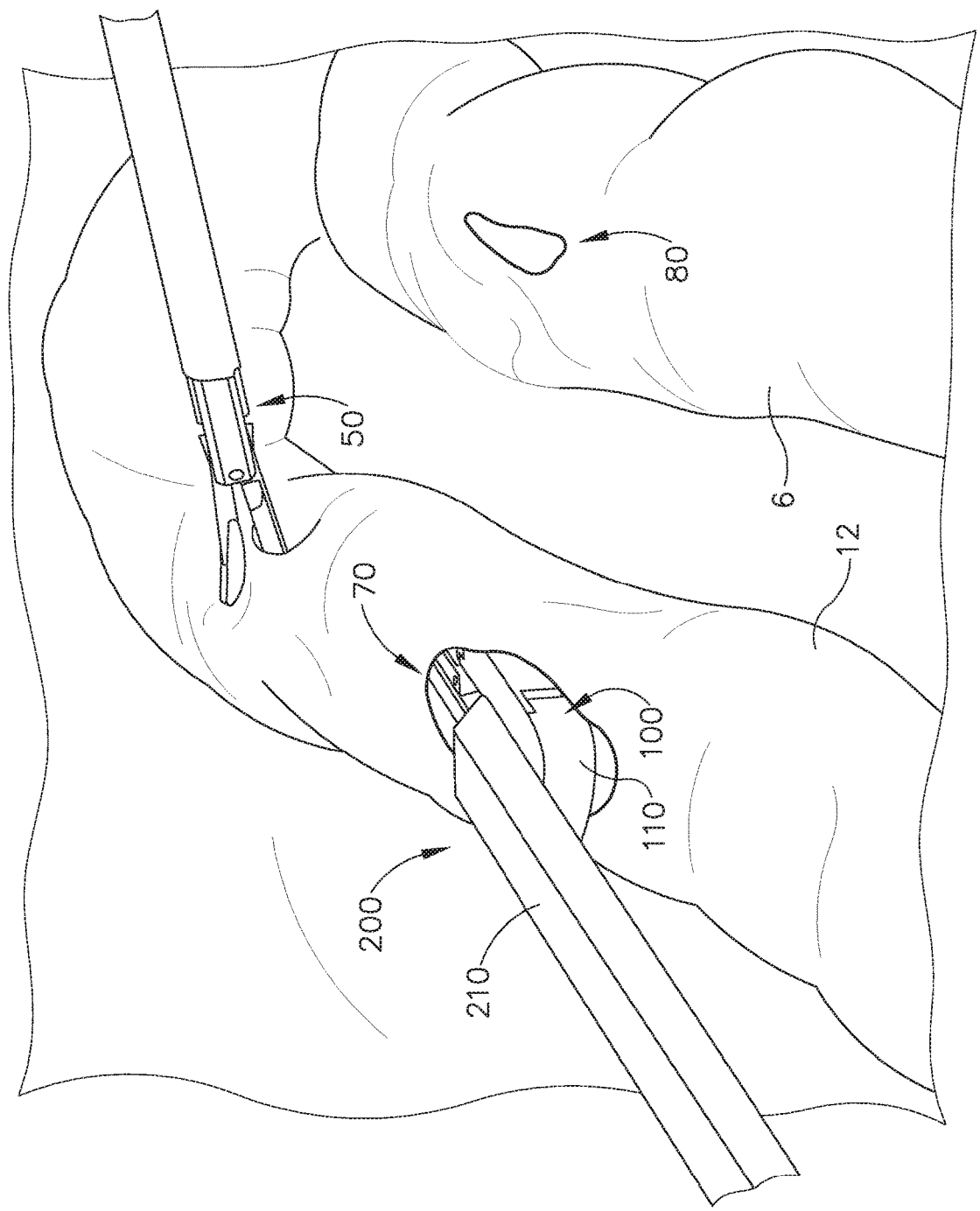
FIG. 6E depicts a perspective view of a patient's digestive system during the anastomosis procedure of FIG. 6A, with the anastomosis compression device of FIG. 3A being inserted in the opening in the patient's duodenum.
Figure 6F:
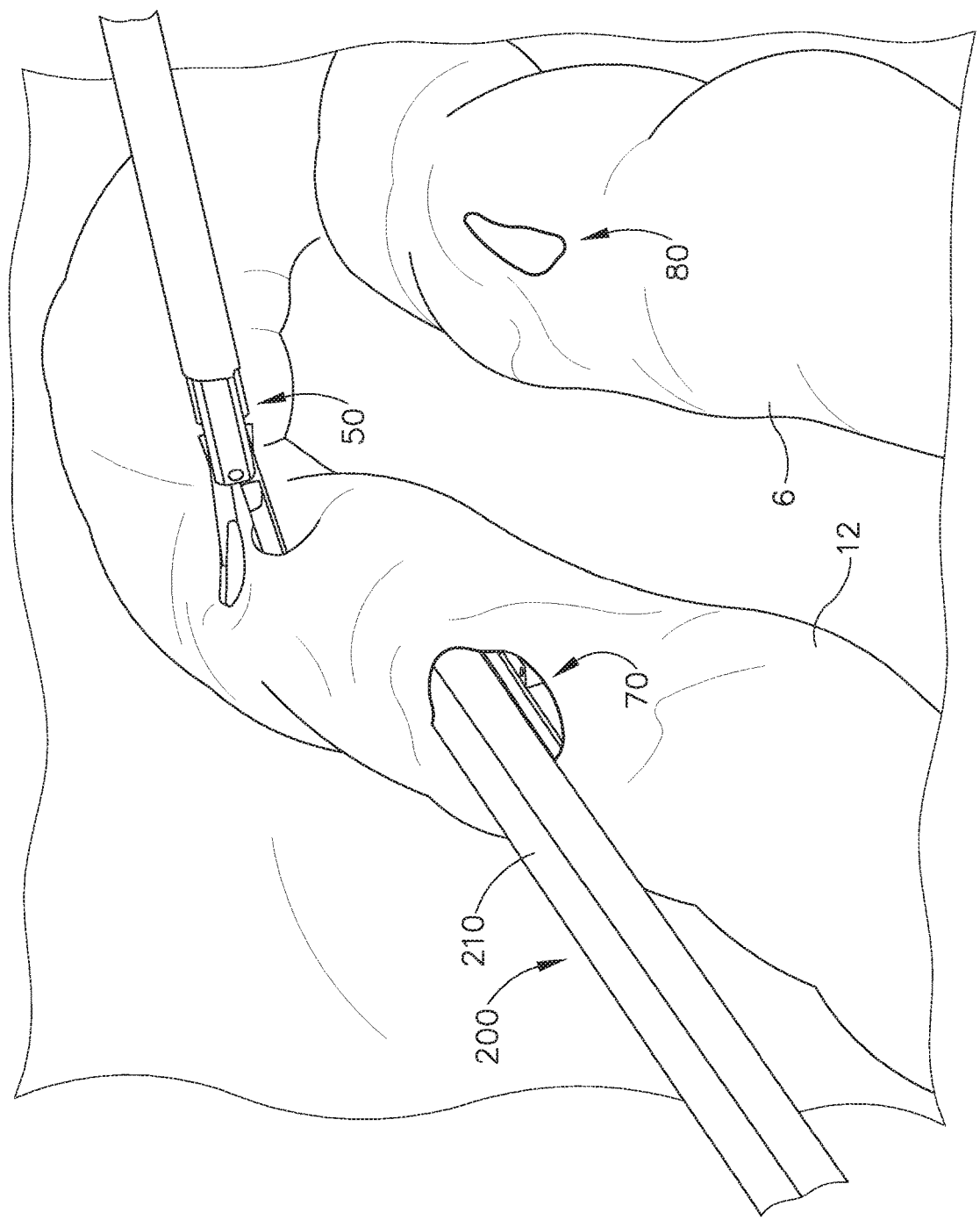
FIG. 6F depicts a perspective view of a patient's digestive system during the anastomosis procedure of FIG. 6A, with the anastomosis compression device of FIG. 3A fully inserted in the opening in the patient's duodenum.

After enterotomies (70, 80) have been created, an instrument (200) with a preloaded compression device (100) is introduced as shown in FIG. 6D. While grasping device (50) holds the duodenum (12), instrument (200) is used to insert device (100) through enterotomy (70) as shown in FIG. 6E. As can be seen, second end member (120) of device (100) passes through enterotomy (70) first. Instrument (200) continues to advance into enterotomy (70) to position the entirety of device (100) in the lumen of the duodenum (12), as shown in FIG. 6F. It should be understood that device (100) is in the compressed or collapsed configuration during the entire time that device (100) is inserted through enterotomy (70). It should also be understood that this compressed or collapsed configuration of device (100) may minimize stretching or tearing of enterotomy (70) during passage of device (100) through enterotomy (70).

Figure 6G:
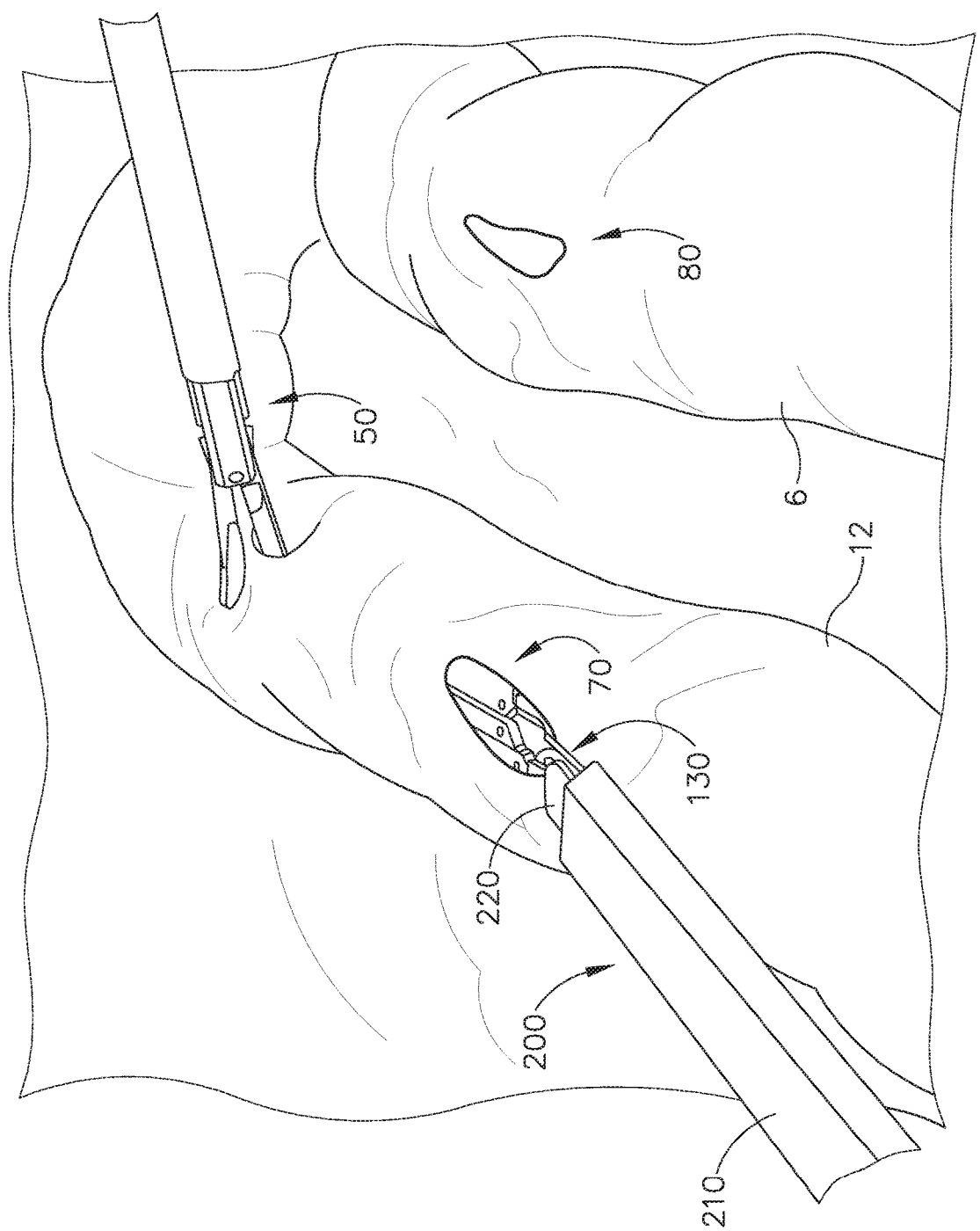
FIG. 6G depicts a perspective view of a patient's digestive system during the anastomosis procedure of FIG. 6A, with a retention feature of the anastomosis compression device of FIG. 3A being positioned outside the opening in the patient's duodenum.
Figure 6H:
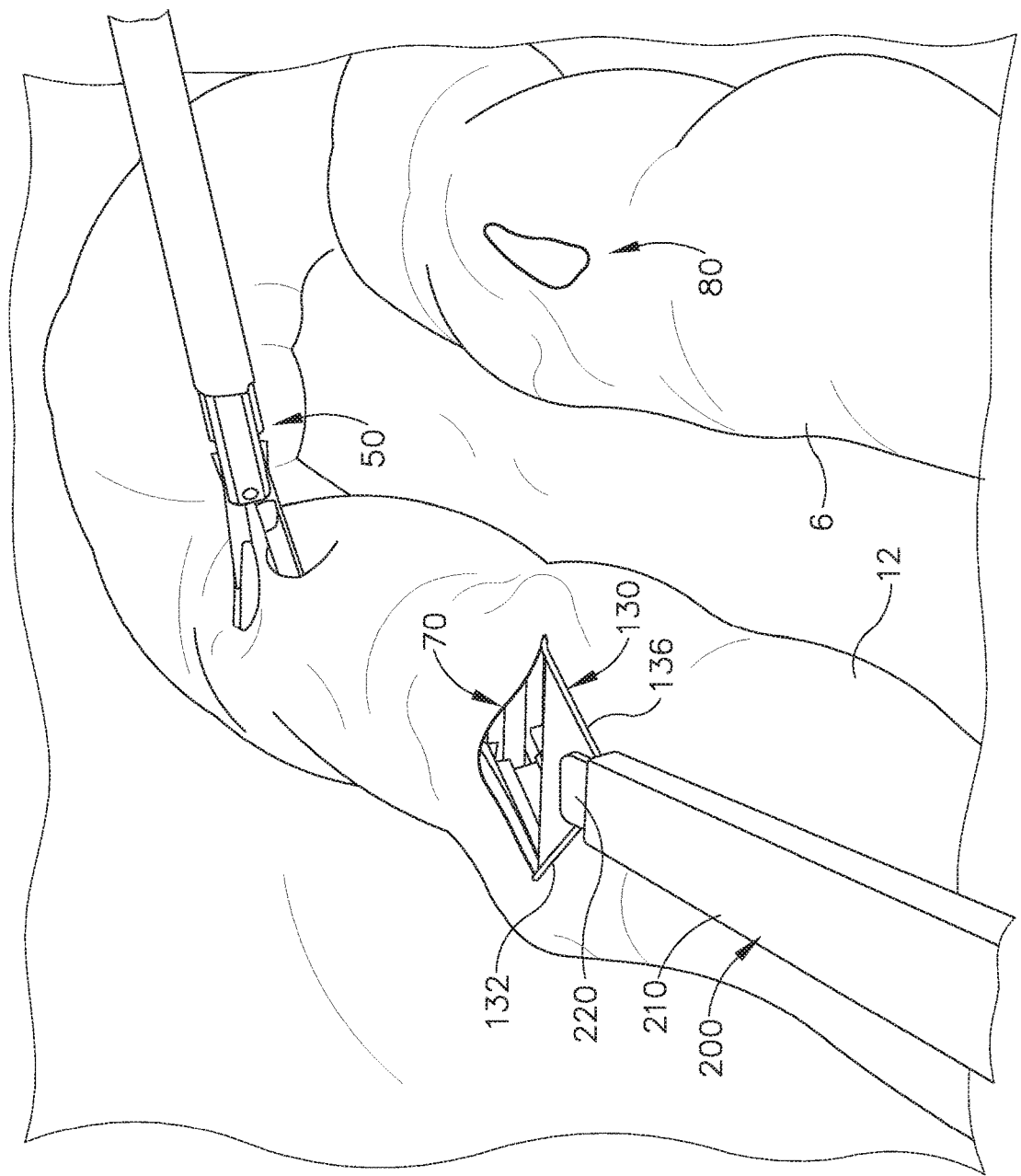
FIG. 6H depicts a perspective view of a patient's digestive system during the anastomosis procedure of FIG. 6A, with the anastomosis compression device of FIG. 3A being released to expand within the patient's duodenum.
Figure 61:
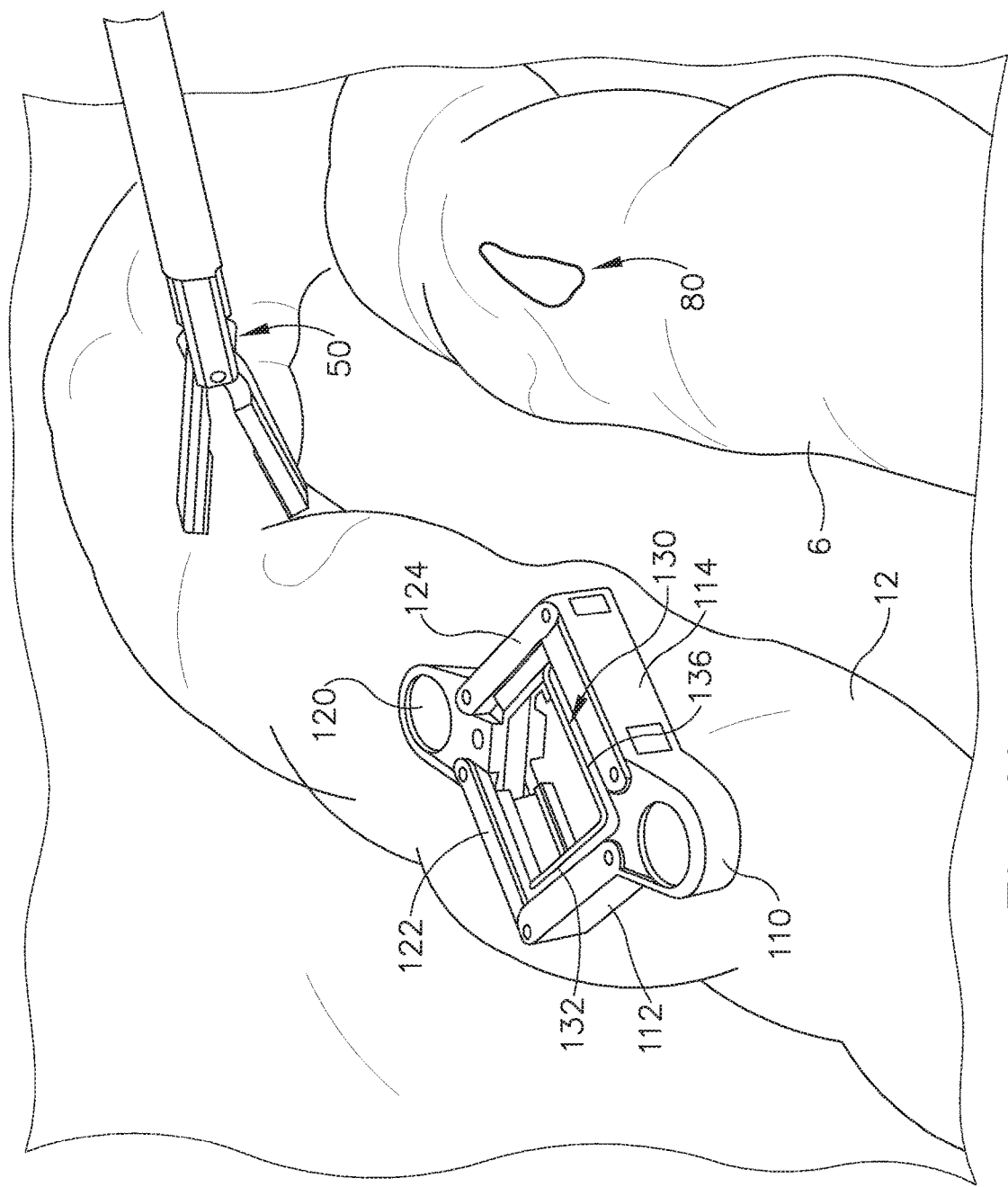

After device (100) has been fully inserted through enterotomy (70), instrument (200) is retracted from enterotomy (70). During this retraction, hook member (224) remains engaged with bend (139) of resilient member (130). In particular, and as shown in FIG. 6G, instrument (200) is angled during retraction such that first end member (110) of device catches on the interior surface of the duodenum (12), and such that resilient member (130) pivots away from links (112, 114) to enable bend (139) and adjacent portions of arms (132, 136) to pass back out of enterotomy (70) while the rest of device (100) remains in the duodenum (12). With hook member (224) still engaged with bend (139) of resilient member (130), inner member (220) is advanced distally relative to outer sheath (210), to a point where resilient member (130) is eventually positioned distal to opening (214) of sheath (210). Once resilient member (130) clears sheath (210), the resilient bias of resilient member (130) drives arms (132, 136) outwardly, thereby transitioning device (100) to the expanded state as shown in FIG. 6H. Instrument (200) is further manipulated and/or lifted away from the tissue surface to disengage resilient member (130) from hook member (224), and instrument (200) is then retracted as shown in FIG. 6I.

As can be seen in FIGS. 6H-6I, resilient member (130) captures tissue between resilient member (130) and the assembly formed by first end member (110) and links (112, 114). The resilient bias of resilient member (130) toward the assembly formed by first end member (110) and links (112, 114) provides a sustained grip on the tissue. This grip on the tissue assists in maintaining the position of device (100) in the duodenum (12). As can also be seen in FIGS. 6H-6L the expansion of device (100) in the duodenum (12) holds enterotomy (70) in an open state, which thereby maintains patency through enterotomy (70) as will be described in greater detail below. In the present example, the distance between the exterior of the joint formed by links (112, 122) and the exterior of the joint formed by links (114, 124) is approximately 2.6 cm; while the distance between the interior of the joint formed by links (112, 122) and the interior of the joint formed by links (114, 124) is approximately 1.5 cm. Of course, any other suitable dimensions may be provided.

Figure 6J:
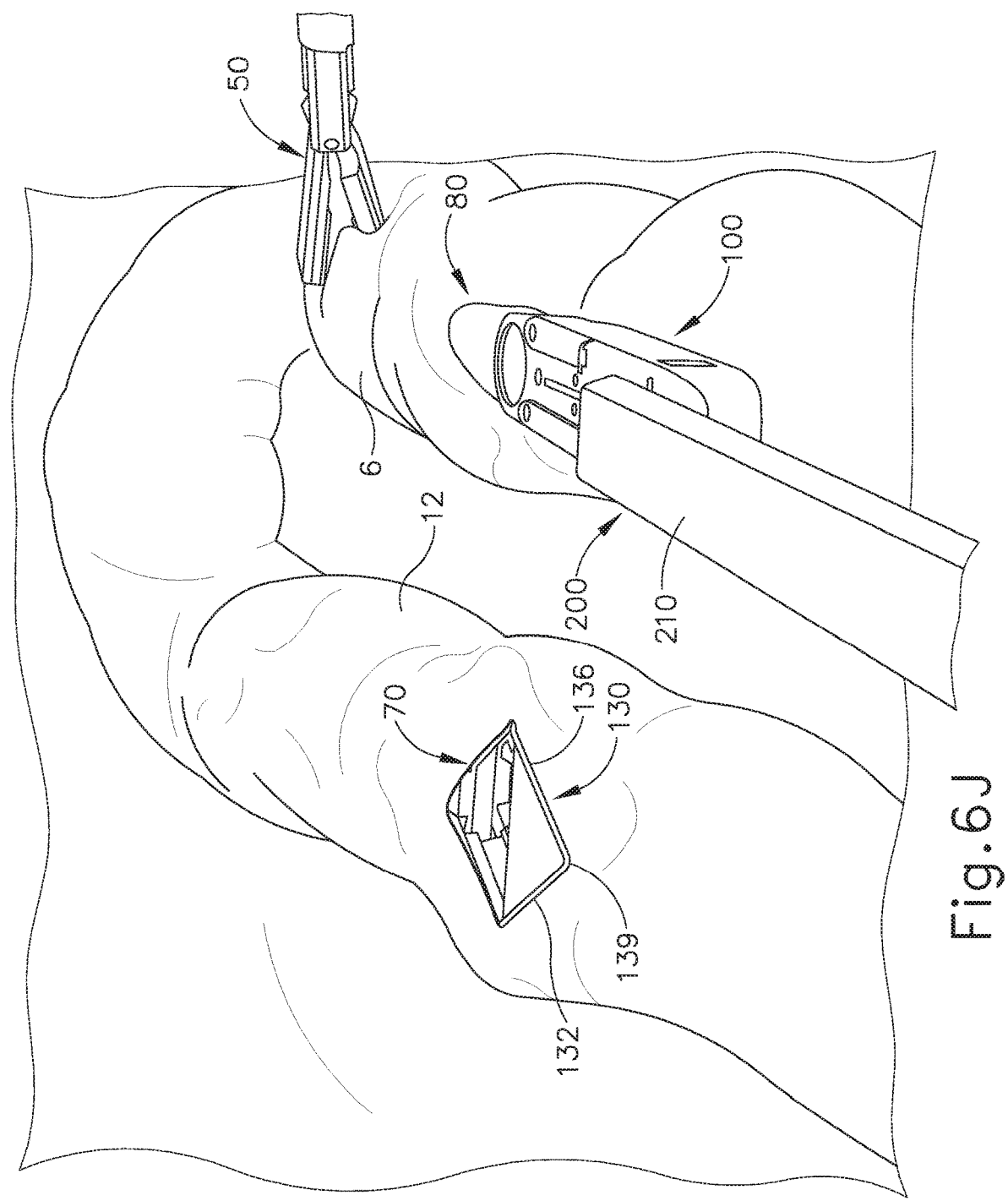
FIG. 6J depicts a perspective view of a patient's digestive system during the anastomosis procedure of FIG. 6A, with the instrument of FIG. 4 and the anastomosis compression device of FIG. 3A approaching the opening in the patient's ileum.
Figure 6K:
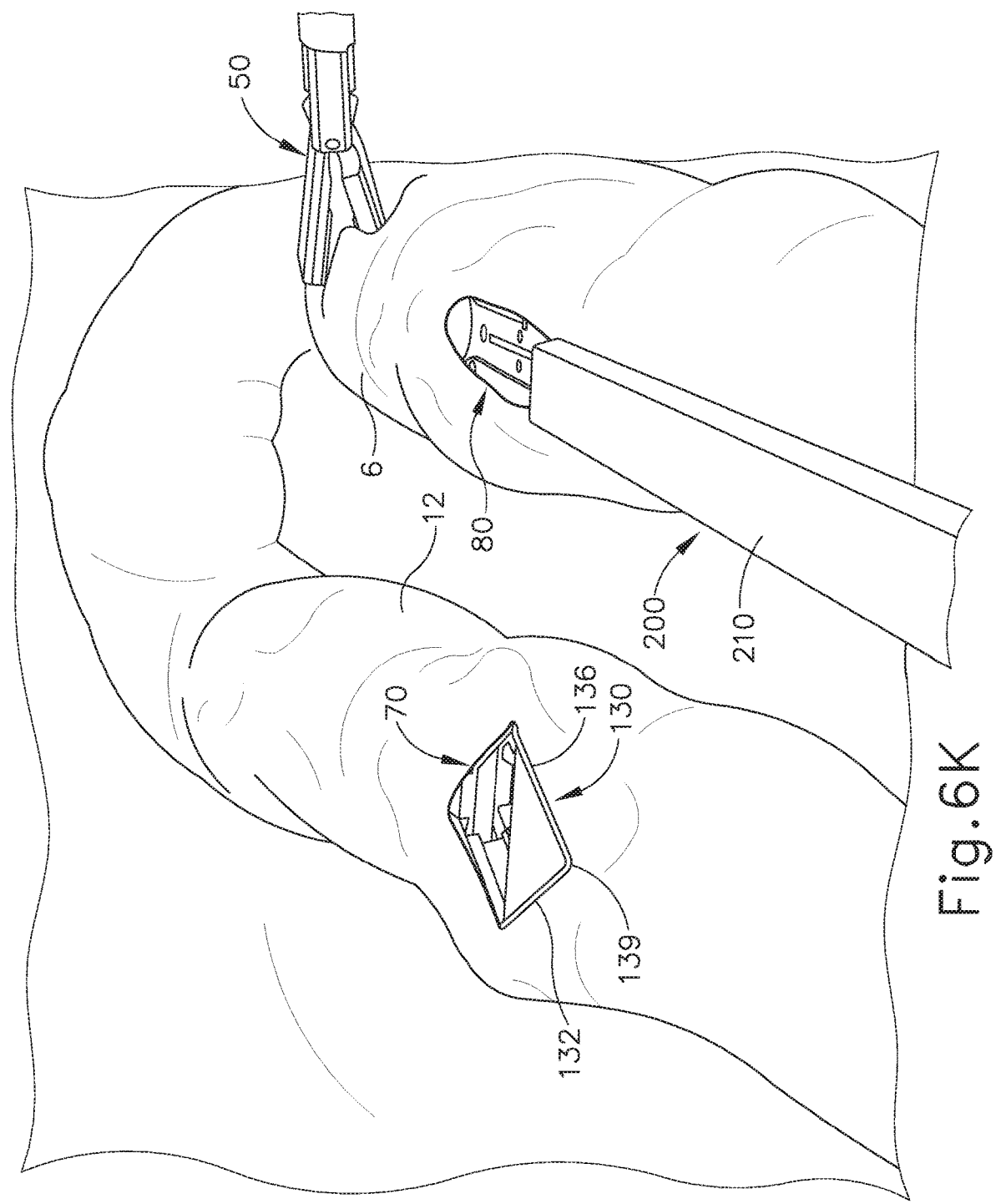
FIG. 6K depicts a perspective view of a patient's digestive system during the anastomosis procedure of FIG. 6A, with the anastomosis compression device of FIG. 3A fully inserted in the opening in the patient's ileum.
Figure 6L:
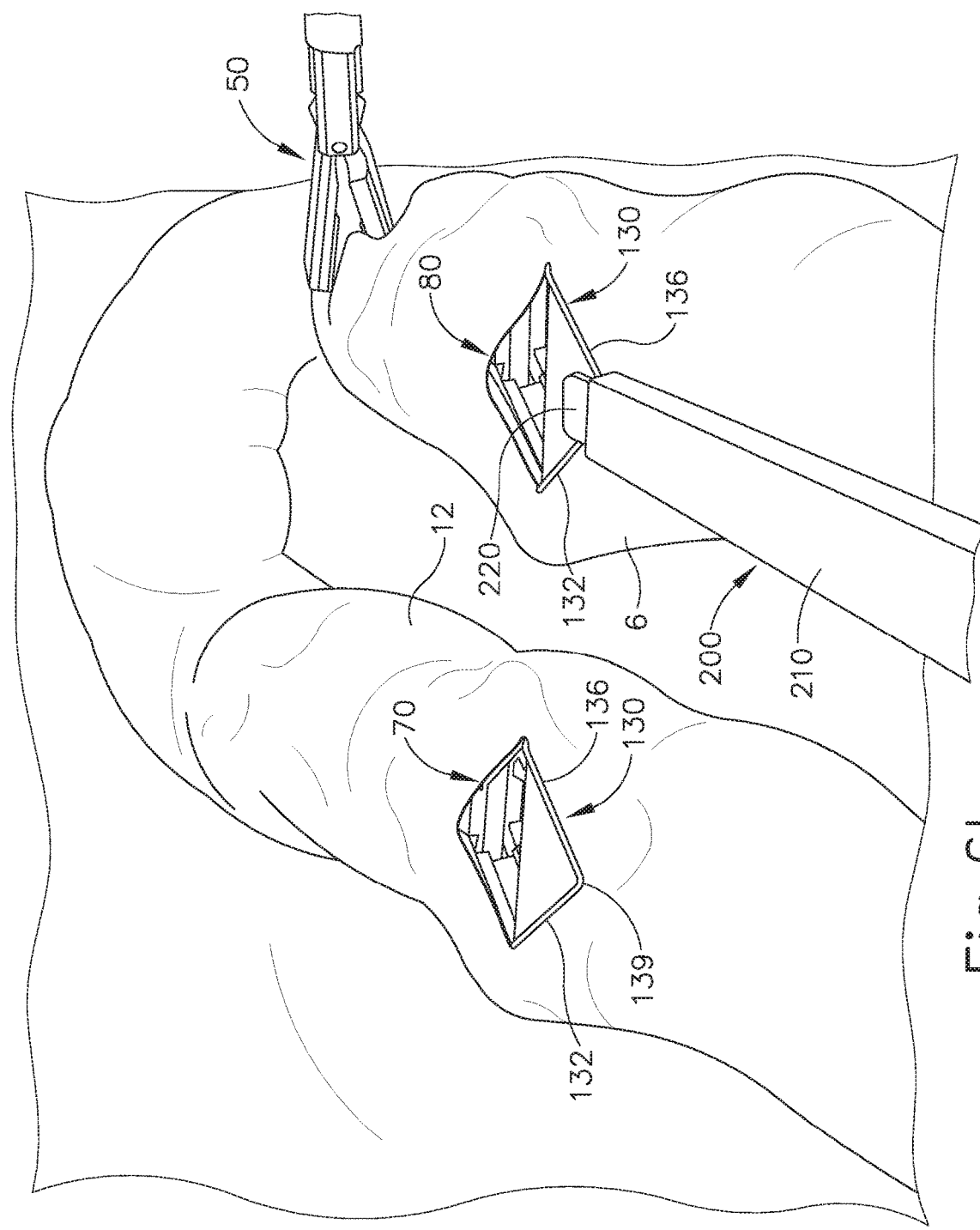
FIG. 6L depicts a perspective view of a patient's digestive system during the anastomosis procedure of FIG. 6A, with the anastomosis compression device of FIG. 3A being released to expand within the patient's ileum.

Once device (100) has been applied to the duodenum (12), another device (100) is applied to the ileum (6) in a similar fashion. In particular, instrument (200) is used to position another device (100) in relation to enterotomy (80), while grasping device (50) holds the ileum (6), as shown in FIG. 6J. This second device (100) is then inserted into enterotomy (80) as shown in FIG. 6K. Instrument (200) is then manipulated to position resilient member (130) outside enterotomy (80) while the rest of device (100) remains within the ileum (6), and the inner member (220) of instrument (200) is advanced distally relative to sheath (210) to enable expansion of device (100) as shown in FIG. 6L. Device (100) is then released from instrument (200), leaving the second device (100) deployed in the ileum (6) as shown in FIG. 6M.

As with device (100) in the duodenum (12), resilient member (130) of device (100) in the ileum (6) captures tissue between resilient member (130) and the assembly formed by first end member (110) and links (112, 114). The resilient bias of resilient member (130) toward the assembly formed by first end member (110) and links (112, 114) provides a sustained grip on the tissue. This grip on the tissue assists in maintaining the position of device (100) in the ileum (6). As can also be seen in FIG. 6M, the expansion of device (100) in the ileum (6) holds enterotomy (80) in an open state, which thereby maintains patency through enterotomy (80) as will be described in greater detail below.

Figure 6N:
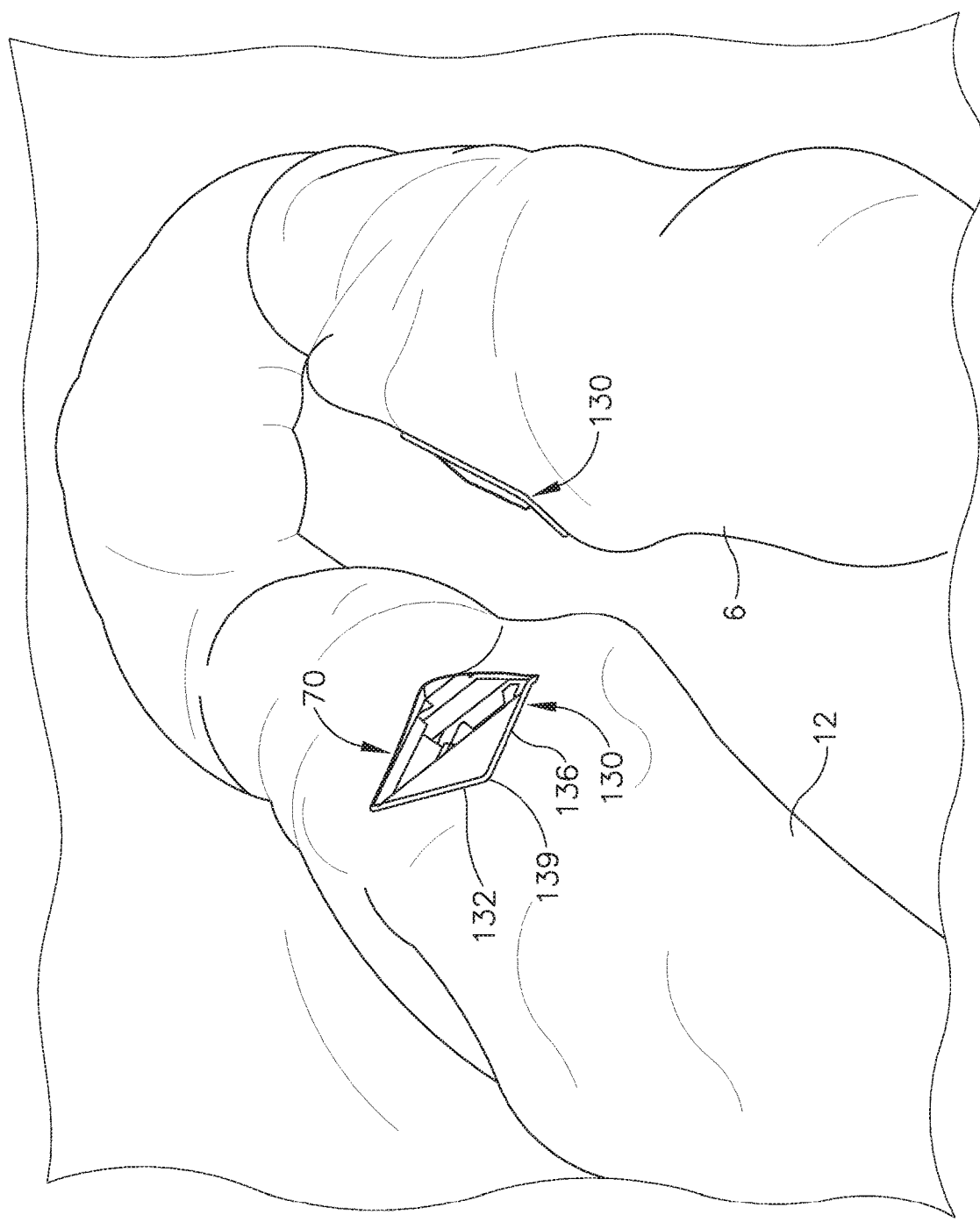
FIG. 6N depicts a perspective view of a patient's digestive system during the anastomosis procedure of FIG. 6A, with the anastomosis compression devices being urged toward each other to thereby urge the duodenum and the ileum toward each other.
Figure 60:
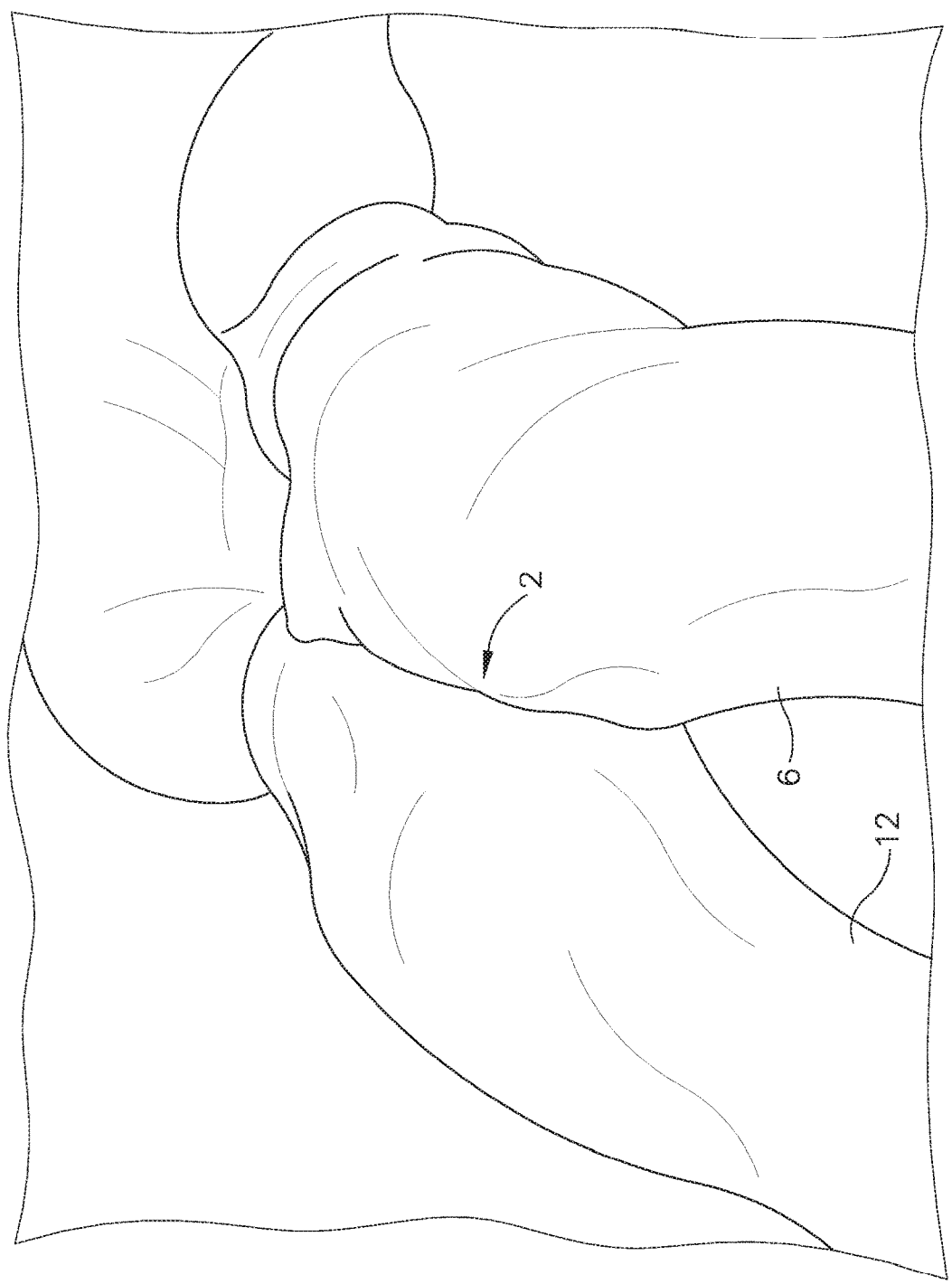
Figure 6P:
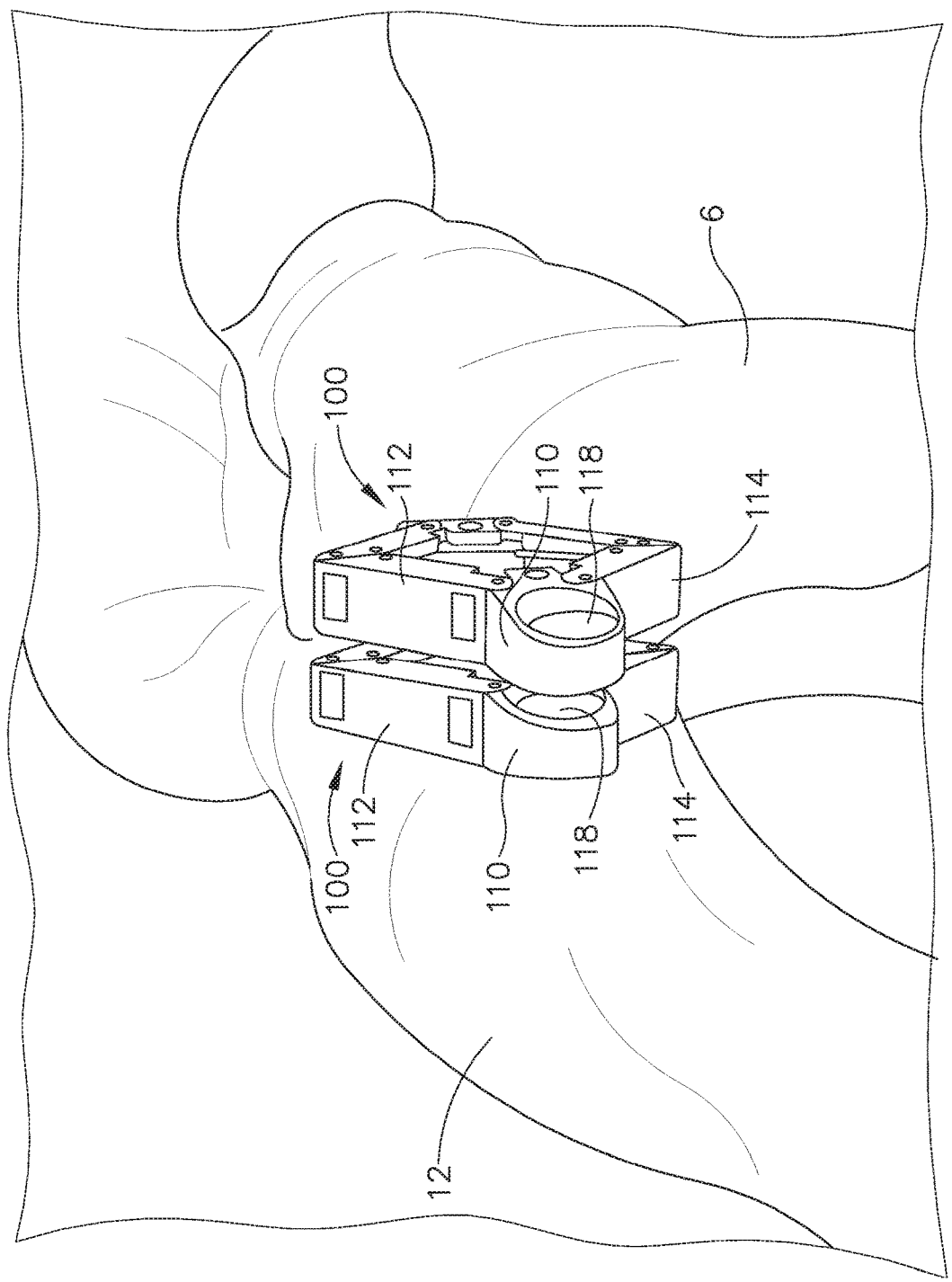
FIG. 6P depicts a perspective view of a patient's digestive system during the anastomosis procedure of FIG. 6A, with portions of tissue omitted to show the anastomosis compression devices in position to hold the openings in the duodenum and ileum together to form an anastomosis.

After devices (100) are fully deployed in the duodenum (12) and the ileum (6), devices (100) are urged toward each other as shown in FIG. 6N. This urging continues until the duodenum (12) and the ileum (6) come in contact with each other at the regions associated with devices (100), as shown in FIG. 6O. As shown in FIG. 6P, with the duodenum (12) and the ileum (6) so positioned, devices (100) are parallel with each other and are positioned such that enterotomies (70, 80) are aligned with each other to form an anastomosis (2). This alignment of devices (100) and enterotomies (70, 80) is promoted by magnets (118, 128) of devices (100). Magnets (118) also secure the positioning of devices (100) in relation to each other. In particular, magnet (118) of the first device (100) is attracted to magnet (118) of the second device (100); while magnet (128) of the first device (100) is attracted to magnet (128) of the second device (100). Magnets (118) thus remain in coaxial alignment with each other and magnets (128) remain in coaxial alignment with each other. The magnetic fields of magnets (118, 128) and the forces generated thereby are sufficient to hold devices (100) in place even as digestion later occurs in the patient. In other words, devices (100) remain in place even during peristalsis in the duodenum (12) and in the ileum (6). By way of example only, magnets (118, 128) may comprise part number D44-N52 from K&J Magnetics of Jamison, Pa. It should also be understood that the forces generated by the magnetic fields of magnets (118, 128) will substantially compress the tissue of the duodenum (12) and ileum (6) that is captured between the devices (100). The ultimate results of such compression will be described in greater detail below.

As noted above, magnets (118, 128) provide alignment of devices (100) and also secure the positions of devices (100) within the duodenum (12) and the ileum (6). It should be understood that devices (100) may include other features, in addition to or in lieu of magnets (118, 128), that promote alignment of devices (100) and secure the positions of devices (100) within the duodenum (12) and the ileum (6). For instance, devices (100) may include complementary nesting features such as projections and pockets, alternating undulations, retractable constant force springs, resilient clips, etc. Other suitable features that may be used to promote alignment of devices (100) and/or secure the positions of devices (100) within the duodenum (12) and the ileum (6) will be apparent to those of ordinary skill in the art in view of the teachings herein.

It should be understood that the procedure described above may be performed in a minimally invasive fashion, with devices (100), instruments (50, 60, 200), and any other necessary instrumentation being inserted through trocars or small incisions. It should also be recognized that the only enterotomies (70, 80) created in the gastrointestinal tract are joined together to form an anastomosis (2). Thus, there is no need to create any additional enterotomies in order to position any devices or instrumentation; and no need to close any such additional enterotomies.

In the example described above and shown in the FIG. 6 series, devices (100) are oriented such that resilient members (130) are both oriented in the same direction, with both bends (139) pointing proximally. In some other versions, devices (100) are applied at orientations such that resilient members (130) are oriented in opposite directions. For instance, device (100) in the duodenum (12) may be oriented such that bend (139) of resilient member (130) of device (100) applied in the duodenum (12) points proximally; while device (100) in the ileum (6) is oriented such that bend (139) of resilient member (130) of device (100) applied in the ileum (6) points distally.

Figure 7A:
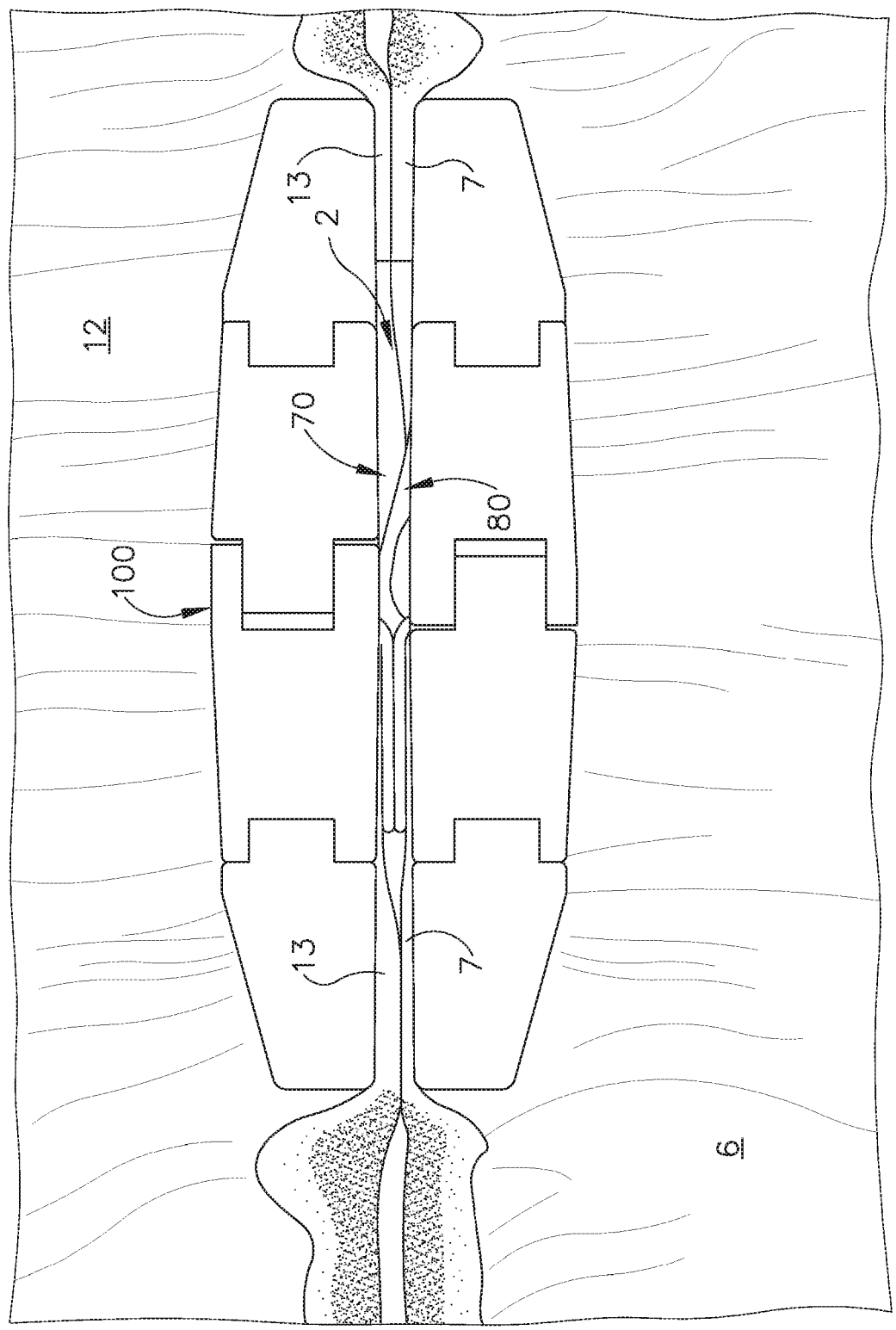
FIG. 7A depicts a cross-sectional view of a pair of the anastomosis compression devices of FIG. 3A opposingly positioned in a patient's duodenum and ileum, with live tissue positioned between opposing surfaces of the anastomosis compression devices.
Figure 7B:
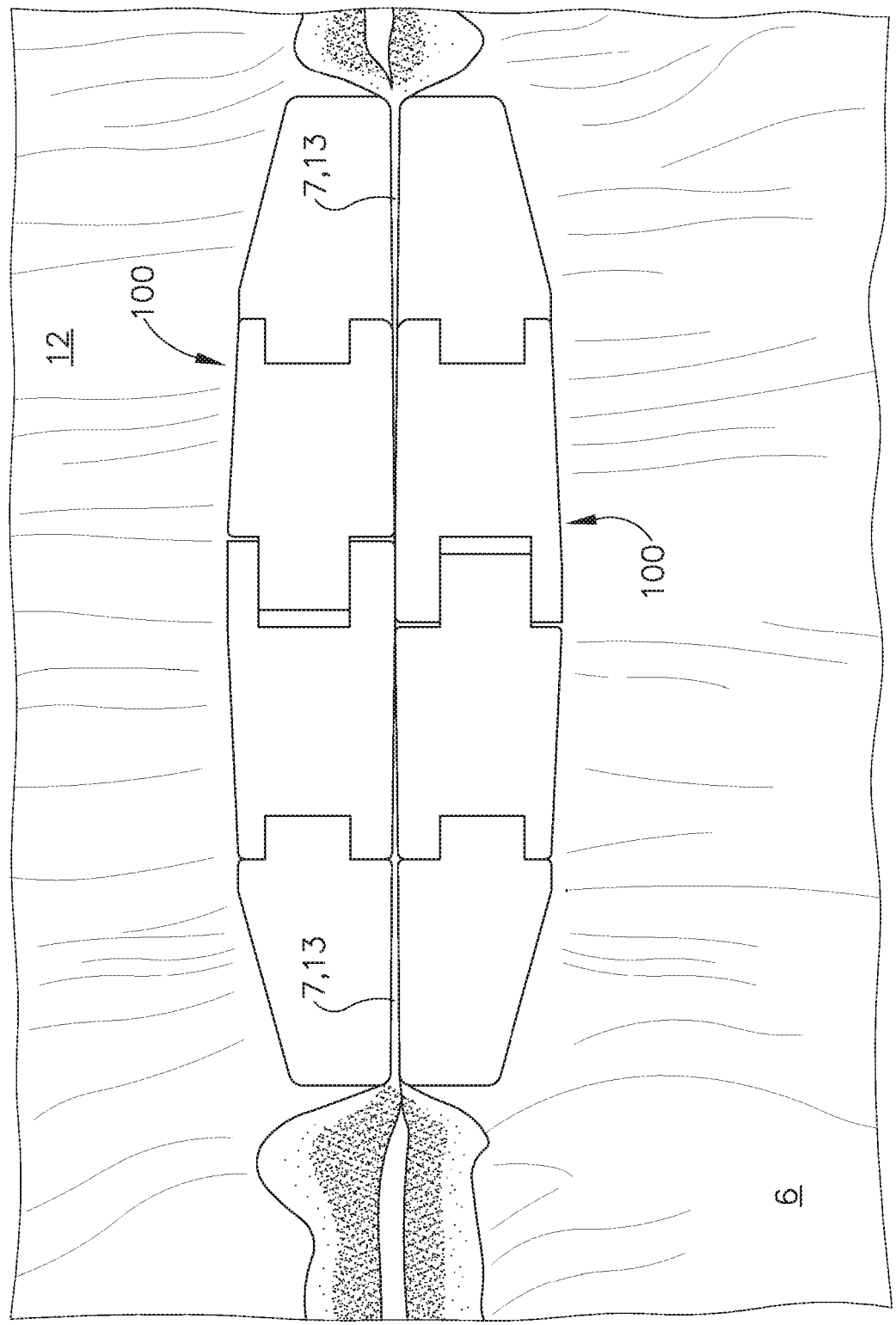
FIG. 7B depicts a cross-sectional view of a pair of the anastomosis compression devices of FIG. 3A opposingly positioned in a patient's duodenum and ileum, with the tissue positioned between opposing surfaces of the anastomosis compression devices in a state of necrosis.
Figure 7C:
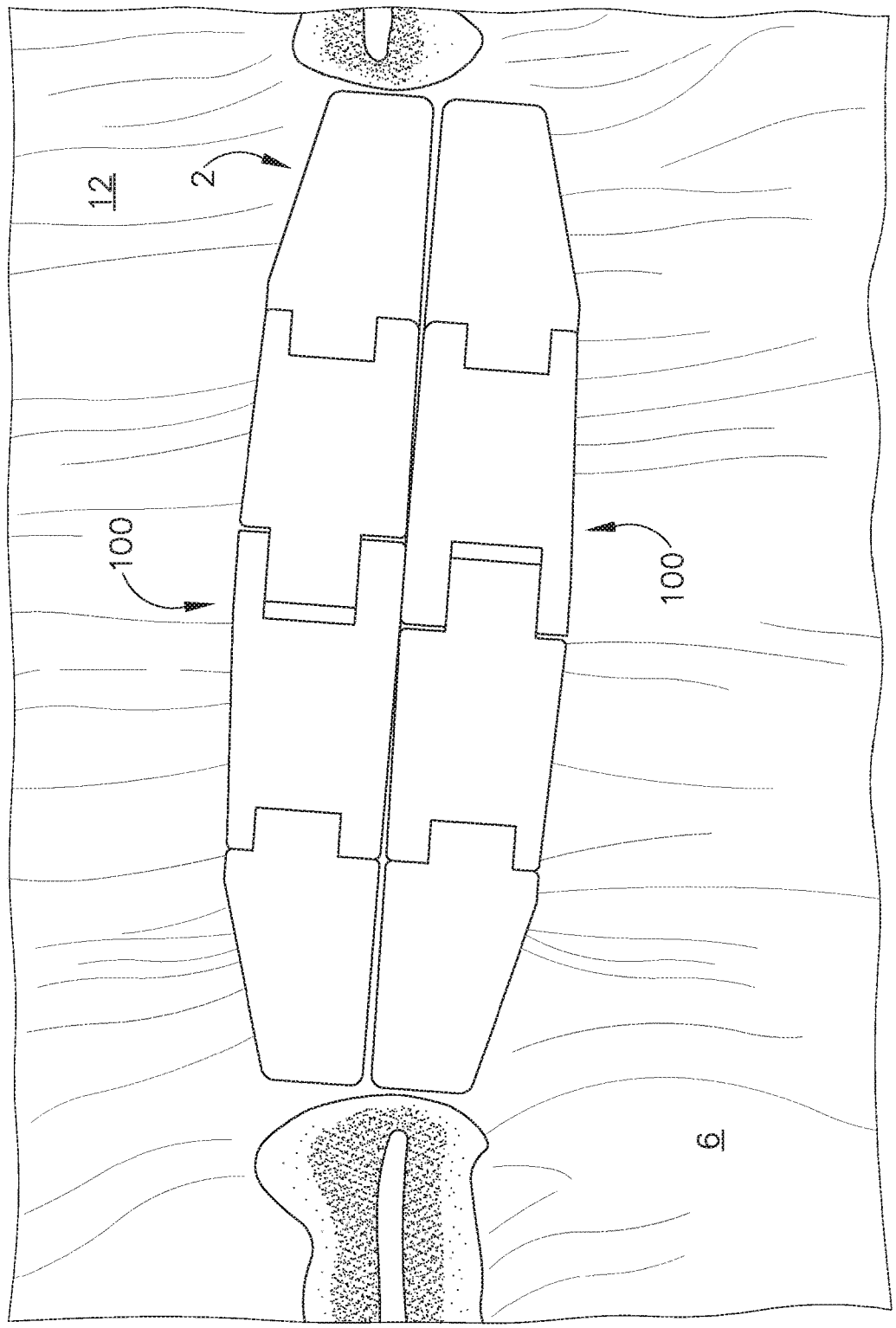
FIG. 7C depicts a cross-sectional view of a pair of the anastomosis compression devices of FIG. 3A, with the anastomosis compression devices beginning to leave the anastomosis formed between the patient's duodenum and ileum.
Figure 7D:
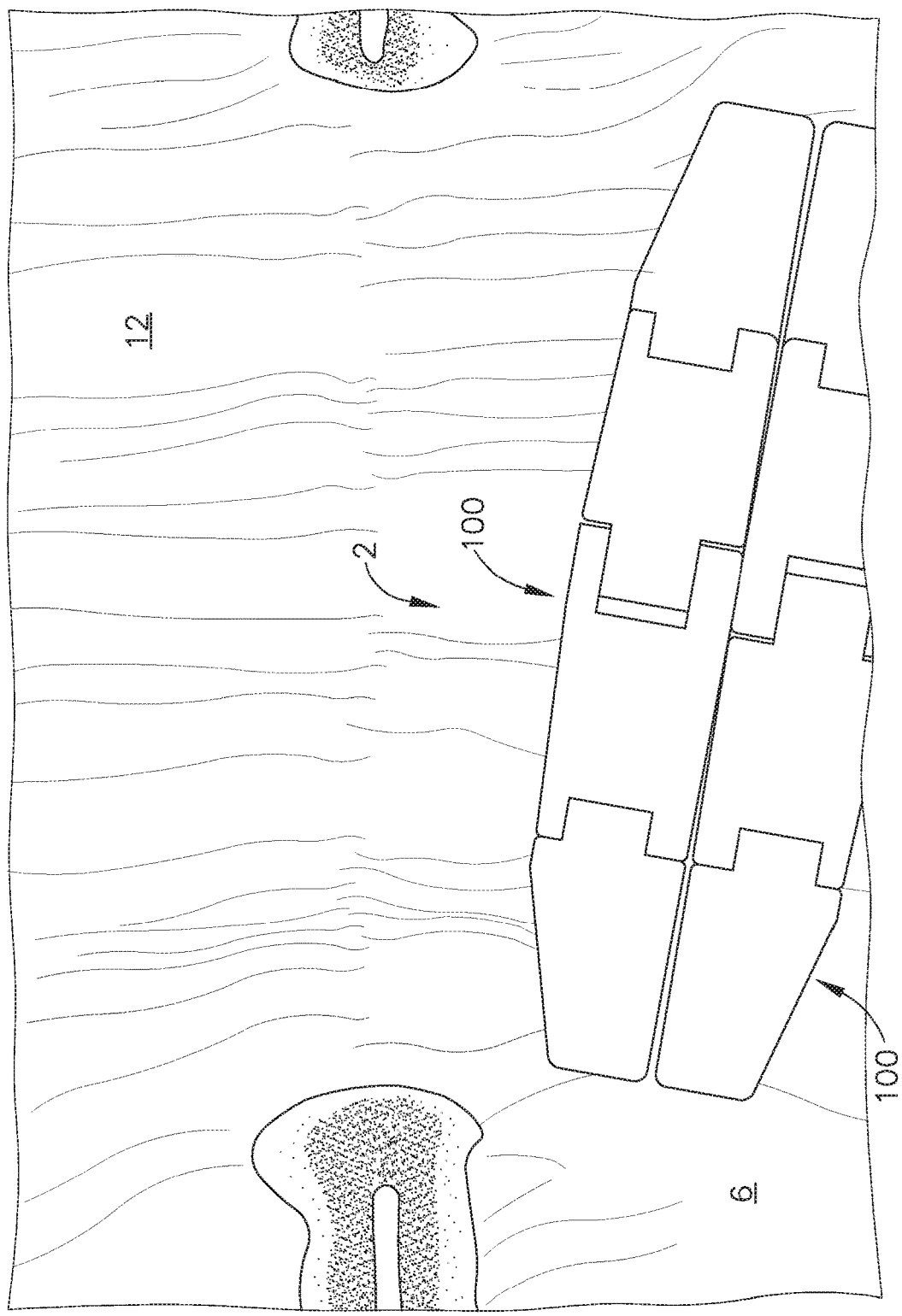
FIG. 7D depicts a cross-sectional view of a pair of the anastomosis compression devices of FIG. 3A, with the anastomosis compression devices passing into the patient's ileum.

FIGS. 7A-7E show the site of the anastomosis (2) after devices (100) have been fully deployed. In particular, FIG. 7A shows devices (100), the duodenum (12), and the ileum (6) at the stage shown in FIGS. 6O-6P, just after deployment. As shown, tissue (13) of the duodenum (12) and tissue (7) of the ileum (6) is being compressed between devices (100). Over a period of time, the ischemia caused by this compression of tissue (7, 13) eventually results in necrosis of the tissue (7, 13), as shown in FIG. 7B. This necrosis eventually reaches a point where the tissue (7, 13) can no longer structurally support devices (100), such that devices (100) break free from the site of the anastomosis (2) as shown in FIG. 7C. Devices (100) remain held together due to the attraction between magnets (118, 128) and pass into the ileum (6) as shown in FIG. 7D, eventually passing into the bowels and out from the patient with feces. In some instances, some necrosed tissue (7, 13) may remain captured between devices (100). It should be understood that the size of the fluid passageway at the site of the anastomosis (2) may initially be the size of the stretched enterotomies (70, 80) when devices (100) are first applied and secured relative to each other. However, the size of the fluid passageway at the site of the anastomosis (2) is eventually the size of the entire footprint of devices (100) once devices (100) break away from the site of the anastomosis (2).

Figure 7E:
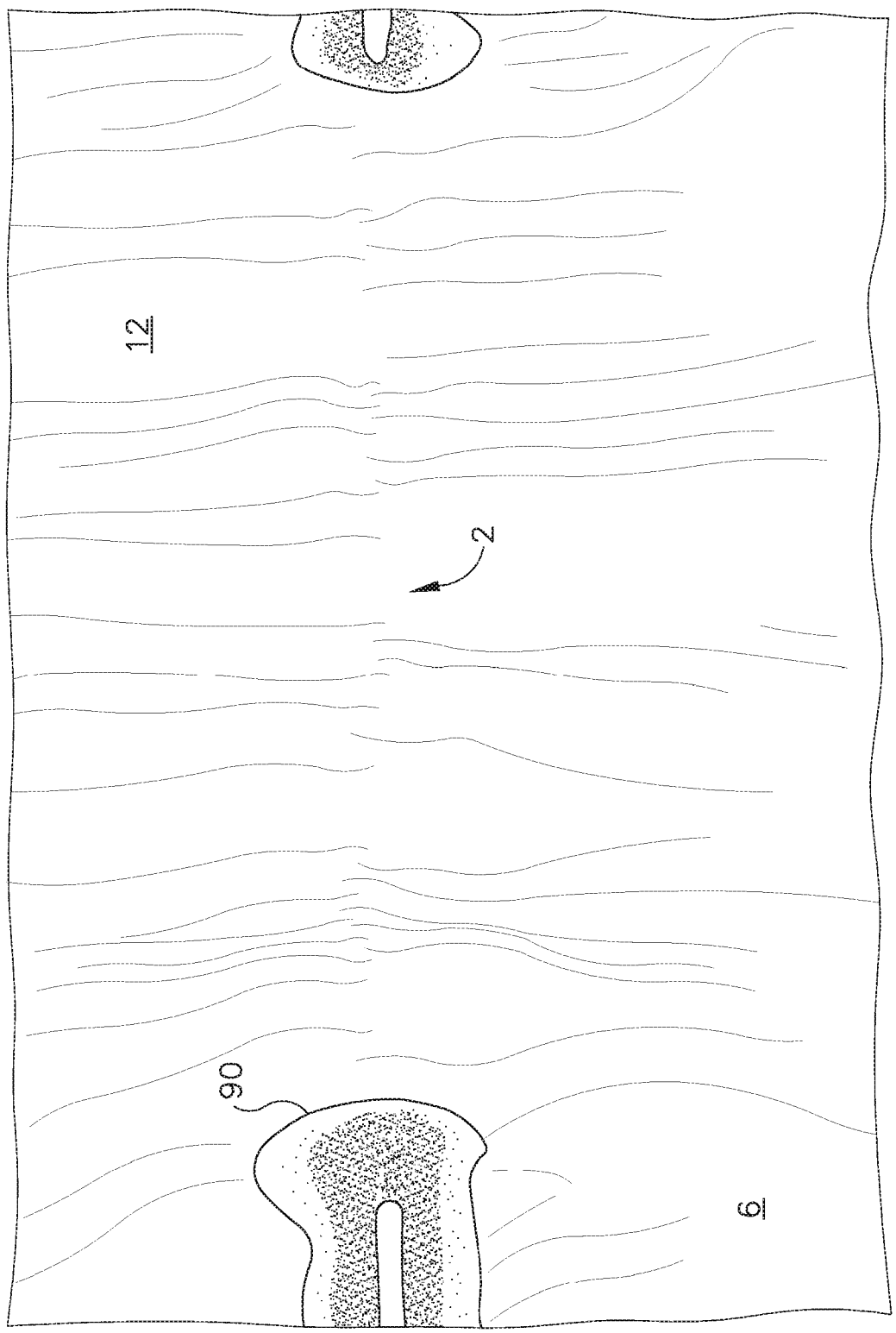
FIG. 7E depicts a cross-sectional view of a pair of the anastomosis compression devices of FIG. 3A, with the anastomosis compression devices having passed through the patient's ileum, leaving behind a secure anastomosis.

When devices (100) have left the site of the anastomosis (2), the structural integrity of the anastomosis (2) remains secure due to natural tissue adhesions. In particular, the exterior of the duodenum (12) and the ileum (6) may have substantial serosa-to-serosa adhesion at this point, due to the sustained contact between the duodenum (12) and the ileum (6). In addition, the mucosa at the interior of the duodenum (12) and the ileum (6) may have remodeled itself to provide a smooth mucosal transition (90) between the duodenum (12) and the ileum (6) at the site of the anastomosis (2), as shown in FIG. 7E. With the anastomosis (2) complete as shown in FIG. 7E, chyme may freely pass from the duodenum (12) to the ileum (6) via the anastomosis (2), without needing to pass through the jejunum (4).

D. Exemplary Variations of Folding Anastomosis Compression Device and Applier Instrument FIG. 8 shows an exemplary alternative folding anastomosis compression device (300). Device (300) of this example may be used as an alternative to device (100) as described above. Device (300) of this example comprises a first end member (310), a second end member (320), a set of links (312, 314, 322, 324), and a resilient member (330). A first magnet (318) is disposed in first end member (310) while a second magnet (328) is disposed in second end member (320). Links (312, 314) are pivotally coupled with first end member (310) by pins (340). Similarly, links (322, 324) are pivotally coupled with second end member (320) by pins (340). Link (312) is coupled with link (322) by a pin (340); while link (314) is coupled with link (324) by a pin (340). It should be understood that the pivotal couplings provided by pins (340) enable links (312, 314, 322, 324) to pivot, thereby enabling device (300) to transition between an expanded configuration and a compressed or collapsed configuration, similar to device (100) described above. When device (300) is in the expanded configuration, links (312, 314, 322, 324) define a diamond-shaped opening. In the present example, device (300) is configured such that device (300) may fit through a conventional trocar (e.g., a 12 mm trocar) when device (300) is in the compressed state. Various suitable dimensions and other structural configurations that may be used for device (300) will be apparent to those of ordinary skill in the art in view of the teachings herein.

Figure 9:
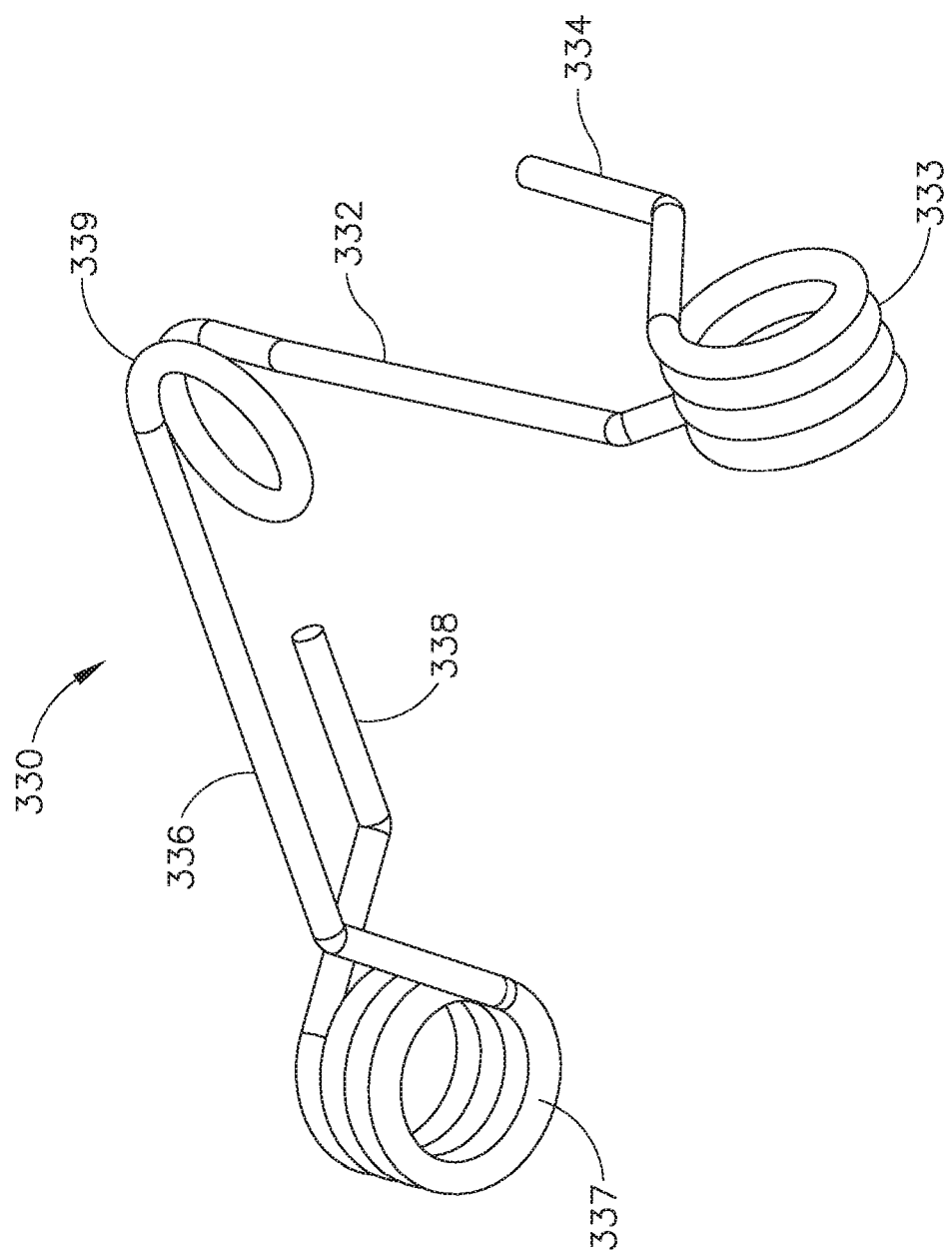
FIG. 9 depicts a perspective view of a resilient member of the anastomosis compression device of FIG. 8.
Figure 10:
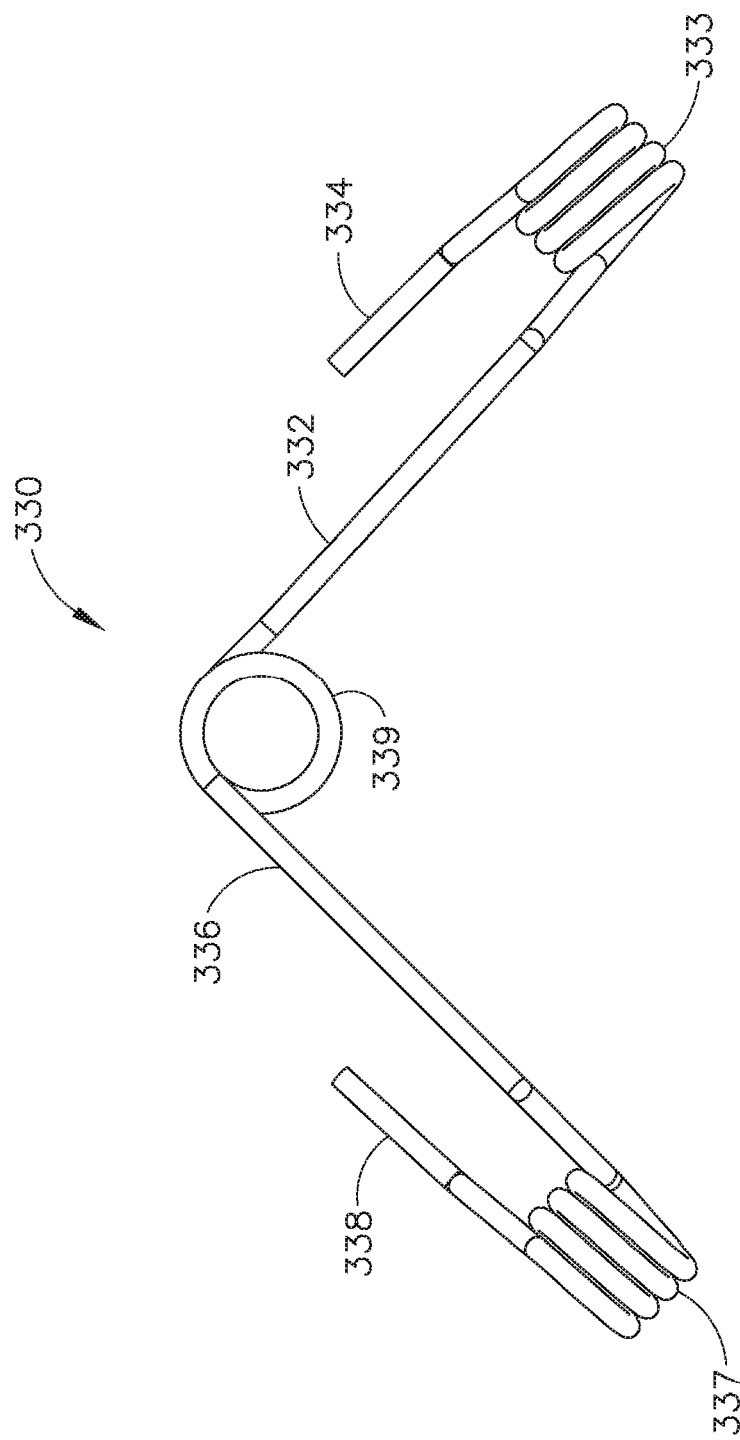
FIG. 10 depicts a top plan view of the resilient member of FIG. 9.
Figure 11:
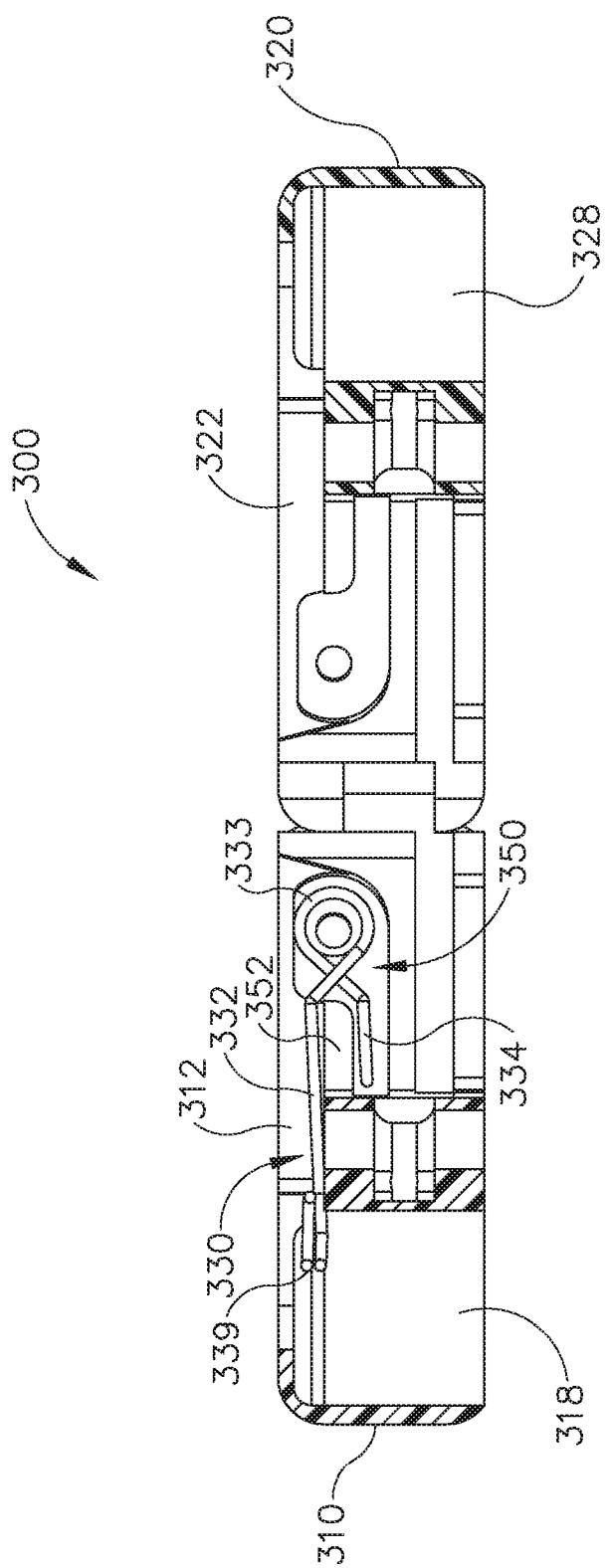
FIG. 11 depicts a cross-sectional view of the anastomosis compression device of FIG. 8, taken along line 11-11 of FIG. 8, with the resilient member in a first position.
Figure 12:
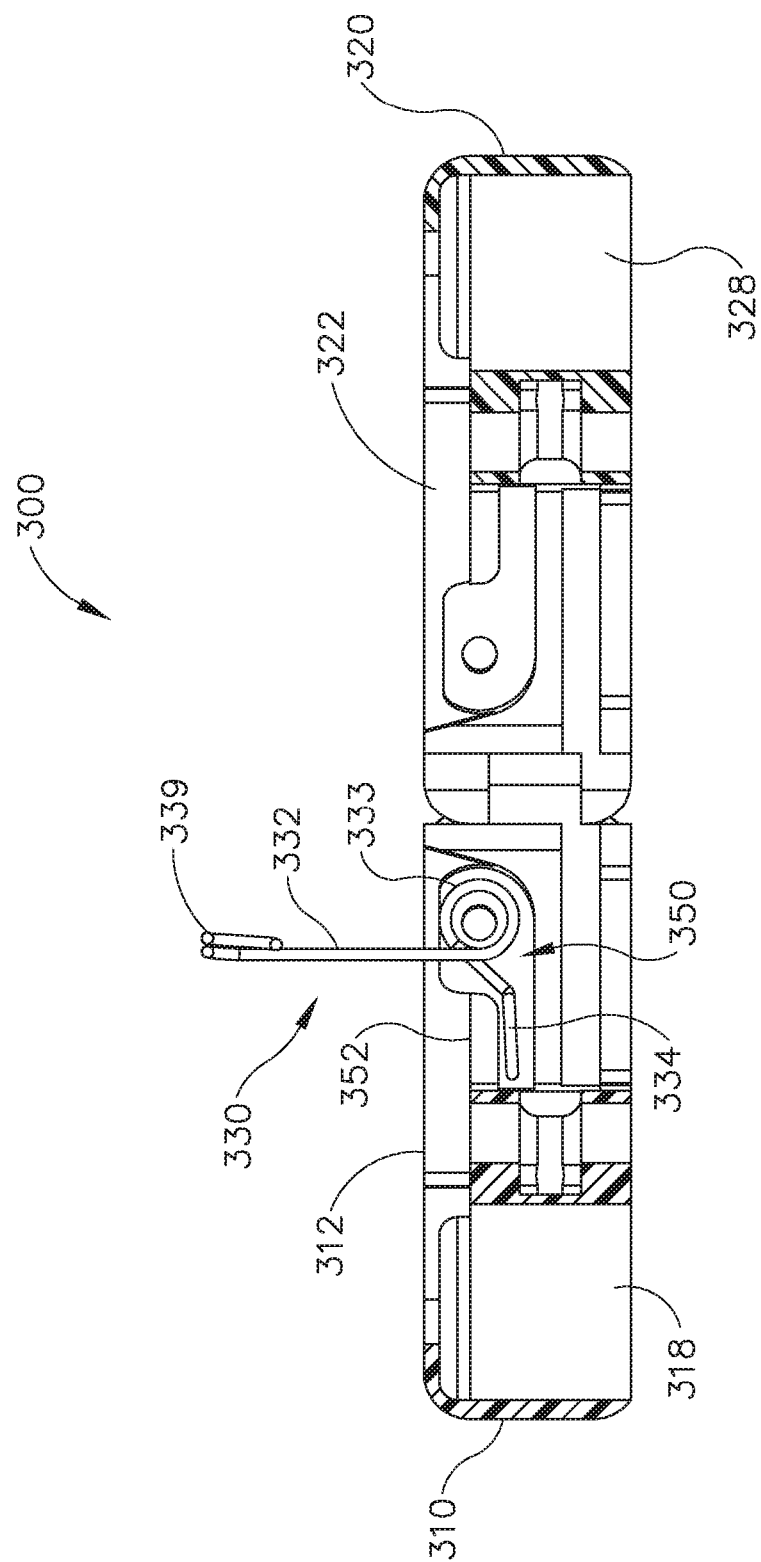
FIG. 12 depicts a cross-sectional view of the anastomosis compression device of FIG. 8, taken along line 11-11 of FIG. 8, with the resilient member in a second position.

Resilient member (330) of the present example comprises a wire formed of resilient material. By way of example only, resilient member (330) may be formed of nitinol and/or any other suitable material(s). As best seen in FIGS. 9-10, resilient member (330) defines a first arm (332) having a first tip region (334), a second arm (336) having a second tip region (338), and a coil bend (339) separating first arm (332) from second arm (336). First tip region (334) is joined to the remainder of first arm (332) by a coil bend (333), such that first tip region (334) is generally parallel with first arm (332). As best seen in FIGS. 11-12, link (312) defines a recess (350) that is configured to receive coil bend (333) and first tip region (334). Link (312) also defines a boss (352) that is configured to restrict movement of arm (352) and/or first tip region (334). It should be understood that link (314) may include similar features. Second tip region (338) is joined to the remainder of second arm (336) by a coil bend (337), such that second tip region (338) is generally parallel with second arm (336). Coil bend (339) is configured such that arms (332, 336) together define an angle of approximately 45° when device (300) is in the expanded configuration. Of course, the various regions of resilient member (330) may define any other suitable angles.

Resilient member (330) is configured to resiliently bias device (300) to the expanded configuration. In particular, coil bends (333, 337) and tip regions (334, 338) bear outwardly on their associated links (312, 314). In some versions, resilient member (330) is resiliently biased to assume a straight configuration where arms (332, 336) would together define an angle of approximately 180°. Thus, resilient member (330) may remain stressed when device (300) is in the expanded configuration. In some other versions, resilient member (330) is resiliently biased to assume a configuration where arms (332, 336) would together define an obtuse angle, an angle of approximately 90°, or an acute angle. It should be understood that, as links (312, 314) are resiliently biased outwardly by coil bends (333, 337) and tip regions (334, 338) bearing directly on links (312, 314), links (312, 314) will also drive links (322, 324) outwardly due to the coupling via pins (340). Resilient member (330) will thus indirectly drive links (322, 324) outwardly via links (312, 314). As with resilient member (130) described above, resilient member (330) of the present example may be engaged by an applier instrument (200), which may hold device (300) in a compressed configuration while device (300) is being applied at an anastomosis site.

Resilient member (330) of the present example is also configured to flex at coil bends (333, 337). However, resilient member (330) is configured to bias arms (332, 336) such that coil bend (339) is biased toward first end member (310). In other words, resilient member (330) is biased toward a position where arms (332, 336) are oriented generally parallel with links (312, 314, 322, 324) as shown in FIGS. 8 and 11. The flexibility of resilient member (330) at coil bends (333, 337) enables coil bend (339) and arms (332, 336) to be deflected away from links (312, 314) as shown in FIG. 12. Such deflection may facilitate coupling of resilient member (330) with instrument (200). Such deflection may also facilitate coupling of resilient member (330) with tissue adjacent to an enterotomy as described above.

It should be understood from the foregoing that resilient member (330) is configured to provide a resilient bias along at least two different paths. One such path is along a plane that is parallel to a plane defined by the upper surfaces of links (312, 314, 322, 324). This bias urges device (300) to the expanded configuration. Put another way, the path of this bias is along the path traveled by links (312, 314, 322, 324) during the transition between the compressed configuration and the expanded configuration. The other path of resilient bias is along a plane that is perpendicular to the plane defined by the upper surfaces of links (312, 314, 322, 324). This bias urges resilient member (330) to a position where bend (339) and arms (332, 336) are oriented along a plane that is substantially parallel to a plane defined by the upper surfaces of links (312, 314, 322, 324). Put another way, the path of this bias is perpendicular to the path traveled by links (312, 314, 322, 324) during the transition between the compressed configuration and the expanded configuration. In some other versions, more than one resilient member (330) is used to provide the biases along these different paths. It should also be understood that another resilient member (330) may be secured to links (322, 324).

As yet another merely illustrative variation, one or more components of devices (100, 300) may be configured to biodegrade to facilitate passage of device (100, 300) through the gastrointestinal tract after the anastomosis (2) has been sufficiently formed. In some such versions, the biodegradability promotes collapse of device (100, 300) to a configuration similar to the compressed configuration described above (e.g., as shown in FIGS. 3C and 8). By way of example only, resilient member (130, 330) may be configured to biodegrade or at least lose its resilience, such that device (100, 300) may freely collapse. As another example, device (100, 300) may include a non-biodegradable second resilient member (not shown) that is configured to bias device (100, 300) to a collapsed state. Such a second resilient member may have a lower spring constant than resilient member (130, 330), such that resilient member (130, 330) provides a stronger bias toward the expanded state while resilient member (130, 330) remains intact. Once resilient member (130, 330) biodegrades, its bias is eventually overcome by the bias of the second resilient member, which urges device (100, 300) to the collapsed state. Of course, the second resilient member need not necessarily be non-biodegradable (e.g., the second resilient member may simply take longer to degrade than resilient member (130, 330), etc.). Still other suitable ways in which biodegradability may be incorporated into devices (100, 300) will be apparent to those of ordinary skill in the art in view of the teachings herein.

Figure 13:
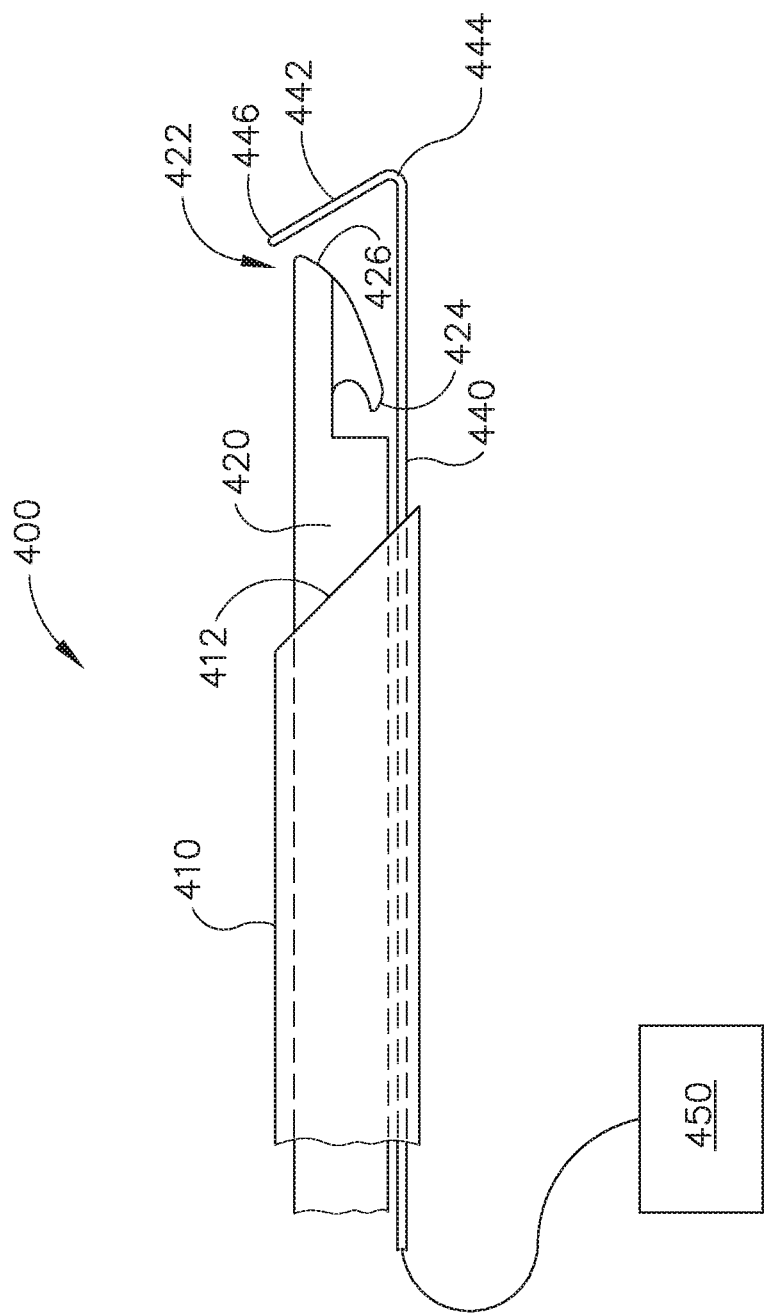
FIG. 13 depicts a side elevational view of the distal end of an exemplary alternative instrument operable to apply the anastomosis compression devices of FIG. 3A and FIG. 8.

FIG. 13 shows an exemplary instrument (400) that may be used to apply device (100, 300) to an anastomosis site. Instrument (400) of this example may be used as an alternative to device (200) as described above. Instrument (400) of this example comprises an outer sheath (410), an inner member (420), and a tip member (440). Outer sheath (410) has an angled distal end (412) that defines an opening (not shown) similar to opening (214) described above. Inner member (420) is slidably disposed in outer sheath (410). Inner member (420) has a distal end (422) that is configured to selectively extend from or retract from the opening of outer sheath (410) as inner member (420) is translated relative to sheath (410). Distal end (422) includes a proximally projecting hook member (424) that is configured to engage bend (139) or coil bend (330) of resilient member (130, 330). The tip (426) of distal end (422) is rounded such that tip (426) is atraumatic in the present example.

As described above with respect to hook member (224), hook member (424) is configured to engage bend (139) or coil bend (339) of resilient member (130, 330) when inner member (420) is advanced to a distal position where distal end (422) extends from the opening of outer sheath (410). When inner member (420) is thereafter retracted relative to outer sheath (410), hook member (424) draws bend (139) or coil bend (339) and adjacent portions of arms (132, 136, 332, 336) into the opening of sheath (410), such that bend (139) or coil bend (339) and adjacent portions of arms (132, 136, 332, 336) are disposed in the interior of sheath (410). The inner sidewalls of sheath (410) that define the opening contact arms (132, 136, 332, 336) and prevent arms (132, 136, 332, 336) from pivoting outwardly. Sheath (410) and inner member (420) thus cooperate to hold device (100, 300) in the compressed configuration while inner member (420) is in a retracted position. As described above, this positioning may be maintained until device (100, 300) is suitably positioned within a bodily lumen (e.g., duodenum, jejunum, ileum, etc.), at which point inner member (420) may be advanced distally relative to sheath (410) to release device (100, 300) at the anastomosis site.

Figure 14:
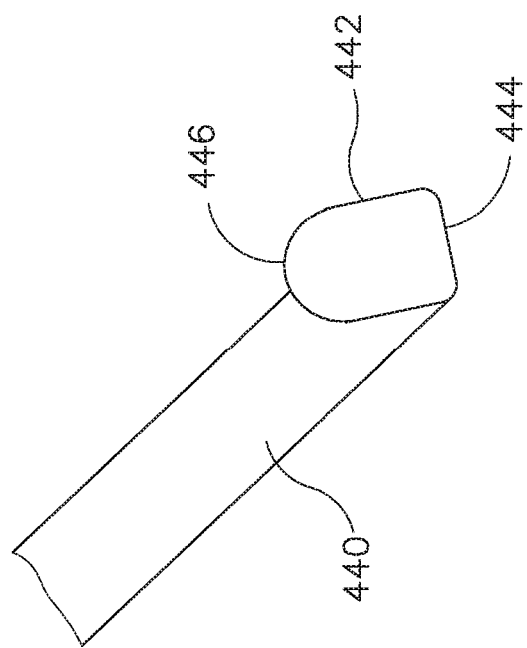
FIG. 14 depicts a perspective view of an exemplary resilient feature of the instrument of FIG. 13.
Figure 15:
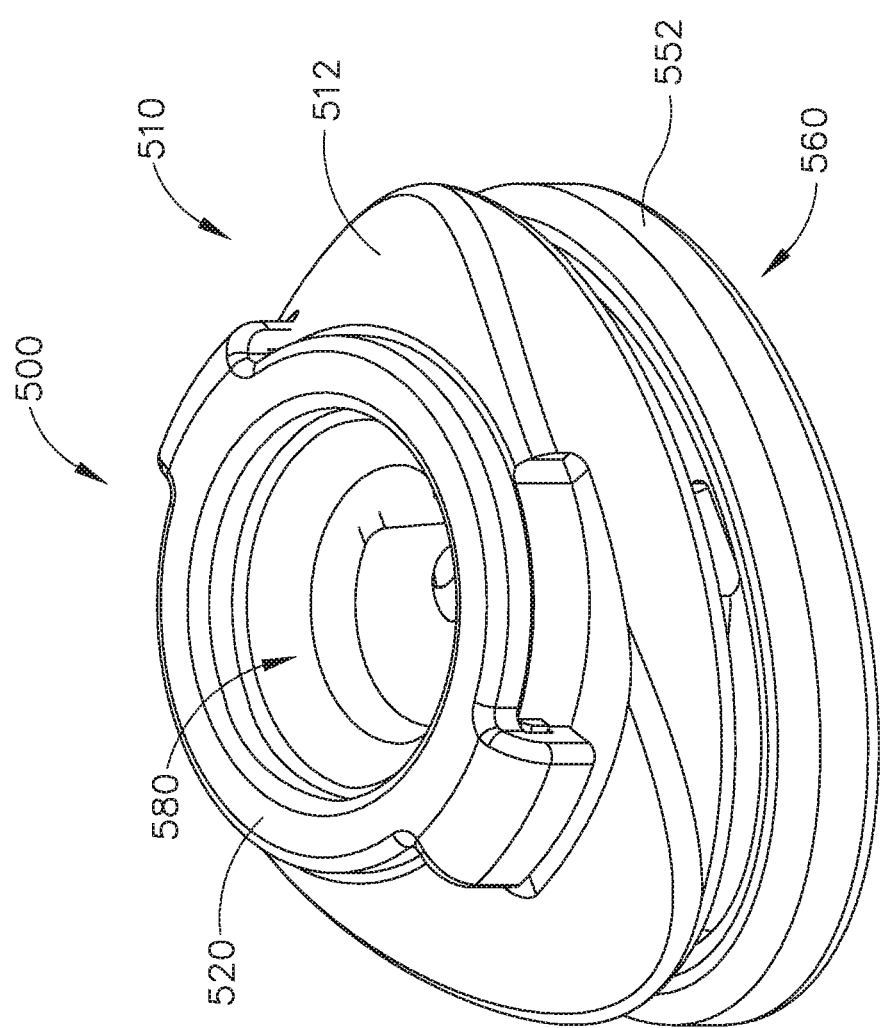
FIG. 15 depicts a perspective view of another exemplary alternative anastomosis compression device.
Figure 16:
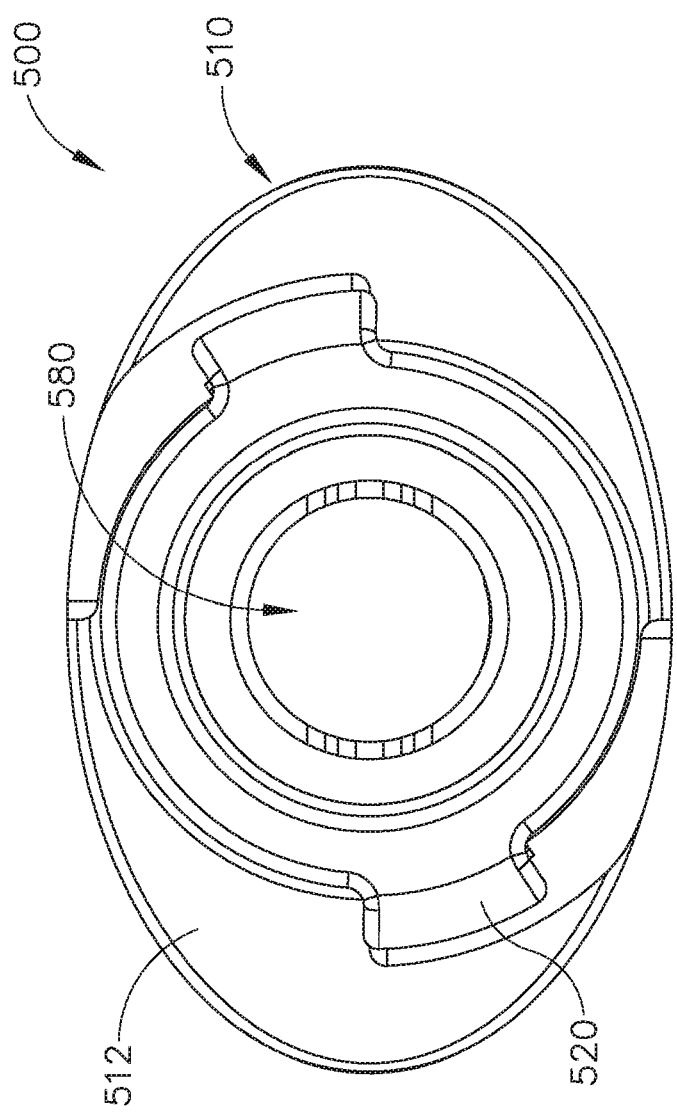
FIG. 16 depicts a top plan view of the anastomosis compression device of FIG. 15.

As shown in FIGS. 13-14, tip member (440) of the present example includes an angled tip portion (442) and an associated bend (444). Tip portion (442) terminates in an arcuate edge (446). Bend (444) is angled such that tip portion (442) projects proximally. In some versions, bend (444) defines an acute angle. In some other versions, bend (444) defines an angle of approximately 45°. Alternatively, any other suitable angle may be used. Tip member (440) of this example is configured to create and/or stretch an enterotomy to facilitate deployment of device (100, 300) in the gastrointestinal tract. In the present example, tip member (440) is coupled with an energy source (450). In some versions, energy source (450) comprises a piezoelectric element that is operable to cause tip member (440) to vibrate at ultrasonic frequencies, such that tip member (440) may be selectively activated like an ultrasonic scalpel blade. In some other versions, energy source (450) is operable to activate tip member (440) with monopolar RF energy. With a ground pad engaging the skin of the patient, tip member (440) may thus act as an electrosurgical scalpel blade. Regardless of how tip member (440) is energized, it should be understood that device (100, 300) and other portions of instrument (400) may be isolated from the energization. Of course, energy source (450) is merely optional, and tip member (440) may instead present a passive sharp edge or even be atraumatic (e.g., in versions where tip member (440) is only used to stretch an enterotomy, etc.). By way of example only, the distal face of tip portion (442) may be convex. Bend (444) may also present a convex edge.

In some versions, bend (444) provides a living hinge that enables tip portion (442) to transition from a bent position as shown in FIGS. 13-14 to a substantially straight position where tip portion (442) is substantially aligned with the remainder of tip member (440). In some such versions, tip portion (442) is resiliently biased to assume the bent position shown in FIGS. 13-14. As tip portion (442) is retracted proximally relative to outer sheath (410) and relative to inner member (420), the proximal face of tip portion (442) cams against the distal face of device (100, 300) that is being held by instrument (400), such that tip portion (442) deflects distally and pivots about bend (444). Tip member (440) may continue to retract proximally until tip portion (442) is fully disposed in outer sheath (410). In the present example, the retraction of tip member (440) would not begin until after device (100, 300) has been positioned within the gastrointestinal tract. After tip portion (442) is fully disposed in outer sheath (410), device (100, 300) would then be released from instrument in the gastrointestinal tract. Other suitable ways in which instrument (400) may be operated will be apparent to those of ordinary skill in the art in view of the teachings herein.

Various suitable features that may be used to provide selective advancement and retraction of inner member (420) and tip member (440) relative to outer sheath (410) will also be apparent to those of ordinary skill in the art in view of the teachings herein. It should also be understood that inner member (420) may be resiliently biased relative to outer sheath (410). For instance, inner member (420) may be resiliently biased to proximally retract distal end (422) within outer sheath (410). Still other suitable features and configurations for instruments that may be used to apply devices (100, 300) will be apparent to those of ordinary skill in the art in view of the teachings herein.

III. Exemplary Anastomosis Compression Device with Axially Biased Member

FIGS. 15-21C show another exemplary anastomosis compression device (500) that may be used to secure an anastomosis between two hollow organs (e.g., between the duodenum and the ileum, etc.). Device (500) of this example comprises a female portion (510) and a male portion (560). Portions (510, 560) are configured to selectively couple together at an anastomosis site and compress tissue adjacent to an anastomosis opening, similar to devices (100, 300) described above. As will be described in greater detail below, female portion (510) is configured to resiliently bias male portion (560) toward female portion (510) to maintain compression of tissue while device (500) is installed at the anastomosis site. Device (500) defines an opening (580)

providing a path for fluid communication at the anastomosis site while device (500) resides at the anastomosis site.

Figure 21A:
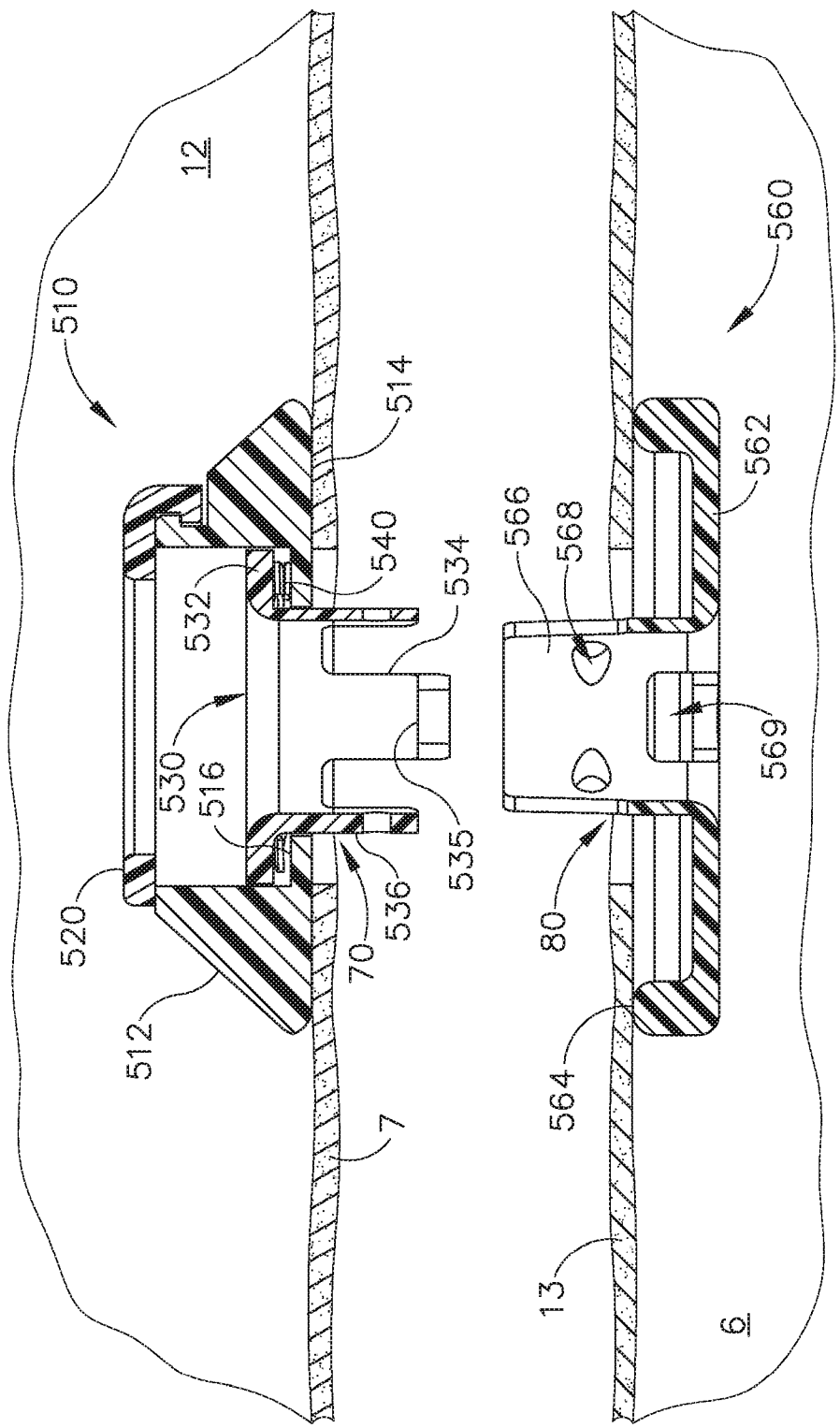
FIG. 21A depicts a side cross-sectional view of the anastomosis compression device of FIG. 15, with the first subassembly positioned in a patient's duodenum and the second subassembly positioned in the patient's ileum, and with the first subassembly separated from the second subassembly.
Figure 21B:
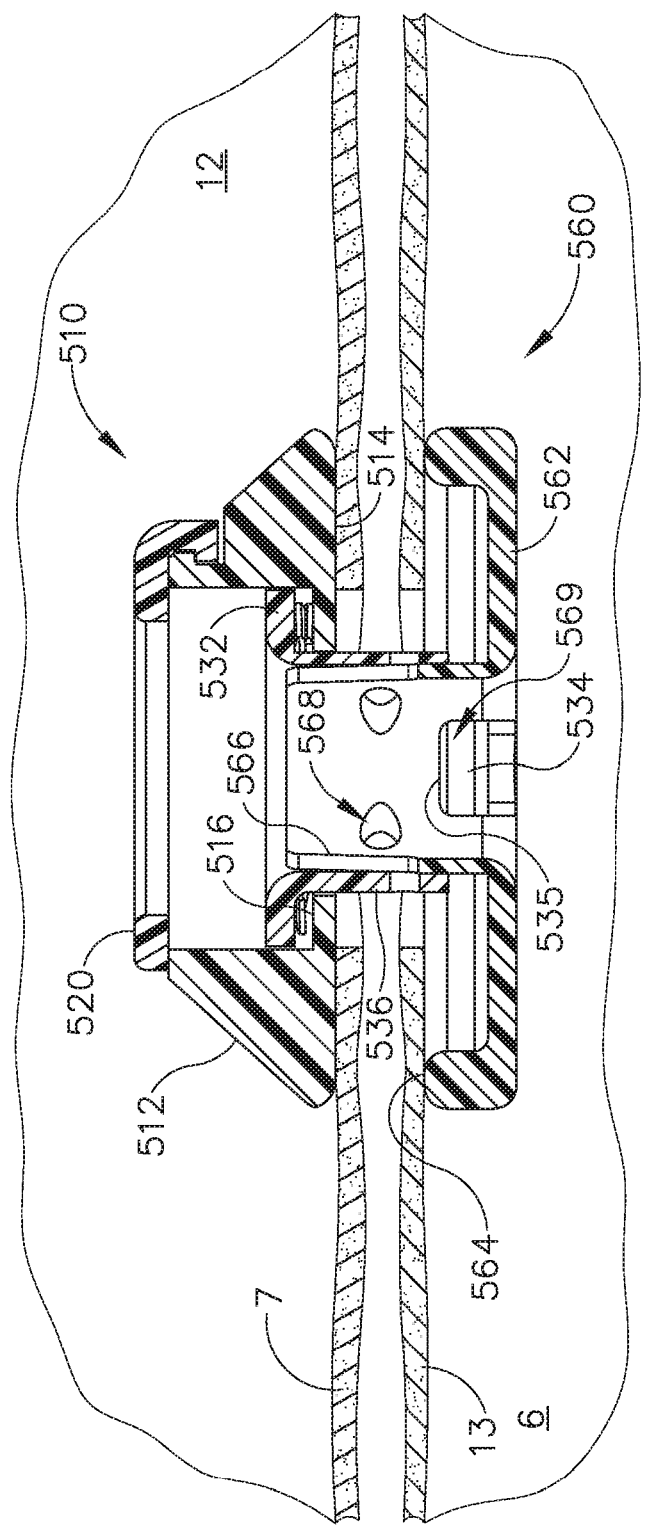
FIG. 21B depicts a side cross-sectional view of the anastomosis compression device of FIG. 15, with the first subassembly coupled with the second subassembly to secure the patient's duodenum and ileum in relation to each other, and with the retracting member of the first subassembly in the extended position.
Figure 21C:
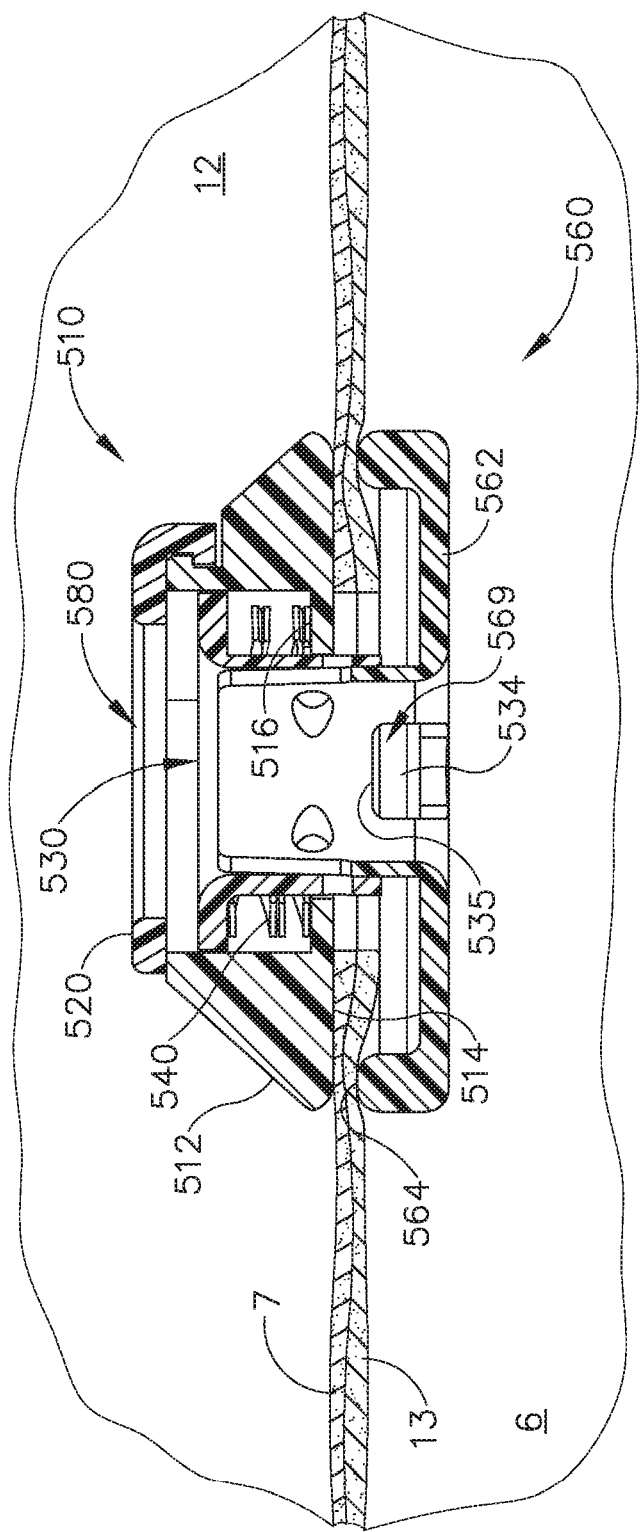
FIG. 21C depicts a side cross-sectional view of the anastomosis compression device of FIG. 15, with the first subassembly coupled with the second subassembly, and with the retracting member of the first subassembly in the retracted position to compress regions of the patient's duodenum and ileum together at an anastomosis.
Figure 22:
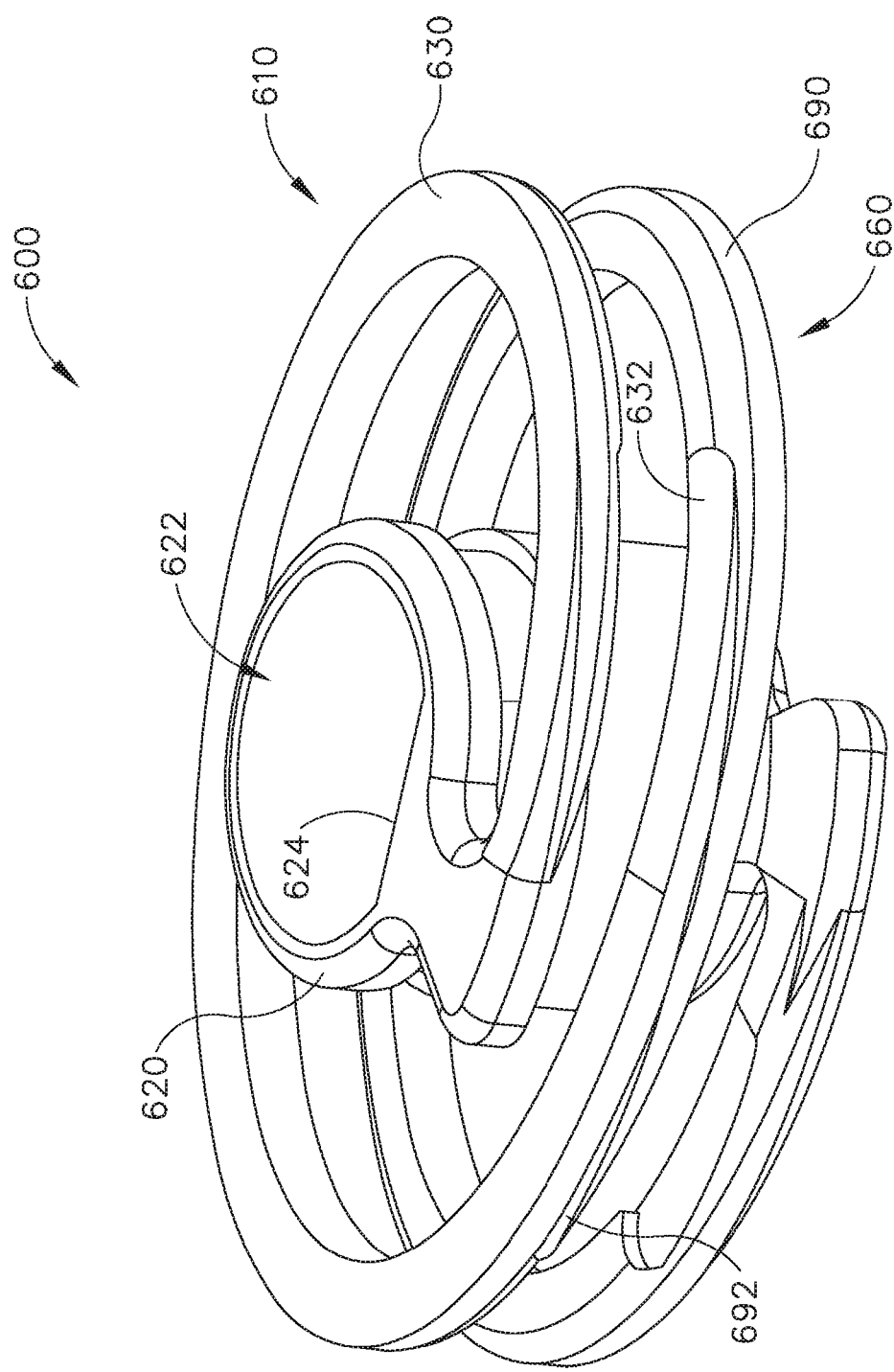
FIG. 22 depicts a perspective view of another exemplary alternative anastomosis compression device.

As shown in FIGS. 15-18, female portion (510) comprises an assembly formed by a base member (512), a retaining ring (520), a coupler (530), and a wave spring assembly (540). As best seen in FIGS. 21A-21C, base member (512) defines an internal annular shoulder (516). Wave spring assembly (540) is captured between annular shoulder (516) of base member (512) and an annular flange (532) of coupler (530). Wave spring assembly (540) is resiliently biased to urge annular flange (532) away from annular shoulder (516), along an axis shared by flange (532) and shoulder (516). Retaining ring (520) is configured to selectively couple with base member (512) and thereby secure coupler (530) within base member (512).

Figure 17:
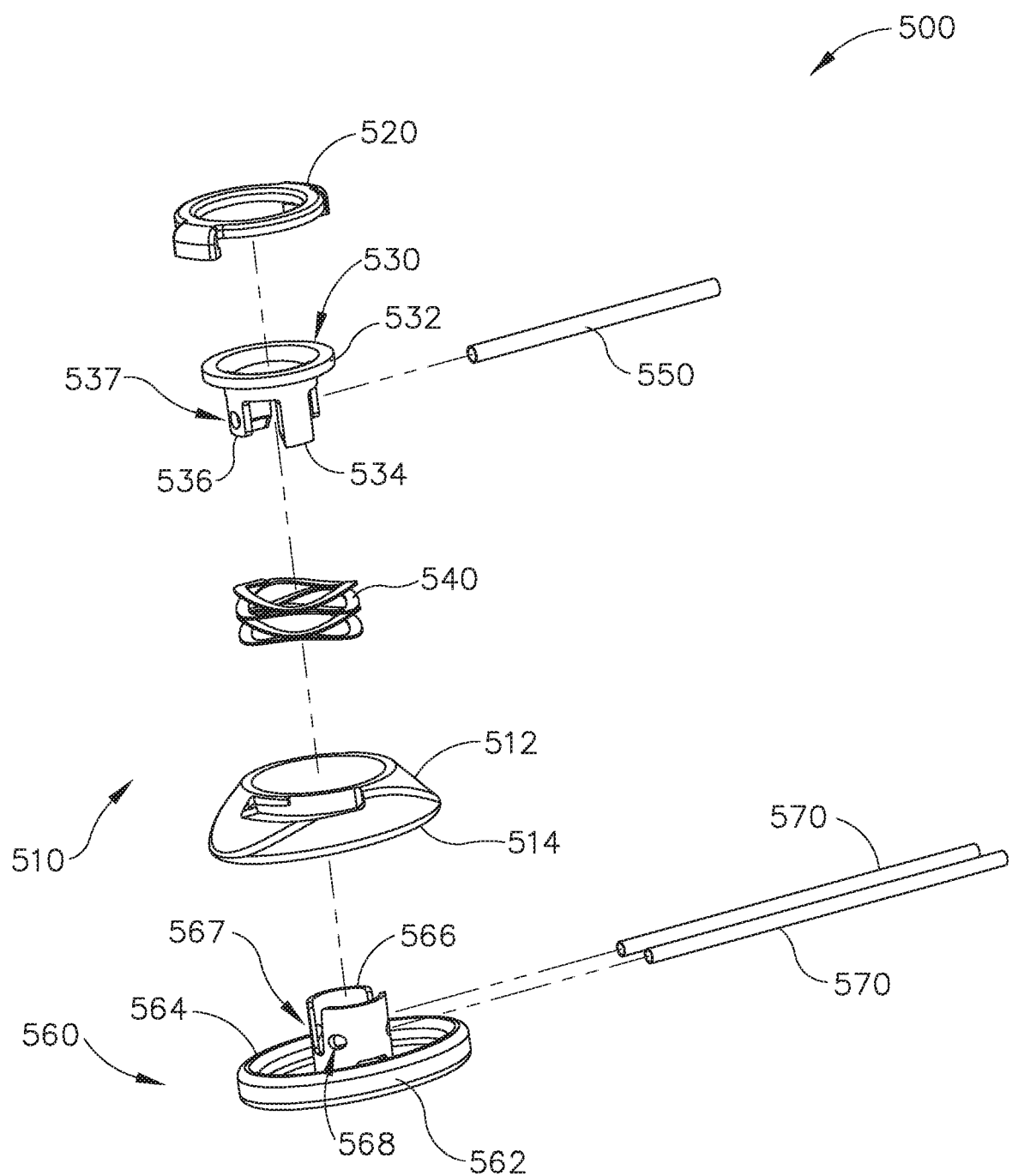
FIG. 17 depicts an exploded perspective view of the anastomosis compression device of FIG. 15.
Figure 20A:
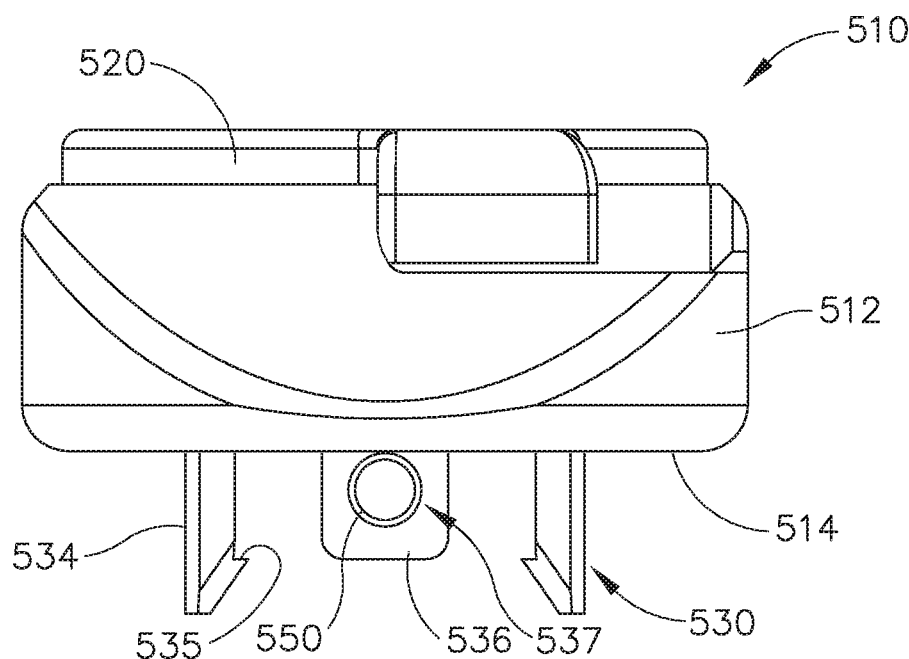
FIG. 20A depicts a side elevational view of the first subassembly of FIG. 18, with a retracting member in an extended position.
Figure 20B:
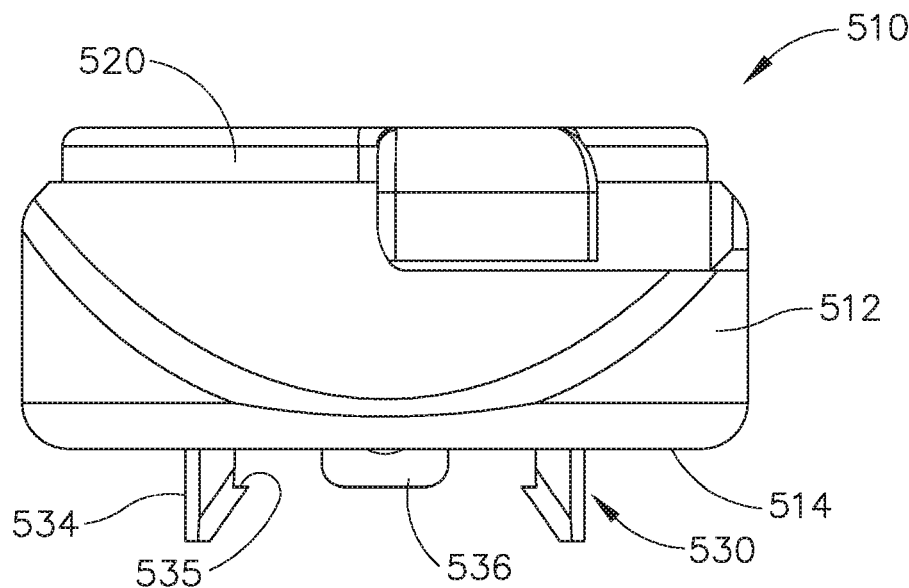
FIG. 20B depicts a side elevational view of the first subassembly of FIG. 18, with the retracting member in a retracted position.

Coupler (530) further comprises a first set of arms (534) and a second set of arms (536). As best seen in FIGS. 20A-20B, each arm (534) includes an inwardly directed snap-fit barb (535). As best seen in FIG. 18, each arm (536) includes an opening (537). As best seen in FIGS. 17 and 20A-20B, openings (537) are configured to removably receive a cylindraceous retaining member (550). Retaining member (550) is configured to engage the bottom surface (514) of base member (512) and hold coupler (530) in an extended position as shown in FIG. 20A. In the extended position, barbs (535) are substantially spaced away from bottom surface (514), and wave spring assembly (540) is in a substantially stressed, compressed configuration. This configuration is also shown in FIGS. 21A-21B. When retaining member (550) is withdrawn from openings (537), the resilient bias of wave spring assembly (540) drives coupler (530) upwardly into a retracted configuration as shown in FIGS. 20B and 21C. In this configuration, barbs (535) are substantially closer to bottom surface (514).

As best shown in FIGS. 17 and 19, male portion (560) comprises a base (562) having an upwardly extending elliptical flange (564) and an upwardly extending post feature (566). Post feature (566) includes a pair of vertically extending slots (567), a pair of retainer openings (568), and a pair of snap-fit barb openings (569). Slots (567) are configured to accommodate retaining member (550) when male portion (560) is initially coupled with female portion (510) as will be described in greater detail below. Retainer openings (568) are configured to receive cylindraceous retaining members (570), which may be used to position and hold male portion (560). Openings (569) are configured to receive barbs (535) of coupler (530) in a snap-fit fashion, as will also be described in greater detail below.

In an exemplary use of device (500) is shown in FIGS. 21A-21C, in which retaining members (550, 570) have been omitted for clarity. In the exemplary use, an enterotomy (70) is created in the duodenum (12) and an enterotomy (80) is created in the ileum (6), as described above with respect to an exemplary use of device (100). Female portion (510) is then inserted through the enterotomy (70) and oriented such that arms (534, 536) protrude outwardly through the enterotomy (70), as shown in FIG. 21A. Female portion (510) is held in position in the duodenum (12) by retaining member (550). Male portion (560) is inserted through the enterotomy (80) and is oriented such that post feature (566) protrudes outwardly through the enterotomy (80). Male portion (560) is held in position in the ileum (6) by retaining members (570).

With portions (510, 560) positioned as shown in FIG. 21A, portions (510, 560) are then brought toward each other, drawing the duodenum (12) and the ileum (6) closer together. Retaining members (570) are removed from openings (568), providing clearance for post feature (566) to enter the interior of coupler (530) to the point where barbs (535) snap into openings (569) as shown in FIG. 21B. At this stage retaining member (550) remains disposed in openings (537). Retaining member (550) is further accommodated within slots (567) of post feature (566).

After reaching the stage shown in FIG. 21B, retaining member (550) is removed from openings (537). This enables wave spring assembly (540) to drive coupler (530) to the retracted position relative to base member (512). With barbs (535) disposed in openings (569) of male member (560), this movement of coupler (530) drives male member (560) toward base member (512). This movement of male ember (560) toward base member (512) compresses the layers of tissue (7, 13) between flange (564) and the bottom surface (514) of base member (512), as shown in FIG. 21C. This compression of tissue (7, 13) provides a secure seal of the anastomosis formed by the fully assembled device (500). Over a period of time, the ischemia caused by this compression of tissue (7, 13) also eventually results in necrosis of the tissue (7, 13), as described above. Device (500) thus eventually breaks free from the anastomosis site and passes through the patient's gastrointestinal tract as described above in the context of device (100).

It should be understood that after device (500) has left the site of the anastomosis (2), the structural integrity of the anastomosis (2) remains secure due to natural tissue adhesions. In particular, the exterior of the duodenum (12) and the ileum (6) may have substantial serosa-to-serosa adhesion at this point, due to the sustained contact between the duodenum (12) and the ileum (6). In addition, the mucosa at the interior of the duodenum (12) and the ileum (6) may have remodeled itself to provide a smooth mucosal transition (90) between the duodenum (12) and the ileum (6) at the site of the anastomosis (2). While female portion (510) is applied in the duodenum (12) and male portion (560) is applied in the ileum (6) in the above example, it should be understood that female portion (510) may instead be applied in the ileum (6) while male portion (560) is applied in the duodenum (12). Furthermore, device (500) may be applied in other regions of the gastrointestinal tract or in some other portion of the human anatomy. Various other suitable ways in which device (500) may be configured and used will be apparent to those of ordinary skill in the art in view of the teachings herein.

IV. Exemplary Anastomosis Compression Device with Corkscrew Insertion Features

Figure 23:
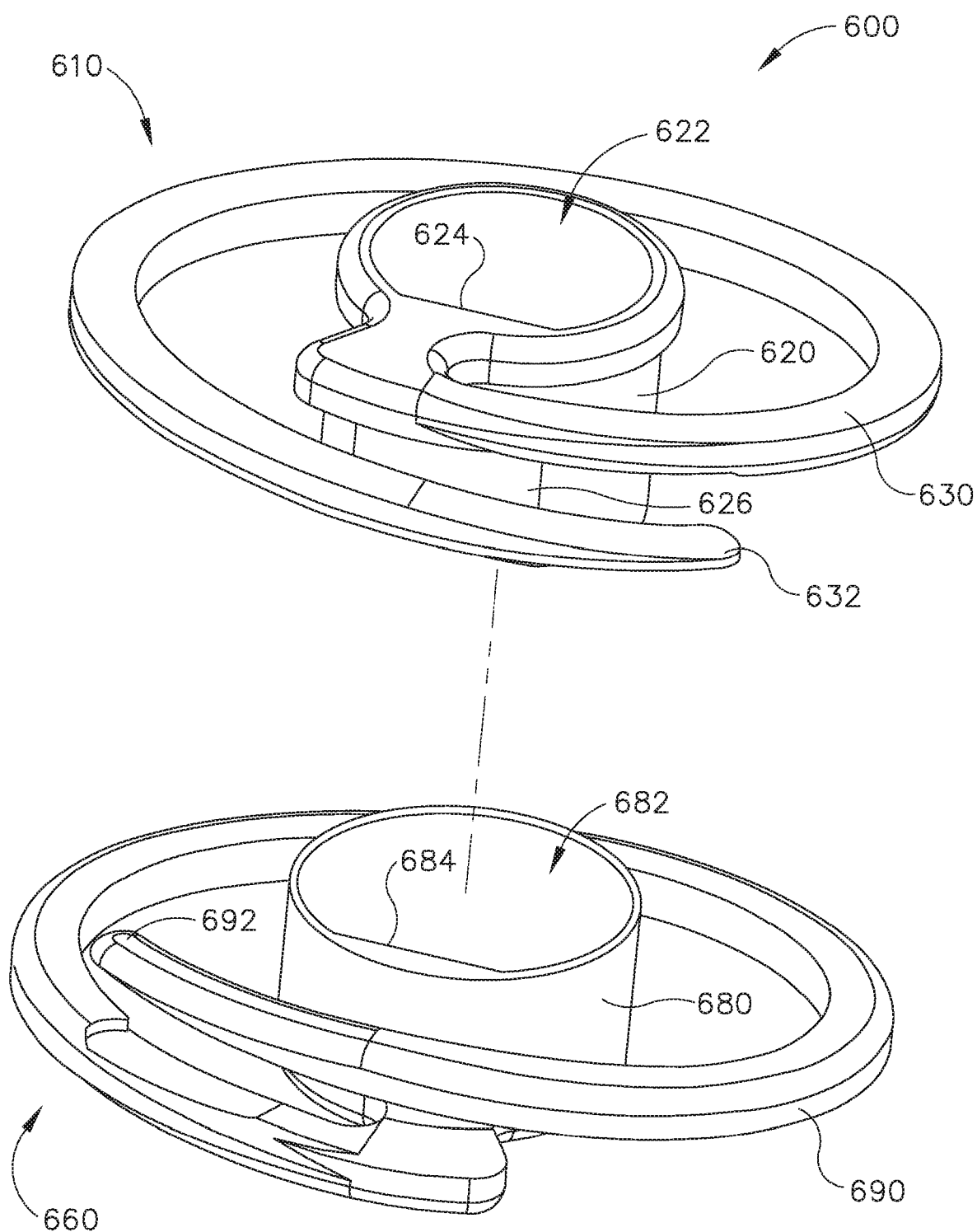
FIG. 23 depicts an exploded perspective view of the anastomosis compression device of FIG. 22.
Figure 24:
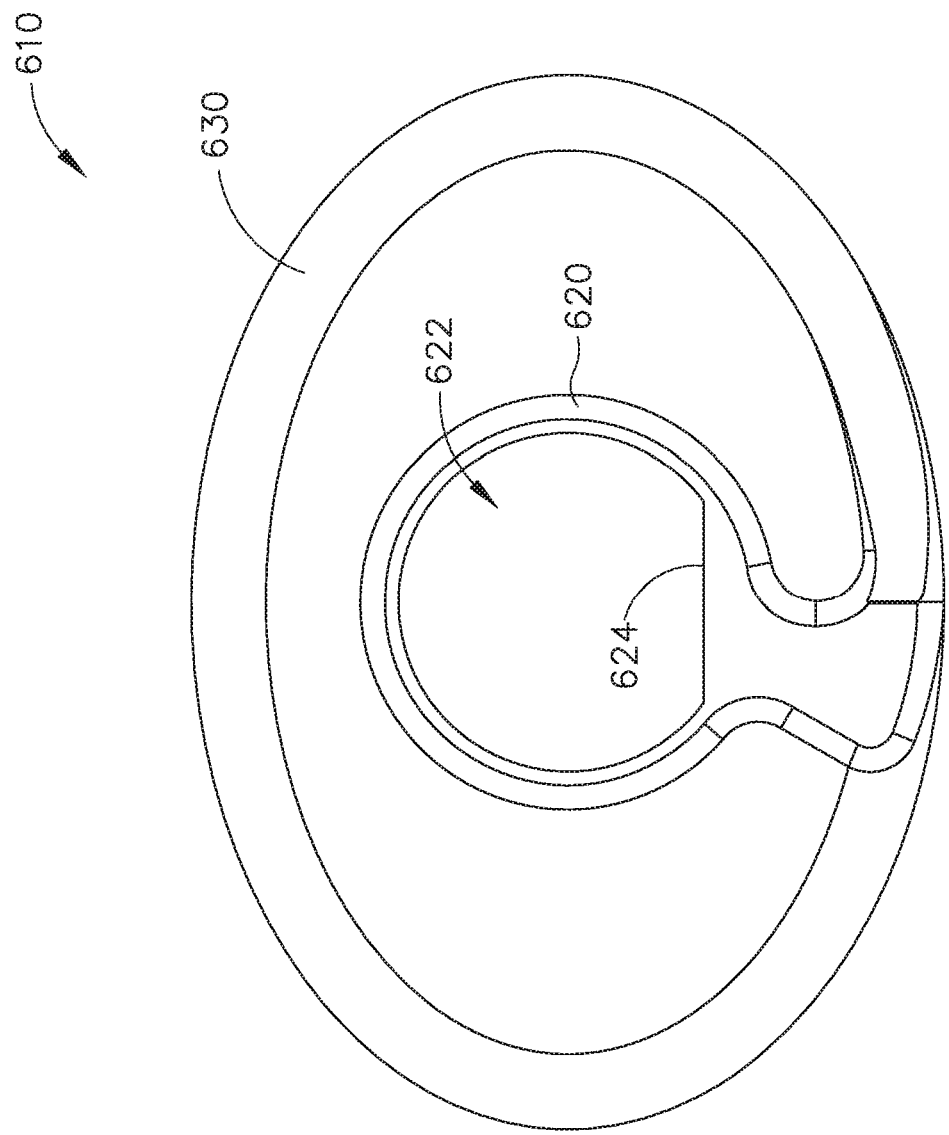
FIG. 24 depicts a top plan view of a male member of the anastomosis compression device of FIG. 22.

FIGS. 22-26 show another exemplary anastomosis compression device (600) that may be used to secure an anastomosis between two hollow organs (e.g., between the duodenum and the ileum, etc.). Device (600) of this example comprises a male portion (610) and a female portion (660). Portions (610, 660) are configured to selectively couple together at an anastomosis site and compress tissue adjacent to an anastomosis opening, similar to devices (100, 300) described above. Male portion (610) comprises a post feature (620) and a corkscrew feature (630). As best seen in FIG. 24, post feature (620) defines a passageway (622) having an internal flat (624). As best seen in FIG. 23, a similar flat (626) is formed in the exterior of post feature (620). Corkscrew feature (630) terminates in an atraumatic free end (632).

Figure 25:
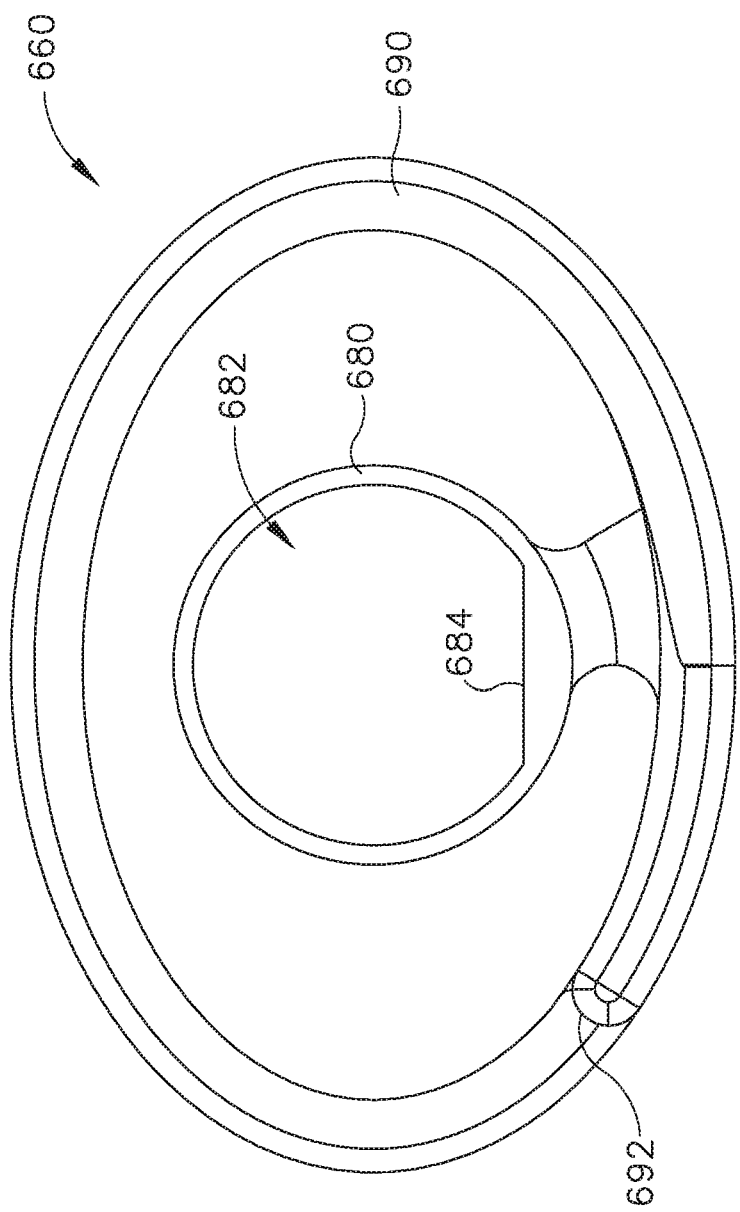
FIG. 25 depicts a top plan view of a female member of the anastomosis compression device of FIG. 22.

Female portion (660) comprises a post feature (680) and a corkscrew feature (690). As best seen in FIG. 25, post feature (680) defines a passageway (682) having an internal flat (684). Corkscrew feature (690) terminates in an atraumatic free end (692). Passageway (682) of female portion (660) is configured to receive post feature (620) of male portion (610). Flat (684) is configured to complement flat (626) to enable insertion of post feature (620) in passageway (682) and to ensure appropriate angular alignment of male portion (610) relative to female portion (660). Corkscrew features (630, 690) are configured such that when portions (610, 660) are fully coupled together, corkscrew features (630, 690) will deform slightly, compressing any tissue captured between opposing faces of corkscrew features (630, 690). Corkscrew features (630, 690) may thus be formed of a resilient material (e.g., a resilient plastic, etc.).

In an exemplary use of device (600), an enterotomy (70) is created in the duodenum (12) and an enterotomy (80) is created in the ileum (6), as described above with respect to an exemplary use of device (100). Male portion (610) is inserted through the enterotomy (70) in the duodenum (12) and is oriented such that post feature (620) protrudes outwardly through the enterotomy (70). During this insertion, male portion (610) may be titled such and rotated such that corkscrew feature (630) passes through the enterotomy (70) progressively, without requiring the enterotomy (70) to be widened further beyond the outer diameter defined by post feature (620). Female portion (660) is inserted through the enterotomy (80) in the ileum (6) and is oriented such that post feature (680) protrudes outwardly through the enterotomy (80). During this insertion, female portion (660) may be titled such and rotated such that corkscrew feature (690) passes through the enterotomy (80) progressively, without requiring the enterotomy (80) to be widened further beyond the outer diameter defined by post feature (680).

Figure 26:
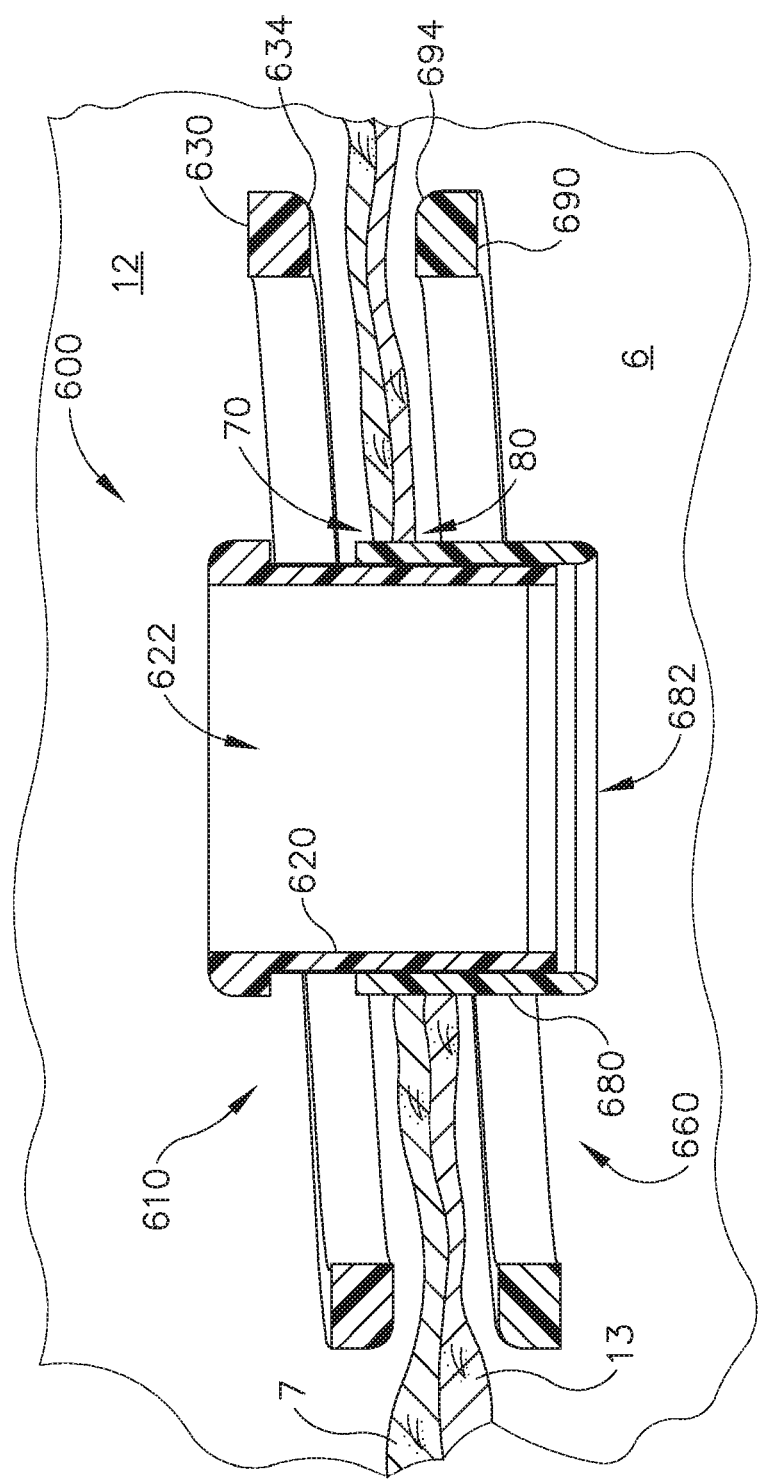
FIG. 26 depicts a side cross-sectional view of the anastomosis compression device of FIG. 22, with the male and female members secured together to compress regions of a patient's duodenum and ileum together at an anastomosis.

With male portion (610) disposed in the duodenum (12) and female portion (660) disposed in the ileum (6) as described above, portions (610, 660) are then brought toward each other, drawing the duodenum (12) and the ileum (6) closer together. Male portion (610) is then inserted in passageway (682) of female portion (660), such that portions (610, 660) are coupled together as shown in FIG. 26. At this stage, corkscrew feature (630) bears on the tissue (7) of the duodenum (12) while corkscrew feature (690) bears on the tissue (13) of the ileum (6) in the opposite direction, such that the layers of tissue (7, 13) are compressed between corkscrew features (630, 690). This compression of tissue (7, 13) provides a secure seal of the anastomosis formed by the fully assembled device (600). Over a period of time, the ischemia caused by this compression of tissue (7, 13) also eventually results in necrosis of the tissue (7, 13), as described above. Device (600) thus eventually breaks free from the anastomosis site and passes through the patient's gastrointestinal tract as described above in the context of device (100).

Corkscrew features (630, 690) may be configured such that tissue (7, 13) is compressed along any suitable portion of the length of corkscrew features (630, 690) when portions (610, 660) are fully coupled together. As can also be seen in FIG. 26, the tissue contacting regions of corkscrew features (630, 690) include rounded corners (634, 694), which may prevent corkscrew features (630, 690) from prematurely migrating through the tissue (7, 13).

In some versions, male portion post feature (620) fits snugly in passageway (682), such that portions (610, 660) remain secured together through an interference fitting. In some other versions, portions (610, 660) comprise complementary snap-fit features that secure portions (610, 660) together. In still other versions, portions (610, 660) comprise magnetic features that secure portions (610, 660) together. Still other suitable ways in which portions (610, 660) may be secured together will be apparent to those of ordinary skill in the art in view of the teachings herein.

It should be understood that after device (600) has left the site of the anastomosis (2) (e.g., after tissue (7, 13) within the footprint of device (600) has necrosed), the structural integrity of the anastomosis (2) remains secure due to natural tissue adhesions. In particular, the exterior of the duodenum (12) and the ileum (6) may have substantial serosa-to-serosa adhesion at this point, due to the sustained contact between the duodenum (12) and the ileum (6). In addition, the mucosa at the interior of the duodenum (12) and the ileum (6) may have remodeled itself to provide a smooth mucosal transition (90) between the duodenum (12) and the ileum (6) at the site of the anastomosis (2). While male portion (610) is applied in the duodenum (12) and female portion (660) is applied in the ileum (6) in the above example, it should be understood that male portion (610) may instead be applied in the ileum (6) while female portion (660) is applied in the duodenum (12). Furthermore, device (600) may be applied in other regions of the gastrointestinal tract or in some other portion of the human anatomy. Various other suitable ways in which device (600) may be configured and used will be apparent to those of ordinary skill in the art in view of the teachings herein.

V. Exemplary Anastomosis Compression Device with Biased Pivoting Links

Figure 27:
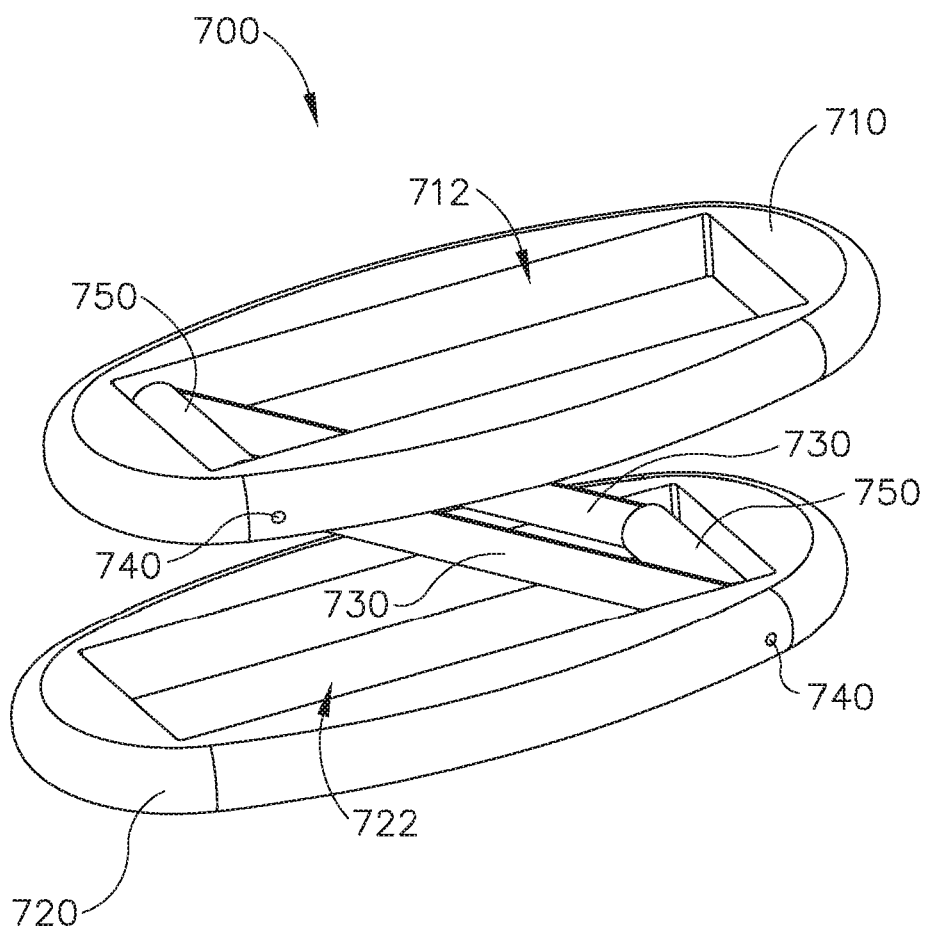
FIG. 27 depicts a perspective view of another exemplary alternative anastomosis compression device.
Figure 28:
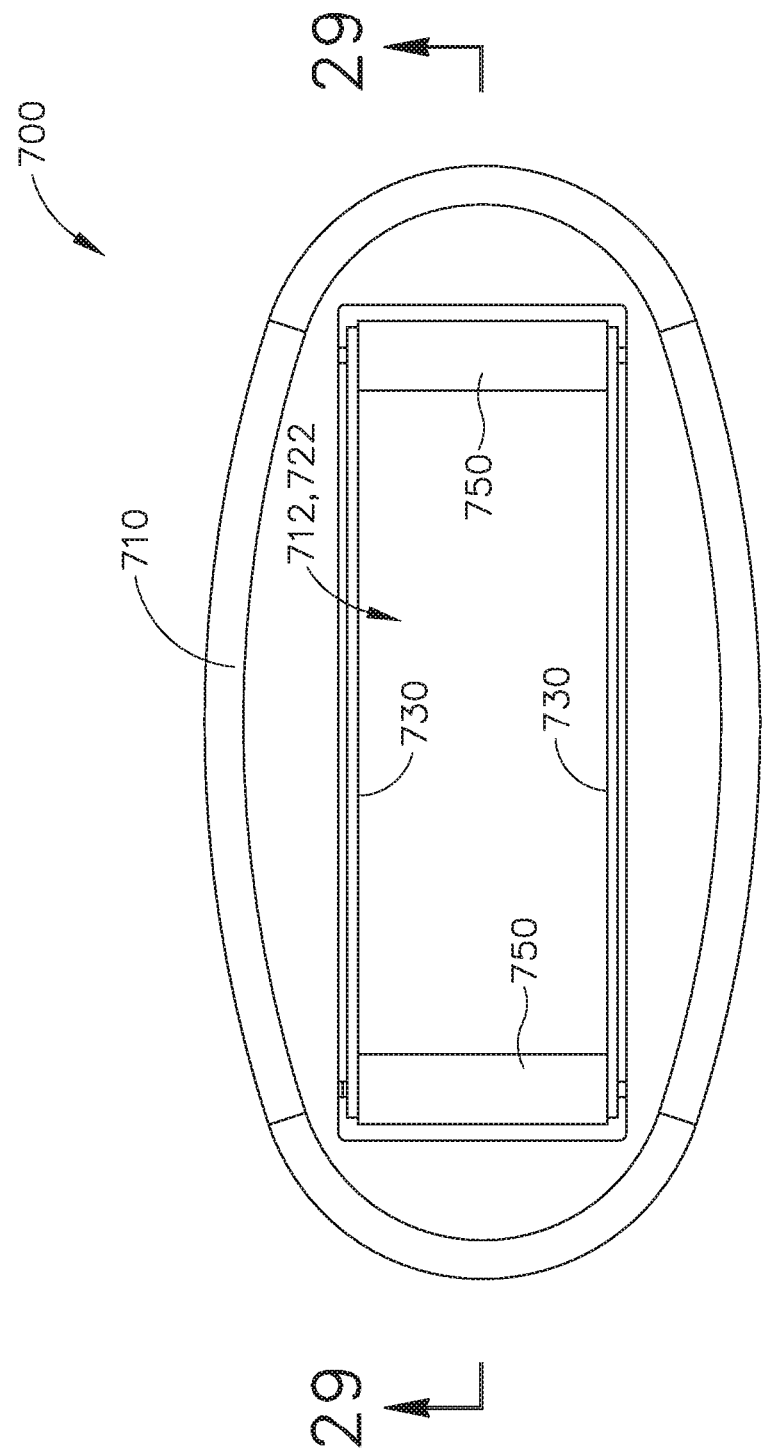
FIG. 28 depicts a top plan view of the anastomosis compression device of FIG. 27.
Figure 29:
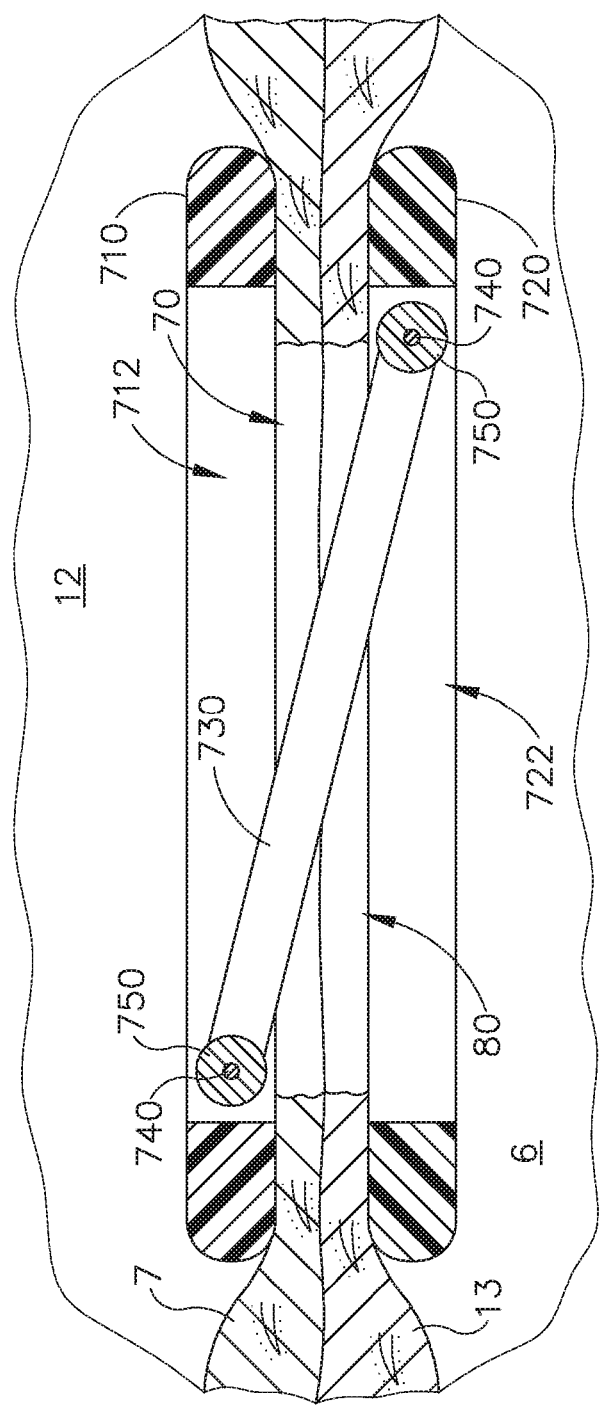
FIG. 29 depicts a side cross-sectional view of the anastomosis compression device of FIG. 27, taken along line 29-29 of FIG. 28.

FIGS. 27-29 show another exemplary anastomosis compression device (700) that may be used to secure an anastomosis between two hollow organs (e.g., between the duodenum and the ileum, etc.). Device (700) of this example comprises a first plate (710), a second plate (720), and a pair of links (730). Plates (710, 720) define respective rectangular openings (712, 722). Links (730) are positioned at the lateral sides of openings (712, 722). One end of each link (730) is pivotally secured to plate (710) at one end of opening (712) by a pin (740); while the other end of each link (730) is pivotally secured to plate (720) at the opposite end of opening (722) by a pin (740). Spacers (750) are positioned coaxially along each pin (740), to maintain the ends of links (730) in spaced-apart positions.

In the present example, plates (710, 720) are biased toward each other, yet plates (710, 720) may be separated by pivoting links (730) at pins (740) as shown in FIG. 27. In some versions, torsion springs (e.g., positioned about pins (740)) are used to resiliently bias plates (710, 720). In some other versions, magnets are used to magnetically bias plates (710, 720). Other suitable ways in which plates (710, 720) may be biased toward each other will be apparent to those of ordinary skill in the art in view of the teachings herein. It should also be understood that device (700) may include a pull-pin, sliding lock feature, and/or other type of feature that selectively assists in keeping plates (710, 720) separate from each other without the operator having to manually resist the bias of plates (710, 720) during positioning of device (700). Various suitable forms that such a bias resistance feature may take will be apparent to those of ordinary skill in the art in view of the teachings herein.

In an exemplary use of device (700), an enterotomy (70) is created in the duodenum (12) and an enterotomy (80) is created in the ileum (6), as described above with respect to an exemplary use of device (100). Plate (710) is inserted through the enterotomy (70) in the duodenum (12) and is oriented such that links (730) protrude outwardly through the enterotomy (70). Plate (720) is inserted through the enterotomy (80) in the ileum (6), with links (730) protruding outwardly through the enterotomy (80). With plate (710) disposed in the duodenum (12) and plate (720) disposed in the ileum (6) as described above, plates (710, 720) are released, allowing the bias of plates (710, 720) to draw the duodenum (12) and the ileum (6) closer together. At this stage, plate (710) bears on the tissue (7) of the duodenum (12) while plate (720) bears on the tissue (13) of the ileum (6) in the opposite direction, such that the layers of tissue (7, 13) are compressed between plates (710, 720) as shown in FIG. 29. This compression of tissue (7, 13) provides a secure seal of the anastomosis formed by the fully deployed device (700). Over a period of time, the ischemia caused by this compression of tissue (7, 13) also eventually results in necrosis of the tissue (7, 13), as described above. Device (700) thus eventually breaks free from the anastomosis site and passes through the patient's gastrointestinal tract as described above in the context of device (100).

It should be understood that after device (700) has left the site of the anastomosis (2) (e.g., after tissue (7, 13) within the footprint of device (700) has necrosed), the structural integrity of the anastomosis (2) remains secure due to natural tissue adhesions. In particular, the exterior of the duodenum (12) and the ileum (6) may have substantial serosa-to-serosa adhesion at this point, due to the sustained contact between the duodenum (12) and the ileum (6). In addition, the mucosa at the interior of the duodenum (12) and the ileum (6) may have remodeled itself to provide a smooth mucosal transition (90) between the duodenum (12) and the ileum (6) at the site of the anastomosis (2). While plate (710) is applied in the duodenum (12) and plate (720) is applied in the ileum (6) in the above example, it should be understood that plate (710) may instead be applied in the ileum (6) while plate (720) is applied in the duodenum (12). Furthermore, device (700) may be applied in other regions of the gastrointestinal tract or in some other portion of the human anatomy. Various other suitable ways in which device (700) may be configured and used will be apparent to those of ordinary skill in the art in view of the teachings herein.

VI. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of modifying a metabolic pathway of a digestive system comprising an intestinal tract, wherein the intestinal tract comprises a small intestine, a large intestine, a colon, an ileocecal junction, and a ligament of Trietz, wherein the small intestine comprises a duodenum, a jejunum, and an ileum, wherein the small intestine further comprises a first initial length and a duodenal papilla, the method comprising using a compression device with a resilient feature that contacts an exterior of a hollow organ of the intestinal tract and comprises a bias to alter a configuration of the compression device between a compressed state and an expanded state when the resilient feature contacts the exterior of the hollow organ of the intestinal tract to create a pathway within the intestinal tract by establishing a connection between a proximal location within the small intestine and a distal location within the intestinal tract, wherein the connection places the region of the small intestine associated with the proximal location and the region of the intestinal tract associated with the distal location in communication, wherein the proximal location within the small intestine is distal to the duodenal papilla, and wherein the pathway defines a second length of the intestinal tract between about 10% and about 70% of the first initial length.

2. The method of claim 1, wherein the proximal location is within the duodenum and the distal location is within the jejunum.

3. The method of claim 1, wherein the proximal location is within the duodenum and the distal location is within the ileum.

4. The method of claim 1, wherein the proximal location is within the jejunum and the distal location is within the jejunum.

5. The method of claim 1, wherein the proximal location is within the jejunum and the distal location is within the ileum.

6. The method of claim 1, wherein the proximal location is within the jejunum and the distal location is within the colon.

7. The method of claim 6, wherein the proximal location is at least about 200 centimeters from the ligament of Treitz.

8. The method of claim 1, wherein the proximal location is within the ileum and the distal location is within the ileum.

9. The method of claim 1, wherein the proximal location is within the ileum and the distal location is within the colon.

10. The method of claim 1, wherein the proximal location is within the jejunum, wherein the proximal location is further between about 10 centimeters and about 200 centimeters distal to the ligament of Treitz.

11. The method of claim 10, wherein the proximal location is about 100 centimeters distal to the ligament of Treitz.

12. The method of claim 10, wherein the method further comprises inserting one or more flexible endoscopes into a patient via an oral cavity and/or the anus.

13. The method of claim 1, wherein the distal location is within the ileum, wherein the distal location is further between about 10 centimeters and about 300 centimeters proximal to the ileocecal junction.

14. The method of claim 13, wherein the distal location is about 250 centimeters proximal to the ileocecal junction.

15. The method of claim 1, wherein the distal location is within a select one of an ascending portion of the colon, a transverse portion of the colon, and a descending portion of the colon.

16. The method of claim 1, wherein the first initial length of the small intestine comprises an overall length of the small intestine, and wherein the second length is less than about 60% of the first initial length of the small intestine.

17. The method of claim 1, wherein the proximal location is about 100 centimeters from the ligament of Treitz, and wherein the distal location is about 250 centimeters proximal to the ileocecal junction.

18. The method of claim 1, wherein the connection comprises a side-to-side anastomosis.

19. The method of claim 18, further comprising forming the anastomosis by compression, wherein the act of forming the anastomosis further comprises:
  (a) introducing a first magnetically attractable device to a first attachment region at the proximal location;
  (b) introducing a second magnetically attractable device to a second attachment region at the distal location; and
  (c) compressing a first lumen wall at the first attachment region and a second lumen wall at the second attachment region between the first and second magnetically attractable devices,
  wherein the first and/or the second magnetically attractable device comprises a magnet, and
  wherein the first magnetically attractable device comprises a surface configured to be oriented adjacent to a corresponding surface on the second magnetically attractable device.

20. The method of claim 18, further comprising forming the anastomosis by mechanical fastening, wherein the act of forming the anastomosis further comprises:
  (a) creating a first enterotomy at the proximal location;
  (b) creating a second enterotomy at the distal location; and
  (c) mechanically fastening the first and second enterotomies.

21. The method of claim 1, wherein the connection is established in a procedure selected from the group comprising an open procedure, a laparoscopic procedure, an endoscopic procedure, a procedure using one or more endoscopes inserted through one or more natural orifices, and combinations thereof.

22. A method of creating a pathway within the intestinal tract, the method comprising:
  (a) forming a first opening in a first hollow organ, wherein the first opening is formed within a small intestine of the intestinal tract at a location distal to a duodenal papilla;
  (b) forming a second opening in a second hollow organ;
  (c) inserting a first compression device in the first opening;
  (d) securing a first resilient feature of the first compression device to a first portion of tissue adjacent to the first opening, wherein the secured first resilient feature is positioned on the exterior of the first hollow organ and comprises a bias to alter a configuration of the first compression device between a compressed state and an expanded state when the first resilient feature is positioned on the exterior of the first hollow organ;
  (e) inserting a second compression device in the second opening, the second compression device separated from the first compression device during insertion;
  (f) securing a second resilient feature of the second compression device to a second portion of tissue adjacent to the second opening, wherein the secured second resilient feature is positioned on the exterior of the second hollow organ and comprises a bias to alter a configuration of the second compression device between a compressed state and an expanded state when the second resilient feature is positioned on the exterior of the second hollow organ;
  (g) moving the first and second hollow organs toward each other to align the first and second compression devices with each other; and
  (h) securing the positions of the first and second compression devices relative to each other, wherein a layer of tissue of the first hollow organ and a layer of tissue of the second hollow organ are compressed in apposition between the secured first and second compression devices.

23. The method of claim 22, wherein the second opening is formed proximal to an ileocecal junction.

24. The method of claim 22, wherein the second opening is formed distal to an ileocecal junction.

25. The method of claim 22, wherein the first opening is formed within a jejunum at a location about 100 centimeters distal to a ligament of Treitz, and the second opening is formed within the jejunum at a location about 250 centimeters proximal to an ileocecal junction.

26. The method of claim 22, wherein the first opening is formed within a jejunum at a location about one-third of a length of the jejunum distal to a ligament of Treitz, and the second opening is formed within the jejunum at a location about 250 centimeters proximal to an ileocecal junction.

27. The method of claim 22, wherein the first opening is formed in a proximal portion of a jejunum, and the second opening is formed distal to the first opening at a distance between about 10% and about 70% of a length of a small intestine of the intestinal tract.

* * * * *

UNITED STATES PATENT AND TRADEMARK OFFICE
CERTIFICATE OF CORRECTION

PATENT NO. : 11,033,272 B2
APPLICATION NO. : 15/298816
DATED : June 15, 2021
INVENTOR(S) : Fegelman et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 917 days.

Signed and Sealed this
Twentieth Day of December, 2022

Katherine Kelly Vidal
*Director of the United States Patent and Trademark Office*